US012391644B2

(12) United States Patent
Brown et al.

(10) Patent No.: US 12,391,644 B2
(45) Date of Patent: Aug. 19, 2025

(54) POTASSIUM CHANNEL INHIBITORS

(71) Applicant: Saniona A/S, Glostrup (DK)

(72) Inventors: David Tristram Brown, Glostrup (DK); Palle Christophersen, Glostrup (DK); Thomas Amos Jacobsen, Glostrup (DK); Janus S. Larsen, Glostrup (DK); Pernille Hartveit Poulsen, Glostrup (DK); Dorte Strøbaek, Glostrup (DK)

(73) Assignee: Saniona A/S, Glostrup (DK)

( * ) Notice: Subject to any disclaimer, the term of this patent is extended or adjusted under 35 U.S.C. 154(b) by 0 days.

(21) Appl. No.: 18/652,849

(22) Filed: May 2, 2024

(65) Prior Publication Data

US 2024/0368077 A1  Nov. 7, 2024

Related U.S. Application Data

(62) Division of application No. 17/437,447, filed as application No. PCT/EP2020/057816 on Mar. 20, 2020, now Pat. No. 12,006,289.

(30) Foreign Application Priority Data

Mar. 22, 2019 (EP) .................................... 19164637

(51) Int. Cl.
| | | |
|---|---|---|
| C07D 205/04 | (2006.01) | |
| C07C 211/40 | (2006.01) | |
| C07C 233/62 | (2006.01) | |
| C07C 271/24 | (2006.01) | |
| C07C 311/07 | (2006.01) | |
| C07D 207/09 | (2006.01) | |
| C07D 213/61 | (2006.01) | |
| C07D 265/30 | (2006.01) | |

(52) U.S. Cl.
CPC .......... *C07D 205/04* (2013.01); *C07C 211/40* (2013.01); *C07C 233/62* (2013.01); *C07C 271/24* (2013.01); *C07C 311/07* (2013.01); *C07D 207/09* (2013.01); *C07D 213/61* (2013.01); *C07D 265/30* (2013.01)

(58) Field of Classification Search
None
See application file for complete search history.

(56) References Cited

U.S. PATENT DOCUMENTS

2011/0152239 A1   6/2011   Sugimoto et al.

FOREIGN PATENT DOCUMENTS

| CN | 108929263 A | 12/2018 | |
|---|---|---|---|
| EP | 2287173 A1 | 2/2011 | |
| EP | 2524912 A1 | 11/2012 | |
| WO | 2005/054229 A1 | 6/2005 | |
| WO | 2006/009876 A2 | 1/2006 | |
| WO | WO 2012/116440 * | 9/2012 | ........... C07D 235/14 |
| WO | 2012/155199 A1 | 11/2012 | |
| WO | 2013/191984 A1 | 12/2013 | |
| WO | 2014/001363 A1 | 1/2014 | |
| WO | 2014/067861 A1 | 5/2014 | |
| WO | 2015/124877 A1 | 8/2015 | |
| WO | 2019/055966 A2 | 3/2019 | |

OTHER PUBLICATIONS

Lin et al (Front Immunol 13:997621, 2022) (Year: 2022).*
Wulff et al (J Thromb Haemost 20:2488-2490, 2022) (Year: 2022).*
Peterson et al (Brit J Pharmacol 179:2175-2192, 2022) (Year: 2022).*
Database Registry; Database Accession No. 1779868-68-6, dated Jun. 14, 2015.
Database Registry; Database Accession No. 1782907-49-6, dated Jun. 17, 2015.
Database Registry; Database Accession No. 1784427-62-8, dated Jun. 19, 2015.
Macey et al., "Erythrocyte Membrane Potentials Determined by Hydrogen Ion Distribution", Biochim. Biophys. Acta, 1978, vol. 512, No. 2, pp. 284-295.
Maddox et al., "The Synthesis of Phencyclidine and Other 1-arylcyclohexylamines", J Med Chem, 1965, vol. 8, No. 2, pp. 230-235.
Olivan-Viguera et al., "Novel Phenol inhibitors of small/intermediate-conductance Ca2+-Activated K+ Channels, KCa3.1 and KCa2.3", PLOS One, 2013, vol. 8, No. 3; pp. 1-12.
Shao et al., "Discovery of isoxazole voltage gated sodium channel blockers for treatment of chronic pain", Bioorganic & Medicinal Chemistry Letters; vol. 19, No. 18; 2009, pp. 5334-5338.
STN Registry, Registry No. 1060506-44-6, Chemical Library, 2-Piperidinone, 3-hydroxy-1-methyl-3-[[(1-phenylcyclopropyl)amino]Methyl], Oct. 13, 2008, 1 page.
STN Registry, Registry No. 1779850-08-6, Chemical Library, Aurora Fine Chemicals, N1-[1-(3-Fluorophenyl)cyclopropyl]-1,2-ethanediamine, Jun. 14, 2015, 3 pages.
STN Registry, Registry No. 1779888-00-4, Chemical Library, Aurora Fine Chemicals, N1-[1-(2-Methoxyphenyl)cyclopropyl]-1,2-ethanediamine, Jun. 14, 2015, 3 pages.
STN Registry, Registry No. 1779888-03-7, Chemical Library, Aurora Fine Chemicals, N1-[1-(3-Methoxyphenyl)cyclopropyl]-1,2-ethanediamine, Jun. 14, 2015, 3 pages.
STN Registry, Registry No. 1781630-63-4, Chemical Library, Aurora Fine Chemicals, 3-Pyrrolidinamine, N-[1-(4-chlorophenyl)cyclopropyl], Jun. 17, 2015, pp. 4.
STN Registry, Registry No. 1781650-05-2, Chemical Library, Aurora Fine Chemicals, N1-[1-(4-Methoxyphenyl)cyclopropyl]-1,2-ethanediamine, Jun. 17, 2015, 3 pages.

(Continued)

*Primary Examiner* — Craig D Ricci
(74) *Attorney, Agent, or Firm* — BakerHostetler

(57) ABSTRACT

The present invention relates to novel compounds, pharmaceutical compositions comprising such compounds and their use for treating, alleviating or preventing diseases or disorders relating to the activity of potassium channels.

19 Claims, No Drawings

(56) References Cited

OTHER PUBLICATIONS

STN Registry, Registry No. 1781802-93-4, Chemical Library, Aurora Fine Chemicals, N1-[1-(2-Bromophenyl)cyclopropyl]-1,2-ethanediamine, Jun. 17, 2015, 3 pages.
STN Registry, Registry No. 1781805-33-1, Chemical Library, Aurora Fine Chemicals, N1-[1-(2-Chlorophenyl)cyclopropyl]-1,2-ethanediamine, Jun. 17, 2015, 3 pages.
STN Registry, Registry No. 1781863-45-3, Chemical Library, Aurora Fine Chemicals, N1-[1-(4-Fluorophenyl)cyclopropyl]-1,2-ethanediamine, Jun. 17, 2015, 3 pages.
STN Registry, Registry No. 1782208-61-0, Chemical Library, Aurora Fine Chemicals, 3-Pyrrolidinamine, N-[1-phenylcyclopropyl], Jun. 17, 2015, pp. 4.
STN Registry, Registry No. 1782260-85-8, Chemical Library, Aurora Fine Chemicals, 3-Pyrrolidinamine, N-[1-(2-fluorophenyl)cyclopropyl], Jun. 17, 2015, pp. 4.
STN Registry, Registry No. 1782260-92-7, Chemical Library, Aurora Fine Chemicals, 3-Pyrrolidinamine, N-[1-(3-methylphenyl)cyclopropyl], Jun. 17, 2015, pp. 4.
STN Registry, Registry No. 1782261-00-0, Chemical Library, Aurora Fine Chemicals, 3-Pyrrolidinamine, N-[1-(4-fluorophenyl)cyclopropyl], Jun. 17, 2015, pp. 4.
STN Registry, Registry No. 1782297-65-7, Chemical Library, Aurora Fine Chemicals, 3-Pyrrolidinamine, N-[1-(3-methoxphenyl)cyclopropyl], Jun. 17, 2015, pp. 4.
STN Registry, Registry No. 1782568-52-8, Chemical Library, Aurora Fine Chemicals, 3-Pyrrolidinamine, N-[1-(3-fluorophenyl)cyclopropyl], Jun. 17, 2015, pp. 4.
STN Registry, Registry No. 1782599-81-8, Chemical Library, Aurora Fine Chemicals, N1-[1-(3-Chlorophenyl)cyclopropyl]-1,2-ethanediamine, Jun. 18, 2015, 3 pages.
STN Registry, Registry No. 1782907-04-3, Chemical Library, Aurora Fine Chemicals, 3-Azetidinamine, N-[1-(4-fluorophenyl)cyclopropyl]-N-methyl, Jun. 17, 2015, pp. 4.
STN Registry, Registry No. 1782907-13-4, Chemical Library, Aurora Fine Chemicals, 3-Pyrrolidinamine, N-[1-(2-methylphenyl)cyclopropyl], Jun. 17, 2015, pp. 4.
STN Registry, Registry No. 1782907-22-5, Chemical Library, Aurora Fine Chemicals, 3-Pyrrolidinamine, N-[1-(4-methylphenyl)cyclopropyl], Jun. 17, 2015, pp. 4.
STN Registry, Registry No. 1782907-35-0, Chemical Library, Aurora Fine Chemicals, N1-[1-(2-Fluorophenyl)cyclopropyl]-1,2-ethanediamine, Jun. 18, 2015, 3 pages.
STN Registry, Registry No. 1783336-01-5, Chemical Library, Aurora Fine Chemicals, N1-[1-(2-Methylphenyl)cyclopropyl]-1,2-ethanediamine, Jun. 19, 2015, 3 pages.
STN Registry, Registry No. 1783383-61-8, Chemical Library, Aurora Fine Chemicals, N1-[1-(3-Bromophenyl)cyclopropyl]-1,2-ethanediamine, Jun. 19, 2015, 3 pages.
STN Registry, Registry No. 1784058-20-3, Chemical Library, Aurora Fine Chemicals, N1-[1-(4-Bromophenyl)cyclopropyl]-1,2-ethanediamine, Jun. 20, 2015, 3 pages.
STN Registry, Registry No. 1784058-65-6, Chemical Library, Aurora Fine Chemicals, 3-Pyrrolidinamine, N-[1-(2-methoxphenyl)cyclopropyl], Jun. 19, 2015, pp. 4.
STN Registry, Registry No. 1784062-35-6, Chemical Library, Aurora Fine Chemicals, 3-Pyrrolidinamine, N-[1-(3-chlorophenyl)cyclopropyl], Jun. 19, 2015, pp. 4.
STN Registry, Registry No. 1784062-63-0, Chemical Library, Aurora Fine Chemicals, N1-[1-(4-Chlorophenyl)cyclopropyl]-1,2-ethanediamine, Jun. 20, 2015, 3 pages.
STN Registry, Registry No. 1784139-60-1, Chemical Library, Aurora Fine Chemicals, N1-[1-(3-Methylphenyl)cyclopropyl]-1,2-ethanediamine, Jun. 20, 2015, 3 pages.
STN Registry, Registry No. 1784139-69-0, Chemical Library, Aurora Fine Chemicals, N1-[1-(4-Methylphenyl)cyclopropyl]-1,2-ethanediamine, Jun. 20, 2015, 3 pages.
STN Registry, Registry No. 1784140-36-8, Chemical Library, Aurora Fine Chemicals, N1-(1-Phenylcyclopropyl)-1,2-ethanediamine, Jun. 20, 2015, 3 pages.
STN Registry, Registry No. 1784153-03-2, Chemical Library, Aurora Fine Chemicals, 3-Pyrrolidinamine, N-[1-(4-methoxphenyl)cyclopropyl], Jun. 19, 2015, pp. 4.
STN Registry, Registry No. 1789870-22-2, Chemical Library, Aurora Fine Chemicals, 3-Pyrrolidinamine, N-[1-(2-chlorophenyl)cyclopropyl], Jun. 14, 2015, pp. 4.
STN Registry, Registry No. 1797225-92-3, Chemical Library, Aurora Fine Chemicals, 1-[2-[[1-(4-Bromophenyl)cyclopropyl]amino]ethyl]-2,5-pyrrolidinedione, Jul. 9, 2015, 3 pages.
STN Registry, Registry No. 1797712-15-2, Chemical Library, Aurora Fine Chemicals, N-[1-(3-Chlorophenyl)cyclopropyl]-4-morpholineethanamine, Jul. 10, 2015, 3 pages.
STN Registry, Registry No. 1867317-95-0, Chemical Library, Aurora Fine Chemicals, 3-Pyrrolidinol, 4-[(1-phenylcyclopropyl)amino]-,(3R,4R)-, Feb. 16, 2016, pp. 5.
STN Registry, Registry No. 2125361-45-5, Chemical Library, Aurora Fine Chemicals, N-[1-(2,5-Difluorophenyl)cyclopropyl]-a-methyl-4-morpholineethanamine , Sep. 7, 2015, 3 pages.
STN Registry, Registry No. 2125598-67-4, Chemical Library, Aurora Fine Chemicals, 1-Pyrrolidinecarboxylic acid,3-[[1-(3-chlorophenyl)cyclopropyl]amino]-, ethyl ester, Sep. 6, 2017, pp. 4.
STN Registry, Registry No. 2125614-18-6, Chemical Library, Aurora Fine Chemicals, 1-Pyrrolidinecarboxylic acid,3-[[1-(2,5-difluorophenyl)cyclopropyl]amino]-, ethyl ester, Sep. 6, 2017, pp. 4.
Strøbæk et al., "NS6180, a new KCa3.1 channel inhibitor prevents T-cell activation and inflammation in a rat model of inflammatory bowel disease", British Journal of Pharmacology, 2013, vol. 168(2), pp. 284-295.
U.S. Appl. No. 17/437,447, filed Sep. 9, 2021.
Dell et al., "Uber alkylsubstituierte 1-Arylcyclohexylamino-alkyl-tert.amine", Arch der Pharm, 1967, vol. 300, No. 11, pp. 933-939.

* cited by examiner

POTASSIUM CHANNEL INHIBITORS

CROSS-REFERENCE TO RELATED APPLICATIONS

This application is a divisional of U.S. patent application Ser. No. 17/437,447, filed Sep. 9, 2021, which is the National Stage of International Patent Application No. PCT/EP2020/057816, filed Mar. 20, 2020, which claims the benefit of European Patent Application No. 19164637.1, filed Mar. 22, 2019, the disclosures of which are incorporated herein by reference in their entireties for any and all purposes.

TECHNICAL FIELD

The present invention relates to novel compounds, pharmaceutical compositions comprising such compounds and their use for treating, alleviating or preventing diseases or disorders relating to the activity of potassium channels.

BACKGROUND

Ion channels are trans-membrane proteins, which catalyse the transport of inorganic ions across cell membranes. The ion channels participate in very diverse processes among which is the generation and timing of action potentials, synaptic transmission, secretion of hormones, and contraction of muscles.

All mammalian cells express potassium ($K^+$) channels in their cell membranes, and the channels play a dominant role in the regulation of the membrane potential. In nerve and muscle cells they influence the form of the action potential, regulate the frequency and firing patterns of action potentials, the release of neurotransmitters as well as the degree of bronchodilation and vasodilation. In non-excitable cells $K^+$ channels regulate cellular proliferation and migration as well as the secretion of cytokines.

From a molecular and functional point of view, the $K^+$ channels represent the largest and most diverse group of ion channels. It can be divided into four broad families:
 voltage-activated $K^+$ channels ($K_v$),
 inward rectifier $K^+$ channels (KIR),
 two-pore $K^+$ channels (K2P), and
 calcium-activated $K^+$ channels ($K_{Ca}$).
In the $K_{Ca}$ channels, two main groups can be distinguished:
 the calmodulin-dependent families, consisting of the small conductance (SK's or $K_{Ca}2.x$) and intermediate conductance channels (IK or $K_{Ca}3.1$), and
 the intracellular ligand gated families, consisting of the classic $Ca^{2+}$— and voltage-activated big conductance channel (BK, $K_{Ca}1.1$) as well as channels sensitive to other intracellular ions ($K_{Ca}4.x$; and $K_{Ca}5.1$).

$K_{Ca}3.1$ $K_{Ca}3.1$ is a $Ca^{2+}$-activated K channel encoded by the human gene KCNN4. The channel is a tetramer consisting of four identical α-subunits creating the transmembrane $K^+$ selective pore at their interfaces, and—at the intracellular side—four calmodulins, which bind incoming $Ca^{2+}$ and open the pore for K efflux. $K_{Ca}3.1$ is expressed in many immune cells incl. T- and B-lymphocytes, mast cells, neutrophils, and macrophages, as well as in erythrocytes, fibroblasts, epithelia and endothelia, whereas $K_{Ca}3.1$ is essentially absent from excitable cells, such as heart, smooth, and striated muscles, and neurons. Furthermore, since $K_{Ca}3.1$ is essentially absent from excitable cells, pharmacological modulation of this channel is not expected to cause cardiovascular and CNS related adverse effects.

$K_{Ca}3.1$ in Immune Cells

The role of $K_{Ca}3.1$ in immune cells is here described for T-cells but is also valid for other immune cells and for fibroblasts. Activated T-cells (including Th0, Th1 and Th2) require sustained high and strictly controlled intracellular $Ca^{2+}$-concentration to orchestrate activation of enzymes and nuclear transcription factors (eg. the $Ca^{2+}$-dependent calcineurine/NFAT system) for control of the immune response. Cytosolic $Ca^{2+}$ is dynamically regulated via intracellular stores, but long-term $Ca^{2+}$-elevation requires influx from the extracellular space. This causes membrane depolarization, which reduces further influx and quickly terminates the process if not counteracted. This is achieved by $K_{Ca}3.1$ activation and K efflux keeping the membrane potential negative. Molecular adaptations occur to consolidate the mechanism long-term: The $K_{Ca}3.1$ channel is phosphorylated by the H-kinase NDPK-B, which increases its maximal activity, and $K_{Ca}3.1$ expression is upregulated secondary to NFAT activation. Both processes strengthen the hyperpolarizing capacity of $Ca^{2+}$ mediated $K_{Ca}3.1$ activation.

Efficient maintenance of high-level cytosolic $Ca^{2+}$ homeostasis is beneficial in controlled immune reactions, while it can be severely pathogenic if becoming an uncontrolled autonomous process.

$K_{Ca}3.1$ in Erythrocytes

Erythrocytes travel between lungs, where 02 is picked up from alveolar air, and all other tissues, where 02 is delivered for use in oxidative phosphorylation. The gas exchange occurs in the smallest blood vessels and the erythrocyte needs to be flexible and adapt size to pass the capillary bed.

In this process, $K_{Ca}3.1$ is activated by the $Ca^{2+}$-influx through Piezol, which is a $Ca^{2+}$-permeable channel that is turned-on by the mechanical stress to the membrane during passage. $K^+$ efflux then drives $Cl^-$ and water efflux resulting in a fast and transient shrinkage allowing a smooth passage. Safe on the other side, where the blood vessels widen out again, both channels close and the salt ($K^+$, $Cl^-$, $Ca^{2+}$) and water gradients are quickly restored by active transport processes, making the erythrocyte ready for the next passage.

Potassium Channel Modulators

Consequently, compounds acting as potassium channel modulating agents may be very useful in the treatment, alleviation and/or prevention of diseases like inflammatory bowel diseases (IBD), xerocytosis erythrocytes and acute respiratory distress syndrome (ARDS).

WO 2014/001363 discloses tetrazole derivatives functioning as potassium channel modulators, which are suitable for use in treating diseases and disorders relating to the activity of potassium channels.

WO 2013/191984 discloses fused thiazine-3-ones, which are suitable for the treatment of diseases related to $K_{Ca}3.1$.

WO 2014/067861 discloses 3,4-disubstituted oxazolidinone derivatives and their use as inhibitors of calcium activated potassium channel.

Strøbæk et al. (2013) discloses the K(Ca) 3.1 channel inhibitor4-[[3-(Trifluoromethyl)-phenyl]methyl]-2H-1,4-benzothiazin-3(4H)-one (NS6180).

$K_{Ca}3.1$ is known to play an essential role in diseases such as IBD, hereditary xerocytosis, and ARDS, and thus $K_{Ca}3.1$ is a promising target for treatment of these diseases. Hence, there is a need for provision of $K_{Ca}3.1$ modulators.

Many known potassium channel modulating agents have poor solubility in water. Thus, there is a further need for potassium channel modulators, such as $K_{Ca}3.1$ modulators, which are more soluble in water.

SUMMARY

In one aspect, the current invention relates to a compound of formula (XVI):

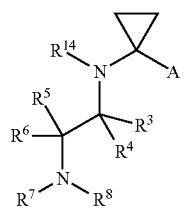

Formula (XVI)

wherein
$R^{14}$ is selected from the group consisting of —C(O)—$C_{1-8}$ alkyl; —C(O)—O—$C_{1-8}$ alkyl; —$C_{2-8}$ alkyl; —H and —S(O)$_2$—$C_{1-8}$ alkyl;
$R^3$ is H, $C_{1-5}$ alkyl, or a bond;
$R^4$ is H, $C_{1-5}$ alkyl, or a bond;
$R^5$ is H, a bond, or $C_{1-8}$alkyl, wherein one methylene group optionally is replaced by —O—;
$R^6$ is H, a bond, or $C_{1-8}$alkyl, wherein one methylene group optionally is replaced by —O—;
$R^7$ is H, a bond, —OH, or $C_{1-8}$alkyl, wherein one or more methylene group optionally and individually is replaced by —O— and/or substituted with =O;
$R^8$ is H, a bond, —OH, or $C_{1-8}$ alkyl, wherein one or more methylene group optionally and individually is replaced by —O— and/or substituted with =O;
Anyone of $R^3$, $R^4$, $R^5$, $R^6$, $R^7$, and $R^8$ optionally is linked together to form a ring;
A is a phenyl or a pyridinyl, wherein the phenyl or pyridinyl is optionally substituted with one or more substituents $R^{13}$ individually selected from the group consisting of halogen, —CX$_3$, —OCX$_3$, —CHX$_2$, —OCHX$_2$, —CH$_2$X, —OCH$_2$X, —CH$_2$CX$_3$, OCH$_2$CX$_3$, —$C_{1-8}$ alkyl, —O$C_{1-8}$ alkyl, —$C_{3-7}$ cycloalkyl, —O$C_{3-7}$ cycloalkyl, —CN, NO$_2$, —SO$_2$CH$_3$, and —SF$_5$; and
X is halogen;
or a pharmaceutically acceptable salt thereof.
In one aspect, the current invention relates to a compound of formula (I):

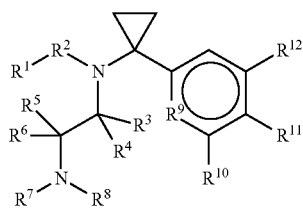

Formula (I)

wherein
$R^1$ is —O$C_{1-8}$ alkyl, —$C_{1-8}$ alkyl, optionally substituted with —OH, or H;
$R^2$ is a bond, —C(O)—, —S(O)$_2$—, or —C(H)$_2$—;
$R^3$ is H, $C_{1-5}$ alkyl, or a bond;
$R^4$ is H, $C_{1-5}$ alkyl, or a bond;
$R^5$ is H, a bond, or $C_{1-8}$ alkyl, wherein one methylene group optionally is replaced by —O—;
$R^6$ is H, a bond, or $C_{1-8}$ alkyl, wherein one methylene group optionally is replaced by —O—;
$R^7$ is H, a bond, —OH, or $C_{1-8}$ alkyl, wherein one or more methylene group optionally and individually is replaced by —O— and/or substituted with =O;
$R^8$ is H, a bond, —OH, or $C_{1-8}$ alkyl, wherein one or more methylene group optionally and individually is replaced by —O— and/or substituted with =O; Anyone of $R^3$, $R^4$, $R^5$, $R^6$, $R^7$, and $R^8$ optionally is linked together to form a ring;
$R^9$ is —C(H)— or —N—;
$R^{10}$ is H or halogen;
$R^{11}$ is H or halogen;
$R^{12}$ is —CX$_3$, —OCX$_3$, H or halogen; and
X is halogen;
or a pharmaceutically acceptable salt thereof.

In a further aspect, the present invention relates to a pharmaceutical composition comprising the compound as disclosed herein.

Compounds of the present invention has a high solubility in aqueous medium. Furthermore, compounds of the present invention are active as potassium channel modulators. They are therefore of great interest for the treatment, alleviation and/or prevention of diseases related to potassium channels. Hence, the present invention also relates to the use of a compound as disclosed herein as a medicament. In one aspect, the compound as disclosed herein is used in the treatment of inflammatory bowel disease (IBD). In another aspect, the compound as disclosed herein is used in the treatment of hereditary xerocytosis. In yet another aspect, the compound as disclosed herein is used in the treatment of acute respiratory distress syndrome (ARDS).

DETAILED DESCRIPTION

Compounds

In one aspect, the present invention relates to a compound of formula (VII):

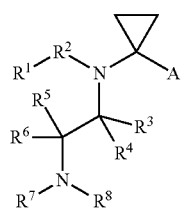

Formula (VII)

wherein
$R^1$ is —O$C_{1-8}$ alkyl, —$C_{1-8}$ alkyl, optionally substituted with —OH, or H;
$R^2$ is a bond, —C(O)—, —S(O)$_2$—, or —C(H)$_2$—;
$R^3$ is H, $C_{1-5}$ alkyl, or a bond;
$R^4$ is H, $C_{1-5}$ alkyl, or a bond;
$R^5$ is H, a bond, or $C_{1-8}$ alkyl, wherein one methylene group optionally is replaced by —O—;
$R^6$ is H, a bond, or $C_{1-8}$ alkyl, wherein one methylene group optionally is replaced by —O—;
$R^7$ is H, a bond, —OH, or $C_{1-8}$ alkyl, wherein one or more methylene group optionally and individually is replaced by —O— and/or substituted with =O;

R[8] is H, a bond, —OH, or $C_{1-8}$ alkyl, wherein one or more methylene group optionally and individually is replaced by —O— and/or substituted with =O; Anyone of R[3], R[4], R[5], R[6], R[7], and R[8] optionally is linked together to form a ring;

A is a phenyl or a pyridinyl, wherein the phenyl or pyridinyl is optionally substituted with one or more substituents R[13] individually selected from the group consisting of halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$; and X is halogen;

or a pharmaceutically acceptable salt thereof.

In one embodiment, the compound is of formula (XVI):

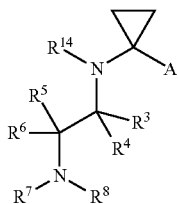

Formula (XVI)

wherein

R[14] is selected from the group consisting of —C(O)—$C_{1-8}$ alkyl; —C(O)—O—$C_{1-8}$ alkyl; —$C_{2-8}$ alkyl; —H and —$S(O)_2$—$C_{1-8}$ alkyl;

R[3] is H, $C_{1-5}$ alkyl, or a bond;

R[4] is H, $C_{1-5}$ alkyl, or a bond;

R[5] is H, a bond, or $C_{1-8}$ alkyl, wherein one methylene group optionally is replaced by —O—;

R[6] is H, a bond, or $C_{1-8}$ alkyl, wherein one methylene group optionally is replaced by —O—;

R[7] is H, a bond, —OH, or $C_{1-8}$ alkyl, wherein one or more methylene group optionally and individually is replaced by —O— and/or substituted with =O;

R[8] is H, a bond, —OH, or $C_{1-8}$ alkyl, wherein one or more methylene group optionally and individually is replaced by —O— and/or substituted with =O;

Anyone of R[3], R[4], R[5], R[6], R[7], and R[8] optionally is linked together to form a ring;

A is a phenyl or a pyridinyl, wherein the phenyl or pyridinyl is optionally substituted with one or more substituents R[13] individually selected from the group consisting of halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$; and X is halogen;

or a pharmaceutically acceptable salt thereof.

In one embodiment, A is a moiety of formula (IX):

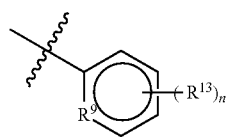

Formula (IX)

wherein

R[9] is —C(H)—, —N—, or —C(R[13])—;

R[13] is individually selected from the group consisting of halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$;

n is an integer of 0 to 4; and

X is halogen.

Thus, in one embodiment, the compound is of formula (VIII):

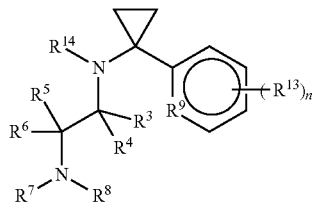

Formula (VIII)

wherein

R[14] is selected from the group consisting of —C(O)—$C_{1-8}$ alkyl; —C(O)—O—$C_{1-8}$ alkyl; —$C_{2-8}$ alkyl; —H and —$S(O)_2$—$C_{1-8}$ alkyl;

R[3] is H, $C_{1-5}$ alkyl, or a bond;

R[4] is H, $C_{1-5}$ alkyl, or a bond;

R[5] is H, a bond, or $C_{1-8}$ alkyl, wherein one methylene group optionally is replaced by —O—;

R[6] is H, a bond, or $C_{1-8}$ alkyl, wherein one methylene group optionally is replaced by —O—;

R[7] is H, a bond, —OH, or $C_{1-8}$ alkyl, wherein one or more methylene group optionally and individually is replaced by —O— and/or substituted with =O;

R[8] is H, a bond, —OH, or $C_{1-8}$ alkyl, wherein one or more methylene group optionally and individually is replaced by —O— and/or substituted with =O;

Anyone of R[3], R[4], R[5], R[6], R[7], and R[8] optionally is linked together to form a ring; and R[9] is —C(H)—, —N—, or —C(R[13])—;

R[13] is individually selected from the group consisting of halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$;

n is an integer of 0 to 4; and

X is halogen;

or a pharmaceutically acceptable salt thereof.

In one embodiment, A is a moiety of formula (X):

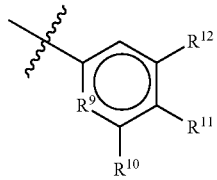

Formula (X)

wherein

R[9] is —C(H)—, —N—, or —C(R[13])—;

R[10], R[11], R[12], and R[13] are individually selected from the group consisting of H, halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$; and X is halogen.

Thus, in one embodiment, the compound is of formula (I):

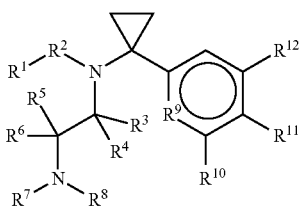

Formula (I)

wherein $R^1$ is —$OC_{1-8}$ alkyl, —$C_{1-8}$ alkyl, optionally substituted with —OH, or H;

$R^2$ is a bond, —C(O)—, —S(O)$_2$—, or —C(H)$_2$—;

$R^3$ is H, $C_{1-5}$ alkyl, or a bond;

$R^4$ is H, $C_{1-5}$ alkyl, or a bond;

$R^5$ is H, a bond, or $C_{1-8}$ alkyl, wherein one methylene group optionally is replaced by —O—;

$R^6$ is H, a bond, or $C_{1-8}$ alkyl, wherein one methylene group optionally is replaced by —O—;

$R^7$ is H, a bond, —OH, or $C_{1-8}$ alkyl, wherein one or more methylene group optionally and individually is replaced by —O— and/or substituted with =O;

$R^8$ is H, a bond, —OH, or $C_{1-8}$ alkyl, wherein one or more methylene group optionally and individually is replaced by —O— and/or substituted with =O;

Anyone of $R^3$, $R^4$, $R^5$, $R^6$, $R^7$, and $R^8$ optionally is linked together to form a ring;

$R^9$ is —C(H)—, —N—, or —C($R^{13}$)—;

$R^{10}$, $R^{11}$, $R^{12}$, and $R^{13}$ are individually selected from the group consisting of H, halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$; and X is halogen;

or a pharmaceutically acceptable salt thereof.

In one embodiment, the present invention relates to a compound of formula (I):

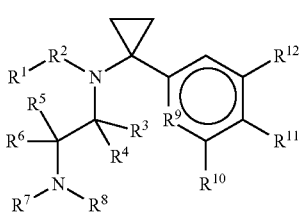

Formula (I)

wherein $R^1$ is —$OC_{1-8}$ alkyl, —$C_{1-8}$ alkyl, optionally substituted with —OH, or H;

$R^2$ is a bond, —C(O)—, —S(O)$_2$—, or —C(H)$_2$—;

$R^3$ is H, $C_{1-5}$ alkyl, or a bond;

$R^4$ is H, $C_{1-5}$ alkyl, or a bond;

$R^5$ is H, a bond, or $C_{1-8}$ alkyl, wherein one methylene group optionally is replaced by —O—;

$R^6$ is H, a bond, or $C_{1-8}$ alkyl, wherein one methylene group optionally is replaced by —O—;

$R^7$ is H, a bond, —OH, or $C_{1-8}$ alkyl, wherein one or more methylene group optionally and individually is replaced by —O— and/or substituted with =O;

$R^8$ is H, a bond, —OH, or $C_{1-8}$ alkyl, wherein one or more methylene group optionally and individually is replaced by —O— and/or substituted with =O;

Anyone of $R^3$, $R^4$, $R^5$, $R^6$, $R^7$, and $R^8$ optionally is linked together to form a ring;

$R^9$ is —C(H)— or —N—;

$R^{10}$ is H or halogen;

$R^{11}$ is H or halogen;

$R^{12}$ is —$CX_3$, —$OCX_3$, H or halogen; and

X is halogen;

or a pharmaceutically acceptable salt thereof.

In one embodiment, the compound is of formula (XVII):

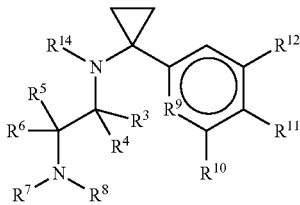

Formula (XVII)

wherein $R^{14}$ is selected from the group consisting of —C(O)—$C_{1-8}$ alkyl; —C(O)—O—$C_{1-8}$ alkyl; —$C_{2-8}$ alkyl; —H and —S(O)$_2$—$C_{1-8}$ alkyl;

$R^3$ is H, $C_{1-5}$ alkyl, or a bond;

$R^4$ is H, $C_{1-5}$ alkyl, or a bond;

$R^5$ is H, a bond, or $C_{1-8}$ alkyl, wherein one methylene group optionally is replaced by —O—;

$R^6$ is H, a bond, or $C_{1-8}$alkyl, wherein one methylene group optionally is replaced by —O—;

$R^7$ is H, a bond, —OH, or $C_{1-8}$ alkyl, wherein one or more methylene group optionally and individually is replaced by —O— and/or substituted with =O;

$R^8$ is H, a bond, —OH, or $C_{1-8}$ alkyl, wherein one or more methylene group optionally and individually is replaced by —O— and/or substituted with =O;

Anyone of $R^3$, $R^4$, $R^5$, $R^6$, $R^7$, and $R^8$ optionally is linked together to form a ring;

$R^9$ is —C(H)— or —N—;

$R^{10}$ is H or halogen;

$R^{11}$ is H or halogen;

$R^{12}$ is —$CX_3$, —$OCX_3$, H or halogen; and

X is halogen;

or a pharmaceutically acceptable salt thereof.

It is well understood that the term "$C_{1-10}$ alkyl" comprises $C_1$ alkyl, $C_2$ alkyl, $C_3$ alkyls, $C_4$ alkyls, $C_5$ alkyls, $C_6$ alkyls, $C_7$ alkyls, $C_8$ alkyls, $C_9$ alkyls, and $C_{10}$ alkyl. Said alkyl may be linear, branched and/or cyclic. Thus, said alkyl may be partly cyclic. For example, "$C_1$-$C_6$-alkyl" designates an alkyl group containing from 1 to 6 carbon atoms that can be linear or branched such as methyl, ethyl, prop-1-yl, prop-2-yl, iso-propyl, tert-butyl, but-1-yl, but-2-yl, pent-1-yl, pent-2-yl, pent-3-yl, 2-methylbut-1-yl, 3-methylbut-1-yl), hex-1-yl or 2,3-dimethylbut-1-yl.

For example, "$C_3$-$C_7$-cycloalkyl" designates a saturated monocyclic carbocyclic ring containing from 3 to 7 carbon atoms such as cyclopropyl, cyclobutyl, cyclopentyl, cyclohexyl or cycloheptyl.

For example, "$C_1$-$C_6$-alkoxy" designates a —O—$C_1$-$C_6$-alkyl group such as methoxy, ethoxy, 1-propoxy, 2-propoxy, 1-butoxy, 2-butoxy, 2-methyl-2-propoxy, 1-pentoxy, 3-methyl-1-butoxy, 2-pentoxy, 2-methyl-2-butoxy, 1-hexoxy or 3-hexoxy.

In one embodiment, $R^1$ is —$OC_{1-8}$ alkyl, such as —$OC_{1-7}$ alkyl, such as —$OC_{1-6}$ alkyl, such as —$OC_{1-5}$ alkyl, such as —$OC_{1-4}$ alkyl, such as —$OC_{1-3}$ alkyl, such as —$OC_{1-2}$ alkyl, such as —$OC_1$ alkyl. Said alkyl may be linear, branched, cyclic or partly cyclic. In one embodiment, $R^1$ is —$OC_{1-4}$ alkyl.

In one embodiment, $R^1$ is —$C_{1-8}$ alkyl, such as —$C_{1-7}$ alkyl, such as —$C_{1-6}$ alkyl, such as —$C_{1-5}$ alkyl, such as —$C_{1-4}$ alkyl, such as —$C_{1-3}$ alkyl, such as —$C_{1-2}$ alkyl, such as —$C_1$ alkyl. Said alkyl may be linear, branched, cyclic or partly cyclic. In one embodiment, said alkyl is substituted with —OH. In one embodiment, $R^1$ is —$C_{1-4}$ alkyl. In one embodiment, $R^1$ is a cyclic alkyl, such as cyclopropyl, or cyclobutyl.

In one embodiment, $R^1$ is H.

In one embodiment, $R^2$ is a bond. In one embodiment, $R^2$ is —C(O)—. In one embodiment, $R^2$ is —$S(O)_2$—. In one embodiment, $R^2$ is or —$C(H)_2$—.

In one embodiment, $R^2$ is —C(O)— and $R^1$ is —$OC_{1-4}$ alkyl. In one embodiment, $R^2$ is —C(O)— and $R^1$ is —$OC_{1-3}$ alkyl. In one embodiment, $R^2$ is —C(O)— and $R^1$ is —$OCH_3$. In one embodiment, $R^2$ is —C(O)— and $R^1$ is —$OCH_2CH_3$. In one embodiment, $R^2$ is —C(O)— and $R^1$ is —$OC_3$ alkyl, such as —$OCH(CH_3)_2$ or —O-cyclopropyl.

In one embodiment, $R^2$ is —C(O)— and $R^1$ is —$C_{1-3}$ alkyl. In one embodiment, $R^2$ is —C(O)— and $R^1$ is —$C_3$ alkyl, such as cyclopropyl.

In one embodiment, $R^2$ is a bond and $R^1$ is $C_{3-4}$ alkyl, corresponding to $R^2$ is —$C(H)_2$— and $R^1$ is $C_{2-3}$ alkyl.

In one embodiment, $R^2$ is —$C(H)_2$—, and $R^1$ is —$C_3$ alkyl, such as cyclopropyl. In one embodiment, $R^2$ is or —$C(H)_2$—, and $R^1$ is —$C_3$ alkyl, such as n-propyl, substituted with —OH.

In one embodiment, $R^2$ is —$C(H)_2$—, and $R^1$ is a cyclic alkyl, such as cyclopropyl, or cyclobutyl.

In one embodiment, $R^2$ is a bond, and $R^1$ is a cyclic alkyl, such as cyclopropyl, or cyclobutyl.

In one embodiment, $R^2$ is —$S(O)_2$— and $R^1$ is —$C_{1-3}$ alkyl. In one embodiment, $R^2$ is —$S(O)_2$— and $R^1$ is methyl.

In one embodiment, —$R^1$-$R^2$ is not —$CH_3$, such as when $R^2$ is a bond, then $R^1$ is not $C_1$ alkyl.

In one embodiment, —$R^2$—$R^1$ is —$R^{14}$.

In one embodiment, $R^{14}$ is —C(O)—$C_{1-8}$ alkyl. In one embodiment, $R^{14}$ is —C(O)—$C_{1-3}$ alkyl. In one embodiment, $R^{14}$ is —C(O)—$C_3$ alkyl, such as —C(O)-cyclopropyl.

In one embodiment, $R^{14}$ is —C(O)—O—$C_{1-8}$ alkyl. In one embodiment, $R^{14}$ is —C(O)—$OC_{1-3}$ alkyl. In one embodiment, $R^{14}$ is —C(O)—$OCH_3$. In one embodiment, $R^{14}$ is —C(O)—$OCH_2CH_3$. In one embodiment, $R^{14}$ is —C(O)—$OC_3$ alkyl, such as —$OCH(CH_3)_2$ or —O—cyclopropyl.

In one embodiment, $R^{14}$ is —$C_{2-8}$ alkyl, such as $C_{3-4}$ alkyl. In one embodiment, $R^{14}$ is —$C(H)_2$—$C_{3-7}$ cycloalkyl, such as —$C(H)_2$-cyclopropyl or —$C(H)_2$-cyclobutyl. In one embodiment, $R^{14}$ is —$C_{3-7}$ cycloalkyl, such as -cyclopropyl or -cyclobutyl. In one embodiment, $R^{14}$ is —$C_{2-8}$ alkyl, such as $C_{3-4}$ alkyl, substituted with one or more —OH. In one embodiment, $R^4$ is isopropyl substituted with —OH.

In one embodiment, $R^{14}$ is —H.

In one embodiment, $R^{14}$ is —$S(O)_2$—$C_{1-8}$ alkyl. In one embodiment, $R^{14}$ is —$S(O)_2$—$CH_3$.

In one embodiment, $R^3$ is H. In another embodiment, $R^3$ is a bond. In one embodiment, $R^3$ is $C_{1-5}$ alkyl, such as $C_{1-4}$ alkyl, such as $C_{1-3}$ alkyl, such as $C_{1-2}$ alkyl, such as $C_1$ alkyl. Said alkyl may be linear, branched, cyclic or partly cyclic. In one embodiment, $R^3$ is $C_{1-3}$ alkyl.

In one embodiment, $R^4$ is H. In another embodiment, $R^4$ is a bond. In one embodiment, $R^4$ is $C_{1-5}$ alkyl, such as $C_{1-4}$ alkyl, such as $C_{1-3}$ alkyl, such as $C_{1-2}$ alkyl, such as $C_1$ alkyl. Said alkyl may be linear, branched, cyclic or partly cyclic. In one embodiment, $R^4$ is $C_{1-3}$ alkyl.

In one embodiment, both $R^3$ and $R^4$ are H. In another embodiment, only one of $R^3$ and $R^4$ are H, whereas the other is a bond or $C_{1-5}$ alkyl.

In one embodiment, $R^5$ is H. In one embodiment, $R^5$ is a bond. In one embodiment, $R^5$ is $C_{1-8}$ alkyl, such as $C_{1-7}$ alkyl, such as $C_{1-6}$ alkyl, such as $C_{1-5}$ alkyl, such as $C_{1-4}$ alkyl, such as $C_{1-3}$ alkyl, such as $C_{1-2}$ alkyl, such as $C_1$ alkyl. In one embodiment, one of the methylene groups in said alkyl is replaced by —O—, thus forming an ether moiety. In one embodiment, $R^5$ is $C_{1-4}$ alkyl.

In one embodiment, $R^6$ is H. In one embodiment, $R^6$ is a bond. In one embodiment, $R^6$ is $C_{1-8}$ alkyl, such as $C_{1-7}$ alkyl, such as $C_{1-6}$ alkyl, such as $C_{1-5}$ alkyl, such as $C_{1-4}$ alkyl, such as $C_{1-3}$ alkyl, such as $C_{1-2}$ alkyl, such as $C_1$ alkyl. In one embodiment, one of the methylene groups in said alkyl is replaced by —O—, thus forming an ether moiety. In one embodiment, $R^6$ is $C_{1-4}$ alkyl.

In one embodiment, $R^5$ and $R^6$ are H. In one embodiment $R^5$ and $R^6$ are —$CH_3$. In one embodiment, $R^5$ and $R^6$ are linked together to form a ring. Said ring may be a three-membered ring, a four-membered ring, a five-membered ring, a six-membered ring, or a seven-membered ring. In one embodiment, said ring is a three-membered ring. In another embodiment, only one of $R^5$ and $R^6$ are H, whereas the other is a bond or $C_{1-8}$ alkyl. In one embodiment, $R^5$ and $R^6$ are linked together to form a ring as in formula (II), formula (XV) or formula (XXII):

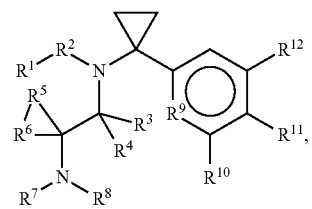

Formula (II)

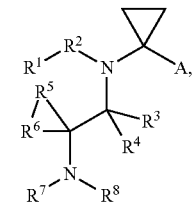

Formula (XV)

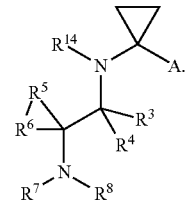

Formula (XXII)

In one embodiment, $R^7$ is H. In one embodiment, $R^7$ is a bond. In one embodiment, $R^7$ is —OH. In one embodiment, $R^7$ is $C_{1-8}$ alkyl, such as $C_{1-7}$ alkyl, such as $C_{1-6}$ alkyl, such as $C_{1-5}$ alkyl, such as $C_{14}$ alkyl, such as $C_{1-3}$ alkyl, such as $C_{1-2}$ alkyl, such as $C_1$ alkyl. In one embodiment, one or more methylene group of said alkyl is replaced by —O—. In one embodiment, said alkyl is substituted with =O, for example $R^7$ is acetyl. In one embodiment, $R^7$ is —C(O)—CH$_3$. In one embodiment, said alkyl is substituted with =O and one or more methylene group of said alkyl is replaced by —O—, for example $R^7$ is methoxycarbonyl. In one embodiment, $R^7$ is —C(O)—O—CH$_3$. In one embodiment, $R^7$ is $C_{1-4}$ alkyl. In one embodiment, $R^7$ is methyl.

In one embodiment, $R^8$ is H. In one embodiment, $R^8$ is a bond. In one embodiment, $R^8$ is —OH. In one embodiment, $R^8$ is $C_{1-8}$ alkyl, such as $C_{1-7}$ alkyl, such as $C_{1-6}$ alkyl, such as $C_{1-5}$ alkyl, such as $C_{14}$ alkyl, such as $C_{1-3}$ alkyl, such as $C_{1-2}$ alkyl, such as $C_1$ alkyl. In one embodiment, one or more methylene group of said alkyl is replaced by —O—. In one embodiment, said alkyl is substituted with =O, for example $R^8$ is acetyl. Thus, in one embodiment, $R^8$ is —C(O)—CH$_3$. In one embodiment, said alkyl is substituted with =O and one or more methylene group of said alkyl is replaced by —O—, for example $R^8$ is methoxycarbonyl. Thus, in one embodiment, $R^8$ is —C(O)—O—CH$_3$. In one embodiment, $R^8$ is $C_{1-4}$ alkyl. In one embodiment, $R^8$ is methyl.

In one embodiment, $R^5$ or $R^6$ is linked to $R^7$ or $R^8$ to form a ring, such as $R^5$ is linked to $R^7$. In one embodiment, when $R^5$ is linked to $R^7$ then $R^6$ and $R^8$ are H. In one embodiment, when $R^5$ is linked to $R^7$ then $R^6$ is H and $R^8$ is methyl. In one embodiment, the ring formed by $R^5$ or $R^6$ linked to $R^7$ or $R^8$, such as $R^5$ is linked to $R^7$, is a four-membered ring, a five-membered ring, a six-membered ring, a three-membered ring or a seven-membered ring. In one embodiment, the ring formed when $R^5$ or $R^6$ is linked to $R^7$ or $R^8$, such as when $R^5$ is linked to $R^7$, is an azetidine. In one embodiment, the ring formed when $R^5$ or $R^6$ is linked to $R^7$ or $R^8$, such as when $R^5$ is linked to $R^7$, is a pyrrolidine. In one embodiment, the ring formed when $R^5$ or $R^6$ is linked to $R^7$ or $R^8$, such as when $R^5$ is linked to $R^7$, is a morpholine. In one embodiment, the ring formed when $R^5$ or $R^6$ is linked to $R^7$ or $R^8$, such as when $R^5$ is linked to $R^7$, is a piperidine. In one embodiment, $R^5$ is linked to $R^7$ as in formula (III), formula (XI) or formula (XVIII):

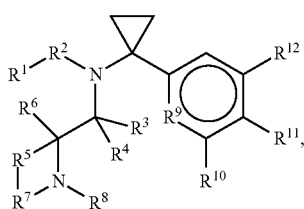

Formula (III)

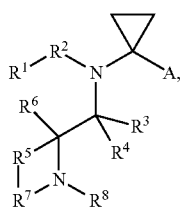

Formula (XI)

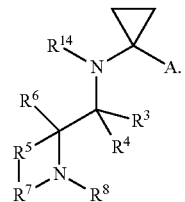

Formula (XVIII)

In one embodiment, the compound is the (S)-enantiomer of formula (III).

In one embodiment, the ring formed when $R^5$ or $R^6$ is linked to $R^7$ or $R^8$, such as when $R^5$ is linked to $R^7$, is a pyrrolidine such as in formula (IV), formula (XII) or formula (XIX):

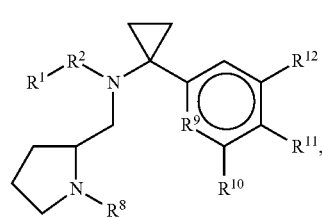

Formula (IV)

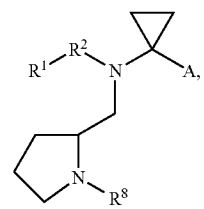

Formula (XII)

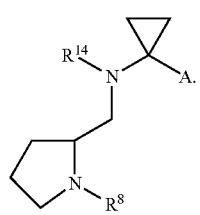

Formula (XIX)

In one embodiment, the compound is the (S)-enantiomer of formula (IV). In one embodiment, the compound is of formula (IV), and $R^9$ is —C(H)— and $R^{10}$ is —H. In one embodiment, the compound is of formula (IV), and $R^9$ is —C(H)—, $R^{10}$ is —H and $R^8$ is —H or $C_{1-3}$ alkyl, such as methyl.

In one embodiment, $R^3$ or $R^4$ is linked to $R^7$ or $R^8$ to form a ring, such as $R^3$ is linked to $R^7$. In one embodiment, when $R^3$ is linked to $R^7$ then $R^4$ and $R^8$ are H. In one embodiment, the ring formed by $R^3$ or $R^4$ linked to $R^7$ or $R^8$, such as $R^3$ linked to $R^7$, is a four-membered ring, a five-membered ring, a six-membered ring, a three-membered ring or a seven-membered ring. In one embodiment, the ring formed when $R^3$ or $R^4$ is linked to $R^7$ or $R^8$, such as when $R^5$ is linked to $R^7$, is a four-membered ring. In one embodiment, the ring formed when $R^3$ or $R^4$ is linked to $R^7$ or $R^8$, such as when $R^3$ is linked to $R^7$, is an azetidine. In one embodiment, $R^3$ is linked to $R^7$ as in formula (V), formula (XIV) or formula (XXI):

Formula (V)

[Chemical structure of Formula (V)]

Formula (XIV)

[Chemical structure of Formula (XIV)]

Formula (XXI)

[Chemical structure of Formula (XXI)]

In one embodiment, $R^3$ or $R^4$ is linked to $R^5$ or $R^6$ to form a ring, such as $R^3$ is linked to $R^5$. In one embodiment, when $R^3$ is linked to $R^5$ then $R^4$ and $R^6$ are H. In one embodiment, the ring formed by $R^3$ or $R^4$ linked to $R^5$ or $R^6$, such as $R^3$ linked to $R^5$, is a five-membered ring, a four-membered ring, a six-membered ring, a three-membered ring or a seven-membered ring. In one embodiment, the ring formed when $R^3$ or $R^4$ is linked to $R^5$ or $R^6$, such as when $R^3$ is linked to $R^5$, is a five-membered ring. In one embodiment, the ring formed when $R^3$ or $R^4$ is linked to $R^5$ or $R^6$, such as when $R^3$ is linked to $R^5$, is a four-membered ring. In one embodiment, the ring formed when $R^3$ or $R^4$ is linked to $R^5$ or $R^6$, such as when $R^3$ is linked to $R^5$, is a cyclopentyl. In one embodiment, $R^3$ is linked to $R^5$ as in formula (VI), formula (XIII) or formula (XX):

Formula (VI)

[Chemical structure of Formula (VI)]

Formula (XIII)

[Chemical structure of Formula (XIII)]

Formula (XX)

[Chemical structure of Formula (XX)]

In one embodiment $R^3$ and $R^4$ are —H, $R^5$ and $R^6$ are methyl, and $R^7$ and $R^8$ are —H.

In one embodiment, no more than five of $R^3$, $R^4$, $R^5$, $R^6$, $R^7$ and $R^8$ are H.

In one embodiment, $R^9$ is —C(H)—, thus forming a benzene ring. In one embodiment, $R^9$ is —N—, thus forming a pyridine ring. In one embodiment, $R^9$ is —C($R^{13}$)—

In one embodiment, $R^{10}$ is H. In another embodiment, $R^{10}$ is a halogen, such as $C_1$.

In one embodiment, $R^{11}$ is H. In another embodiment, $R^{11}$ is a halogen, such as F.

In one embodiment, $R^{12}$ is —$CX_3$, wherein X is halogen. In one embodiment, said halogen is F, thus $R^{12}$ is —$CF_3$. In one embodiment, $R^{12}$ is —$OCX_3$, wherein X is halogen. In one embodiment, said halogen is F, thus $R^{12}$ is —$OCF_3$. In one embodiment, $R^{12}$ is H. In one embodiment, $R^{12}$ is halogen. In one embodiment, $R^{12}$ is Cl. In one embodiment, $R^{12}$ is Br.

In one embodiment $R^{11}$ is F and $R^{12}$ is —$CF_3$. In one embodiment, $R^{10}$ is H, $R^{11}$ is X, and $R^{12}$ is —$CX_3$, wherein X individually is a halogen. In one embodiment, $R^{10}$ is H, $R^{11}$ is F, and $R^{12}$ is —$CF_3$. In one embodiment, $R^9$ is —C(H)—, $R^{10}$ is H, $R^{11}$ is X, and $R^{12}$ is —$CX_3$, wherein X individually is a halogen. In one embodiment, $R^9$ is —C(H)—, $R^{10}$ is H, $R^{11}$ is F, and $R^{12}$ is —$CF_3$. In one embodiment, $R^{10}$ is H, $R^{11}$ is X, and $R^{12}$ is —$OCX_3$, wherein X individually is a halogen. In one embodiment, $R^{10}$ is H, $R^{11}$ is F, and $R^{12}$ is —$OCF_3$. In one embodiment, $R^9$ is —C(H)—, $R^{10}$ is H, $R^{11}$ is X, and $R^{12}$ is —$OCX_3$, wherein X individually is a halogen. In one embodiment, $R^9$ is —C(H)—, $R^{10}$ is H, $R^{11}$ is F, and $R^{12}$ is —$OCF_3$. In one embodiment, $R^9$ is —C(H)—, $R^{10}$ is H, $R^{11}$ is F and $R^{12}$ is —$CF_3$ or —$OCF_3$.

In one embodiment, $R^9$ is —N—, $R^{10}$ is H, $R^{11}$ is X, and $R^{12}$ is —$CX_3$, wherein X individually is a halogen. In one embodiment, $R^9$ is —N—, $R^{10}$ is H, $R^{11}$ is F, and $R^{12}$ is —$CF_3$.

In one embodiment, $R^{10}$ is H and $R^{11}$ is H. In one embodiment, $R^9$ is —C(H)—, $R^{10}$ is H and $R^{11}$ is H. In one embodiment, $R^{10}$ is H, $R^{11}$ is H, and $R^{12}$ is halogen, such as $R^{10}$ is H, $R^{11}$ is H, and $R^{12}$ is Br or $C_1$. In one embodiment, $R^9$ is —C(H)—, $R^{10}$ is H, $R^{11}$ is H, and $R^{12}$ is halogen, such as $R^9$ is —C(H)—, $R^{10}$ is H, $R^{11}$ is H, and $R^{12}$ is Br or $C_1$.

In one embodiment, $R^{10}$ is H, $R^{11}$ is H, and $R^{12}$ is —$CX_3$, wherein X is halogen, such as $R^{10}$ is H, $R^{11}$ is H, and $R^{12}$ is —$CF_3$. In one embodiment, $R^9$ is —C(H)—, $R^{10}$ is H, $R^{11}$ is H, and $R^{12}$ is —$CX_3$, wherein X is halogen, such as $R^{10}$ is H, $R^{11}$ is H, and $R^{12}$ is —$CF_3$.

In one embodiment, $R^{11}$ is H, $R^{10}$ and $R^{12}$ are individually halogen. In one embodiment, $R^{11}$ is H, $R^{10}$ and $R^{12}$ are Cl. In one embodiment, $R^9$ is —C(H)—, $R^{11}$ is H, $R^{10}$ and $R^{12}$ are individually halogen. In one embodiment, $R^9$ is —C(H)—, $R^{11}$ is H, $R^{10}$ and $R^2$ are $C_1$.

In one embodiment, no more than two of $R^{10}$, $R^{11}$ and $R^{12}$ are H. In one embodiment, no more than one of $R^{10}$, $R^{11}$ and $R^{12}$ are H.

In one embodiment, $R^{10}$ is halogen when $R^{11}$ and $R^{12}$ are H.

In one embodiment, when $R^3$, $R^4$, $R^5$, $R^6$, $R^7$ and $R^8$ are H, then no more than two of $R^{10}$, $R^{11}$ and $R^{12}$ are H.

In one embodiment, n is 0. In one embodiment, n is 1. In one embodiment, n is 2. In one embodiment, n is 3. In one embodiment, n is 4.

In one embodiment, $R^{13}$ is —$CX_3$, —$OCX_3$, H or halogen. In one embodiment, $R^{13}$ is H or halogen.

In one embodiment, the compound is not a compound selected from the group consisting of:
N1-[1-(3-chlorophenyl)cyclopropyl]-N1-methyl-1,2-ethanediamine;
N1-[1-(3-fluorophenyl)cyclopropyl]-N1-methyl-1,2-ethanediamine;
N1-[1-(4-bromophenyl)cyclopropyl]-N1-methyl-1,2-ethanediamine;
N1-[1-(4-fluorophenyl)cyclopropyl]-N1-methyl-1,2-ethanediamine;
N1-methyl-N1-(i-phenylcyclopropyl)-1,2-ethanediamine;
N-[1-(4-fluorophenyl)cyclopropyl]-N-methyl-3-azetidinamine;
N-[1-(4-fluorophenyl)cyclopropyl]-N-methyl-3-pyrrolidinamine;
N-[1-(3-fluorophenyl)cyclopropyl]-N-methyl-3-pyrrolidinamine;
N-[1-(3-fluorophenyl)cyclopropyl]-N-methyl-3-azetidinamine;
N-methyl-N-(1-phenylcyclopropyl)-3-pyrrolidinamine;
N-methyl-N-(1-phenylcyclopropyl)-3-azetidinamine;
N-methyl-N-(1-phenylcyclopropyl)-3-piperidinamine;
N-[1-(4-chlorophenyl)cyclopropyl]-N-methyl-3-azetidinamine;
N-[1-(3-chlorophenyl)cyclopropyl]-N-methyl-3-azetidinamine; and
N1-[1-(3-bromophenyl)cyclopropyl]-N1-methyl-1,2-ethanediamine.

In one embodiment, the compound is Methyl N-(2-(dimethylamino)ethyl)-N-(1-(4-fluoro-3-(trifluoromethyl)phenyl)cyclopropyl) carbamate.

In one embodiment, the compound is Methyl (2-amino-2-methylpropyl)(1-(4-fluoro-3-(trifluoromethyl)phenyl)cyclopropyl)carbamate.

In one embodiment, the compound is Methyl((1-aminocyclopropyl)methyl)(1-(4-fluoro-3-(trifluoromethyl)phenyl) cyclopropyl) carbamate.

In one embodiment, the compound is Methyl 3-((1-(4-fluoro-3-(trifluoromethyl)phenyl)cyclopropyl)(methoxycarbonyl)amino)azetidine-1-carboxylate.

In one embodiment, the compound is Methyl azetidin-3-yl(1-(4-fluoro-3-(trifluoromethyl)phenyl)cyclopropyl)carbamate.

In one embodiment, the compound is N-(cyclopropylmethyl)-N-(1-(4-fluoro-3-(trifluoromethyl)phenyl)cyclopropyl)azetidin-3-amine.

In one embodiment, the compound is Methyl (2-aminoethyl)(1-(4-fluoro-3-(trifluoromethyl)phenyl)cyclopropyl) carbamate.

In one embodiment, the compound is N1-(cyclopropyl methyl)-N1-(1-(4-fluoro-3-(trifluoromethyl)phenyl)cyclopropyl)-2-methyl propane-1,2-diamine.

In one embodiment, the compound is N-(2-amino-2-methylpropyl)-N-(1-(4-fluoro-3-(trifluoromethyl)phenyl) cyclopropyl)cyclopropanecarboxamide.

In one embodiment, the compound is N1-cyclopropyl-2-methyl-N1-(1-(3-(trifluoromethyl)phenyl)cyclopropyl)propane-1,2-diamine.

In one embodiment, the compound is Methyl (2-amino-2-methylpropyl)(1-(3,5-dichlorophenyl)cyclopropyl)carbamate.

In one embodiment, the compound is Methyl (2-amino-2-methylpropyl)(1-(3-bromophenyl)cyclopropyl)carbamate.

In one embodiment, the compound is Methyl (2-amino-2-methylpropyl)(1-(3-chlorophenyl)cyclopropyl)carbamate.

In one embodiment, the compound is 1-((azetidin-2-ylmethyl)(1-(4-fluoro-3-(trifluoromethyl)phenyl)cyclopropyl)amino)-2-methyl propan-2-ol.

In one embodiment, the compound is Methyl (2-amino-2-methylpropyl)(1-(3-(trifluoromethyl)phenyl)cyclopropyl) carbamate.

In one embodiment, the compound is 1-((1-(4-fluoro-3-(trifluoromethyl)phenyl)cyclopropyl)((1-methylazetidin-2-yl)methyl)amino)-2-methylpropan-2-ol.

In one embodiment, the compound is Methyl (2-amino-2-methylpropyl)(1-(5-fluoro-4-(trifluoromethyl)pyridin-2-yl)cyclopropyl) carbamate.

In one embodiment, the compound is N1-cyclobutyl-2-methyl-N1-(1-(3-(trifluoromethyl)phenyl)cyclopropyl)propane-1,2-diamine.

In one embodiment, the compound is Ethyl(2-amino-2-methylpropyl)(1-(4-fluoro-3-(trifluoromethyl)phenyl)cyclopropyl)carbamate.

In one embodiment, the compound is Methyl (2-amino-2-methylpropyl)(1-(4-fluoro-3-(trifluoromethoxy)phenyl) cyclopropyl)carbamate.

In one embodiment, the compound is N-(2-amino-2-methylpropyl)-N-(1-(4-fluoro-3-(trifluoromethyl)phenyl) cyclopropyl)methanesulfonamide.

In one embodiment, the compound is Methyl (R)-(1-(4-fluoro-3-(trifluoromethyl)phenyl)cyclopropyl)(pyrrolidin-2-ylmethyl)carbamate.

In one embodiment, the compound is Methyl (S)-(1-(4-fluoro-3-(trifluoromethyl)phenyl)cyclopropyl)(pyrrolidin-2-ylmethyl)carbamate.

In one embodiment, the compound is Methyl (2-acetamido-2-methylpropyl)(1-(4-fluoro-3-(trifluoromethyl)phenyl)cyclopropyl)carbamate.

In one embodiment, the compound is N1-(1-(4-fluoro-3-(trifluoromethyl)phenyl)cyclopropyl)-2-methylpropane-1,2-diamine.

In one embodiment, the compound is Methyl (azetidin-2-ylmethyl)(1-(4-fluoro-3-(trifluoromethyl)phenyl)cyclopropyl)carbamate.

In one embodiment, the compound is Methyl (S)-(1-(4-fluoro-3-(trifluoro methyl) phenyl)cyclopropyl)((1-methylpyrrolidin-2-yl)methyl) carbamate.

In one embodiment, the compound is Methyl (S)-(1-(4-fluoro-3-(trifluoromethoxy)phenyl)cyclopropyl)(pyrrolidin-2-ylmethyl)carbamate.

In one embodiment, the compound is Methyl (R)-(1-(4-fluoro-3-(trifluoromethoxy)phenyl)cyclopropyl)(pyrrolidin-2-ylmethyl)carbamate.

In one embodiment, the compound is Methyl (1-(4-fluoro-3-(trifluoromethyl)phenyl)cyclopropyl)((1-methylazetidin-2-yl)methyl)carbamate.

In one embodiment, the compound is Methyl (R)-(1-(4-fluoro-3-(trifluoromethyl)phenyl)cyclopropyl)((1-methylpyrrolidin-2-yl)methyl)carbamate.

In one embodiment, the compound is Methyl (azetidin-2-ylmethyl)(1-(4-fluoro-3-(trifluoromethoxy)phenyl)cyclopropyl)carbamate.

In one embodiment, the compound is Methyl (1-(4-fluoro-3-(trifluoromethyl)phenyl)cyclopropyl)(2-(hydroxyamino)-2-methylpropyl)carbamate.

In one embodiment, the compound is Ethyl (S)-(1-(4-fluoro-3-(trifluoromethyl)phenyl)cyclopropyl)(pyrrolidin-2-ylmethyl)carbamate.

In one embodiment, the compound is Ethyl (S)-(1-(4-fluoro-3-(trifluoromethyl)phenyl)cyclopropyl)((1-methylpyrrolidin-2-yl)methyl) carbamate.

In one embodiment, the compound is (S)—N-(1-(4-fluoro-3-(trifluoromethyl)phenyl)cyclopropyl)-N-(pyrrolidin-2-ylmethyl) methanesulfonamide.

In one embodiment, the compound is (S)—N-(1-(4-fluoro-3-(trifluoromethyl)phenyl)cyclopropyl)-N-((1-methylpyrrolidin-2-yl)methyl)methanesulfonamide.

In one embodiment, the compound is Ethyl (R)-(1-(4-fluoro-3-(trifluoromethyl)phenyl)cyclopropyl)(pyrrolidin-2-ylmethyl)carbamate.

In one embodiment, the compound is Methyl (R)-(1-(4-fluoro-3-(trifluoromethyl)phenyl)cyclopropyl)(morpholin-3-ylmethyl)carbamate.

In one embodiment, the compound is Methyl (R)-(1-(4-fluoro-3-(trifluoromethyl)phenyl)cyclopropyl)((4-methylmorpholin-3-yl)methyl)carbamate.

In one embodiment, the compound is (R)—N-(1-(4-fluoro-3-(trifluoromethyl)phenyl)cyclopropyl)-N-(pyrrolidin-2-ylmethyl) methane sulphonamide.

In one embodiment, the compound is Methyl (S)-(1-(4-fluoro-3-(trifluoromethyl)phenyl)cyclopropyl)(morpholin-3-ylmethyl)carbamate.

In one embodiment, the compound is Methyl (S)-(1-(4-fluoro-3-(trifluoromethyl)phenyl)cyclopropyl)((4-methylmorpholin-3-yl)methyl)carbamate.

In one embodiment, the compound is Isopropyl (S)-(1-(4-fluoro-3-(trifluoromethyl)phenyl)cyclopropyl)(pyrrolidin-2-ylmethyl)carbamate.

In one embodiment, the compound is Cyclopropyl (S)-(1-(4-fluoro-3-(trifluoromethyl)phenyl)cyclopropyl)(pyrrolidin-2-ylmethyl)carbamate.

In one embodiment, the compound is Methyl (R)-(1-(4-fluoro-3-(trifluoromethyl)phenyl)cyclopropyl)((2-methyl pyrrolidin-2-yl)methyl)carbamate.

In one embodiment, the compound is N-((1-amino cyclopropyl)methyl)-1-(4-fluoro-3-(trifluoromethyl)phenyl)cyclopropan-1-amine.

In one embodiment, the compound is Cyclopropylmethyl (S)-(1-(4-fluoro-3-(trifluoromethyl)phenyl)cyclopropyl) (pyrrolidin-2-ylmethyl)carbamate.

In one embodiment, the compound is N-((1-aminocyclopropyl)methyl)-N-(1-(4-fluoro-3-(trifluoromethyl)-phenyl) cyclopropyl)methanesulfonamide.

In one embodiment, the compound is Methyl (S)-(1-(4-fluoro-3-(trifluoromethyl)phenyl)cyclopropyl)((2-methylpyrrolidin-2-yl)methyl)carbamate.

In one embodiment, the compound is (1S, 2S)—N1-(1-(4-fluoro-3-(trifluoromethyl)phenyl)cyclopropyl)-cyclopentane-1,2-diamine.

In one embodiment, the compound is (1R,2S)—N1-(1-(4-fluoro-3-(trifluoromethyl)phenyl)cyclopropyl)-cyclopentane-1,2-diamine.

In one embodiment, the compound is Methyl (S)-(azetidin-2-ylmethyl)(1-(4-fluoro-3-(trifluoromethyl)phenyl)-cyclopropyl)carbamate.

Solubility of Compounds

One of the advantages of the compounds of the present invention is that they are more soluble than many other compounds known to modulate potassium channels such as $K_{Ca}3.1$. The compounds tested in Example [54] have a solubility in pH 7.4 phosphate buffer of 400 to 1700 μM.

Pharmaceutically Acceptable Salts

The chemical compound of the invention may be provided in any form suitable for the intended administration, including pharmaceutically (i.e. physiologically) acceptable salts. Examples of pharmaceutically acceptable addition salts include, without limitation, non-toxic inorganic and organic acid addition salts such as hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate, toluene-p-sulphonate, and the like. Such salts may be formed by procedures well known and described in the art. Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of the compound of the invention include, without limitation, the sodium, the potassium, the calcium, the magnesium, the zinc, the aluminium, the lithium, the choline, the lysinium, and the ammonium salt, and the like, of the compound of the invention containing an anionic group. Such cationic salts may be formed by procedures well known and described in the art. In the context of this invention the "onium salts" of N-containing compounds are also contemplated as pharmaceutically acceptable salts. Preferred "onium salts" include the alkylonium salts, the cycloalkylonium salts, and the cycloalkylalkylonium salts. In one embodiment, the term "pharmaceutically acceptable salt" of a compound designates any "onium" salts of N-containing compounds or any salt of addition of said active principle with a mineral or organic acid among which acetic, hydrochloric, cinnamic, citric, formic, hydrobromic, hydrolodic, hydrofluoric, malonic, methanesulphconic, oxalic, picric, maleic, lactic, nicotinic, phenylacetic, phosphoric, succinic and tartric acid, ammonium, diethylamine, piperazine, nicotinamide, urea, sodium, potassium, calcium, magnesium, zinc, lithium, methylamino, dimethylamino, trimethylamino and tris(hydroxymethyl)aminomethane acid.

Preparation of Compounds

Compounds according to the present invention may be prepared according to any conventional methods of chemical synthesis known by the skilled person, e.g. those described in the working examples. The starting materials for the processes described in the present application are known or may readily be prepared by conventional methods known by the skilled artisan from commercially available chemicals.

The end products of the reactions described herein may be isolated by conventional technique such as extraction, crystallisation, distillation, chromatography etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Compositions

The present invention also relates to a pharmaceutical composition comprising, for example as an active ingredient, a pharmaceutically effective amount of a compound as disclosed herein. In one embodiment, said pharmaceutical composition comprises a therapeutically effective amount of the compound as disclosed herein or a pharmaceutically acceptable salt thereof, together with at least one pharmaceutically acceptable carrier, excipient or diluent.

While a compound as disclosed herein for use in therapy may be administered in the form of the raw chemical compound, it is preferred to introduce the active ingredient, optionally in the form of a pharmaceutically acceptable salt, in a pharmaceutical composition together with one or more adjuvants, excipients, carriers, buffers, diluents, and/or other customary pharmaceutical auxiliaries.

In one embodiment, the invention provides pharmaceutical compositions comprising a compounds disclosed herein or a pharmaceutically acceptable salt thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof. Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

A compound as disclosed herein, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. A compound as disclosed herein can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

Unlike many of the other known KCa3.1 inhibitors, the compounds of the present invention has a high solubility in aqueous medium, which makes them suitable for liquid drug administration, such as intravenous or infusion administration.

For preparing pharmaceutical compositions from a compound as disclosed herein, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

A therapeutically effective dose refers to that amount of active ingredient, which ameliorates the symptoms or condition. Therapeutic efficacy and toxicity, e.g. $ED_{50}$, may be determined by standard pharmacological procedures in cell cultures or experimental animals. The dose ratio between therapeutic and toxic effects is the therapeutic index and may be expressed by ratio between plasma levels resulting in therapeutic effects and plasma ratios resulting in toxic effects. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 10000 mg of active ingredient per individual dose, such as 0.5 to 2000 mg, preferably of from about 1 to about 1000 mg, most preferred of from about 10 to about 500 mg, are suitable for therapeutic treatments. The active ingredient may be administered in one or several doses per day.

Biological Activity

Compounds of the present invention are active as potassium channel modulators. The compounds of the present invention tested in example [55] all inhibit $K_{Ca}3.1$.

Method of Treatment

Being modulators of potassium ion channels, such as $K_{Ca}3.1$, the compounds of the present invention are of use in the treatment of diseases and disorders of a living body, including human. As used herein, the term "treatment" also includes prevention, and/or alleviation of diseases and disorders. In one aspect, the compound as described herein is for use in medicine. In one aspect, the present invention relates to a method for treatment of IBD, hereditary xerocytosis or ARDS comprising administration of a compound as described herein, or a pharmaceutical composition comprising said compound, to a subject in need thereof.

Inflammatory Bowel Diseases (IBD)

Inflammatory bowel disease (IBD) is a chronic autoimmune disease affecting the gastrointestinal tract with symptoms of abdominal pain, vomiting, diarrhoea, hematochezia, and weight loss. IBD comes in two main forms, ulcerative colitis (UC) and Crohn's disease (CD). UC exclusively affects the colon and rectum, whereas CD may affect the entire gastrointestinal tract. Histologically UC is characterized by extended mucosal inflammation in contrast to CD, where deep punctuate lesions affect all layers of the intestinal wall. It is estimated that approximately 2.5 million patients are diagnosed with IBD (1 million with colitis and 1.5 million with Crohn's patients) in the industrialized world (USA, Japan; 5 major EU countries). The incidences are increasing, especially in newly industrialized countries, possibly related to changes in lifestyle.

Currently used anti-IBD drugs are anti-inflammatory (5-ASA's, steroids), generally immune dampening (azathioprine, 6-mercaptopurine), or biological single cytokine/integrine neutralizing agents (e.g. infleximap, ustekinomap, vedolizumap). Despite these options and carefully optimized clinical procedures, patients still face rounds of gut-shortening surgeries (many Crohn's patients experience at least one surgery in their lifetime), and colitis patients may develop proctitis after colectomy. Suboptimal medical disease control with respect to maintaining long-term remission, to fight flare ups, and especially avoiding development of irreversible structural changes due to irresolvable gut fibrosis, represents a serious unmet need for IBD patients.

Many of the drugs used to treat IBD today are connected with side effects. For example, side effects of steroids include increased susceptibility to infection; and 5-aminosalicylic acids, such as in the form of sulphasalazine, are associated with a significant proportion of non-responders among UC patients, decreased kidney function as well as high and frequent doses, which elicit poor compliance. Drawbacks for TNF-alpha inhibitor infliximab are include high cost, inconvenience of application (injections), waning of efficacy and elicitation of increased risk of infection as a result of their immunosuppressive characteristic; and immunomodulators such asazathioprine, 6-mercaptopurine and methotrexate increase the risk for infections and for some types of cancer, as well as being liver toxic. Thus, there is still a major unmet need for new treatments of inflammatory bowel diseases.

$K_{Ca}3.1$ as a Target for IBD

T cells play an important role in IBD, and IBD processes (immune cell proliferation, homing, and cytokine release), excessive fibroblast-mediated collagen secretion can lead to fibrosis that causes strictures and intestinal obstructions, and excess water transport across the epithelia can lead to diarrhoea. All these pathological processes can be dampened by $K_{Ca}3.1$ inhibition.

As demonstrated herein, the compounds of the present invention inhibit $K_{Ca}3.1$, and thus, in one aspect, the present invention relates to a compound as described herein for use in the treatment, alleviation and/or prevention of inflammatory bowel disease (IBD). In one embodiment, said IBD is colitis, such as ulcerative colitis (UC). In one embodiment, said IBD is Crohn's disease (CD).

Hereditary Xerocytosis

Hereditary xerocytosis, also known as dehydrated stomatocytosis, is characterized by increased fragility and haemolysis of erythrocytes, resulting in a fully compensated or mild to severe anaemia. Increased reticulocyte formation (to compensate for erythrocyte loss), ion-overload and jaundice (resulting from the increased break-down of haemoglobin) are characteristic in adults. New-borns may suffer from transient edema/ascites, which in rare cases may develop to life-threatening hydrops fetalis. The disease is very heterogeneous but is classically identified from a combination of clinical signs, such as fatigue, enlarged spleen, gall stones, thrombosis events, and pulmonary hypertension. Microscopic examination may reveal erythrocytes with abnormal shapes and analysis of haematology parameters reveal shrunken erythrocytes due to salt and water loss. The ethology of hereditary xerocytosis has long been known to differ radically from other hereditary anaemias, such as the haemoglobinopathies (eg. sickle cell anemia and the thalassemia diseases), or glycolytic enzymopathies (eg. glucose-6-phosphate deficiency), in that it is due to a primary membrane permeability defect. The molecular targets involved in this defect have just recently been identified.

$K_{Ca}3.1$ as a Target for Hereditary Xerocytosis

Recent years of scientific investigations have shown that hereditary xerocytosis is due to gain-of-function mutations in either Piezo1 or KCNN4, the gene encoding $K_{Ca}3.1$. Both mutations essentially result in the same phenotype: In the case of Piezo1 mutations $Ca^{2+}$ enters the erythrocyte through the constantly open channel, thus activating $K_{Ca}3.1$ resulting in permanently dehydrated erythrocytes; in the case of KCNN4 mutations $K_{Ca}3.1$ are constitutively open thereby governing erythrocyte dehydration even in the absence of a $Ca^{2+}$-signal from the Piezo1 channel. The clear definition of the genes and mutations responsible for hereditary xerocytosis, allows easy diagnostics of which patients will benefit from the treatment and which should not be treated.

Inhibition of the erythrocyte $K_{Ca}3.1$ channel will counteract unintentional dehydration and presumably prevent haemolysis of xerocytosis erythrocytes and thereby improve the clinical condition of patients. Importantly, the binding site for $K_{Ca}3.1$ inhibitors do not overlap with the known gain-of-function mutations in $K_{Ca}3.1$. This pinpoints $K_{Ca}3.1$ as a pivotal target for all known causes of hereditary xerocytosis.

The compounds of the present invention inhibit $K_{Ca}3.1$. Hence, in one aspect, the present invention relates to a compound described herein for use in the treatment, alleviation and/or prevention of hereditary xerocytosis. Hereditary xerocytosis is one of the most frequent variant of hereditary stomatocytoses, a group of rare disorders characterized by a leak of monovalent cations such as $K^+$ from the red blood cells (RBCs).

Acute Respiratory Distress Syndrome (ARDS)

Acute respiratory distress syndrome is a serious and often lethal complication to lung infections, as caused for example by SARS, MERS, or Covid-19 vira. The infections can lead to global lung inflammation, which widens the ultrathin barriers between the air-filled alveoli and the blood-filled alveolar vessels and fills-up the alveoli with liquid, and thereby hampers the life-essential oxygen/carbon dioxide gas exchange between lung and blood. ARDS is thus a complex condition that involve both components of the immune system as well as the air/blood barrier function. Since there are currently no medical treatments that specifically interfere with ARDS (general immune dampening treatments by steroids are not effective), the only options for patients is medical ventilator treatment at an intensive care unit.

KCa3.1 as a Target for ARDS.

Since the KCa3.1 channel is expressed in both the epithelia and endothelia as well as in the inflammatory cells, such as neutrophils, that participate in lung inflammation, inhibition of KCa3.1 can dampen both the basic inflammation and possibly also protect the air/blood barrier function. Experiments with a mouse model of ARDS have recently shown that KCa3.1 knock-out mice have improved gas exchange, and the improvement was also demonstrated by treatment with the classical KCa3.1 inhibitors senicapoc and TRAM-34. In the clinical situation with patients on medical ventilation, oral drug administration is not optimal, whereas intravenous bolus or infusion administration is preferred. Classical KCa3.1 inhibitors like the triarylmethanes (exemplified by senicapoc and TRAM-34) have extremely low water solubility, which makes IV-formulations very challenging. The same drawbacks apply to known KCa3.1 inhibitors based on other chemical scaffolds.

The compounds of the present invention inhibit $K_{Ca}3.1$. Further, the compounds of the present invention has a high solubility in aqueous medium. Hence, the compounds of the present invention are highly suitable for use in treatment of ARDS. Thus, in one aspect, the present invention relates to a compound as described herein for use in the treatment, alleviation and/or prevention of ARDS.

Items

1. A compound of formula (VII):

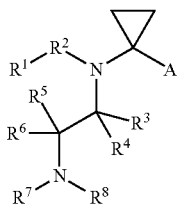

Formula (VII)

wherein
$R^1$ is —$OC_{1-8}$ alkyl, —$C_{1-8}$ alkyl, optionally substituted with —OH, or H;
$R^2$ is a bond, —C(O)—, —S(O)$_2$—, or —C(H)$_2$—;
$R^3$ is H, $C_{1-5}$ alkyl, or a bond;
$R^4$ is H, $C_{1-5}$ alkyl, or a bond;
$R^5$ is H, a bond, or $C_{1-8}$ alkyl, wherein one methylene group optionally is replaced by —O—;
$R^6$ is H, a bond, or $C_{1-5}$ alkyl, wherein one methylene group optionally is replaced by —O—;
$R^7$ is H, a bond, —OH, or $C_{1-8}$alkyl, wherein one or more methylene group optionally and individually is replaced by —O— and/or substituted with =O;
$R^8$ is H, a bond, —OH, or $C_{1-8}$ alkyl, wherein one or more methylene group optionally and individually is replaced by —O— and/or substituted with =O;
Anyone of $R^3$, $R^4$, $R^5$, $R^6$, $R^7$, and $R^8$ optionally is linked together to form a ring;
A is a phenyl or a pyridinyl, wherein the phenyl or pyridinyl is optionally substituted with one or more substituents $R^{13}$ individually selected from the group consisting of halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$; and
X is halogen;
or a pharmaceutically acceptable salt thereof.

2. The compound according to item 1, wherein the compound is of formula (XVI):

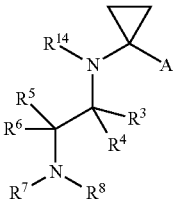

Formula (XVI)

wherein
$R^{14}$ is selected from the group consisting of —C(O)—$C_{1-8}$ alkyl; —C(O)—O—$C_{1-8}$ alkyl; —$C_{2-8}$ alkyl; —H and —S(O)$_2$—$C_{1-8}$ alkyl;
$R^3$ is H, $C_{1-5}$ alkyl, or a bond;
$R^4$ is H, $C_{1-5}$ alkyl, or a bond;
$R^5$ is H, a bond, or $C_{1-8}$ alkyl, wherein one methylene group optionally is replaced by —O—;
$R^6$ is H, a bond, or $C_{1-5}$ alkyl, wherein one methylene group optionally is replaced by —O—;
$R^7$ is H, a bond, —OH, or $C_{1-8}$alkyl, wherein one or more methylene group optionally and individually is replaced by —O— and/or substituted with =O;
$R^8$ is H, a bond, —OH, or $C_{1-8}$alkyl, wherein one or more methylene group optionally and individually is replaced by —O— and/or substituted with =O;
Anyone of $R^3$, $R^4$, $R^5$, $R^6$, $R^7$, and $R^8$ optionally is linked together to form a ring;
A is a phenyl or a pyridinyl, wherein the phenyl or pyridinyl is optionally substituted with one or more substituents $R^{13}$ individually selected from the group consisting of halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$; and
X is halogen;
or a pharmaceutically acceptable salt thereof.

3. The compound according to any one of the preceding items, wherein the compound is of formula (VIII):

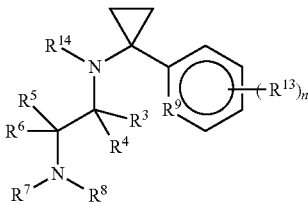

Formula (VIII)

wherein
$R^{14}$ is selected from the group consisting of —C(O)—$C_{1-8}$ alkyl; —C(O)—O—$C_{1-8}$ alkyl; —$C_{2-8}$ alkyl; —H and —S(O)$_2$—$C_{1-8}$ alkyl;
$R^3$ is H, $C_{1-5}$ alkyl, or a bond;
$R^4$ is H, $C_{1-5}$ alkyl, or a bond;
$R^5$ is H, a bond, or $C_{1-8}$ alkyl, wherein one methylene group optionally is replaced by —O—;
$R^6$ is H, a bond, or $C_{1-8}$ alkyl, wherein one methylene group optionally is replaced by —O—;
$R^7$ is H, a bond, —OH, or $C_{1-8}$ alkyl, wherein one or more methylene group optionally and individually is replaced by —O— and/or substituted with =O;
$R^8$ is H, a bond, —OH, or $C_{1-8}$ alkyl, wherein one or more methylene group optionally and individually is replaced by —O— and/or substituted with =O;
Anyone of $R^3$, $R^4$, $R^5$, $R^6$, $R^7$, and $R^8$ optionally is linked together to form a ring; and $R^9$ is —C(H)—, —N—, or —C($R^{13}$)—;
$R^{13}$ is individually selected from the group consisting of halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$;
n is an integer of 0 to 4; and
X is halogen;
or a pharmaceutically acceptable salt thereof.

4. The compound according to item 1, wherein the compound is of formula (I):

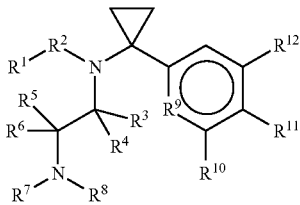

Formula (I)

wherein
$R^1$ is —$OC_{1-8}$ alkyl, —$C_{1-8}$ alkyl, optionally substituted with —OH, or H;
$R^2$ is a bond, —C(O)—, —$S(O)_2$—, or —$C(H)_2$—;
$R^3$ is H, $C_{1-5}$ alkyl, or a bond;
$R^4$ is H, $C_{1-5}$ alkyl, or a bond;
$R^5$ is H, a bond, or $C_{1-8}$ alkyl, wherein one methylene group optionally is replaced by —O—;
$R^6$ is H, a bond, or $C_{1-8}$ alkyl, wherein one methylene group optionally is replaced by —O—;
$R^7$ is H, a bond, —OH, or $C_{1-8}$ alkyl, wherein one or more methylene group optionally and individually is replaced by —O— and/or substituted with =O;
$R^8$ is H, a bond, —OH, or $C_{1-8}$ alkyl, wherein one or more methylene group optionally and individually is replaced by —O— and/or substituted with =O;
Anyone of $R^3$, $R^4$, $R^5$, $R^6$, $R^7$, and $R^8$ optionally is linked together to form a ring;
$R^9$ is —C(H)—, —N—, or —$C(R^{13})$—;
$R^{10}$, $R^{11}$, $R^{12}$, and $R^{13}$ are individually selected from the group consisting of H, halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$; and
X is halogen;
or a pharmaceutically acceptable salt thereof.

5. The compound according to item 1, wherein the compound is of formula (I):

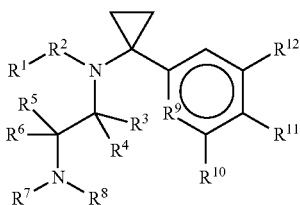

Formula (I)

wherein
$R^1$ is —$OC_{1-8}$ alkyl, —$C_{1-8}$ alkyl, optionally substituted with —OH, or H;
$R^2$ is a bond, —C(O)—, —$S(O)_2$—, or —$C(H)_2$—;
$R^3$ is H, $C_{1-5}$ alkyl, or a bond;
$R^4$ is H, $C_{1-5}$ alkyl, or a bond;
$R^5$ is H, a bond, or $C_{1-8}$ alkyl, wherein one methylene group optionally is replaced by —O—;
$R^6$ is H, a bond, or $C_{1-8}$ alkyl, wherein one methylene group optionally is replaced by —O—;
$R^7$ is H, a bond, —OH, or $C_{1-8}$ alkyl, wherein one or more methylene group optionally and individually is replaced by —O— and/or substituted with =O;
$R^8$ is H, a bond, —OH, or $C_{1-8}$ alkyl, wherein one or more methylene group optionally and individually is replaced by —O— and/or substituted with =O;
Anyone of $R^3$, $R^4$, $R^5$, $R^6$, $R^7$, and $R^8$ optionally is linked together to form a ring;
$R^9$ is —C(H)— or —N—;
$R^{10}$ is H or halogen;
$R^{11}$ is H or halogen;
$R^{12}$ is —$CX_3$, —$OCX_3$, H or halogen; and
X is halogen;
or a pharmaceutically acceptable salt thereof.

6. The compound according to item 1, wherein the compound is of formula (XVII):

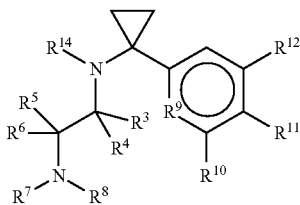

Formula (XVII)

wherein
$R^{14}$ is selected from the group consisting of —C(O)—$C_{1-8}$ alkyl; —C(O)—O—$C_{1-8}$ alkyl; —$C_{2-8}$ alkyl; —H and —$S(O)_2$—$C_{1-8}$ alkyl;
$R^3$ is H, $C_{1-5}$ alkyl, or a bond;
$R^4$ is H, $C_{1-5}$ alkyl, or a bond;
$R^5$ is H, a bond, or $C_{1-8}$ alkyl, wherein one methylene group optionally is replaced by —O—;
$R^6$ is H, a bond, or $C_{1-8}$ alkyl, wherein one methylene group optionally is replaced by —O—;
$R^7$ is H, a bond, —OH, or $C_{1-8}$ alkyl, wherein one or more methylene group optionally and individually is replaced by —O— and/or substituted with =O;
$R^8$ is H, a bond, —OH, or $C_{1-8}$ alkyl, wherein one or more methylene group optionally and individually is replaced by —O— and/or substituted with =O;
Anyone of $R^3$, $R^4$, $R^5$, $R^6$, $R^7$, and $R^8$ optionally is linked together to form a ring;
$R^9$ is —C(H)— or —N—;
$R^{10}$ is H or halogen;
$R^{11}$ is H or halogen;
$R^{12}$ is —$CX_3$, —$OCX_3$, H or halogen; and
X is halogen;
or a pharmaceutically acceptable salt thereof.

7. The compound according to any one of the preceding items, wherein $R^3$ and $R^4$ are —H, $R^5$ and $R^6$ are methyl, and $R^7$ and $R^8$ are —H.

8. The compound according to any one of the preceding items, wherein the compound is of formula (XI):

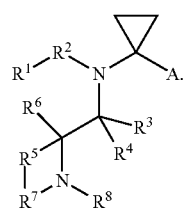

Formula (XI)

9. The compound according to any one of the preceding items, wherein the compound is of formula (XII):

Formula (XII)

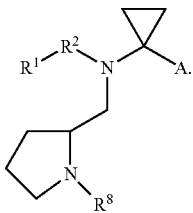

10. The compound according to any one of the preceding items, wherein the compound is of formula (XIII):

Formula (XIII)

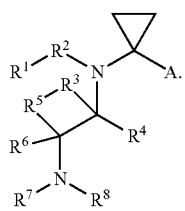

11. The compound according to any one of the preceding items, wherein the compound is of formula (XIV):

Formula (XIV)

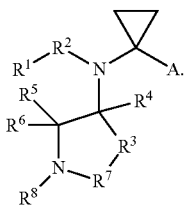

12. The compound according to any one of the preceding items, wherein the compound is of formula (XV):

Formula (XV)

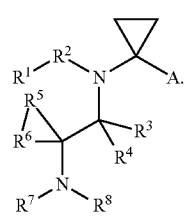

13. The compound according to any one of the preceding items, wherein the compound is of formula (III):

Formula (III)

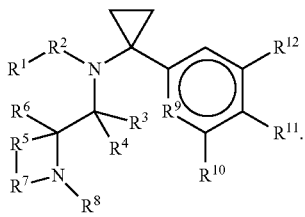

14. The compound according to any one of the preceding items, wherein the compound is of formula (IV):

Formula (IV)

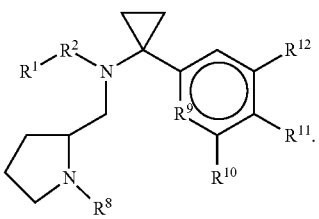

15. The compound according to any one of the preceding items, wherein the compound is of formula (VI):

Formula (VI)

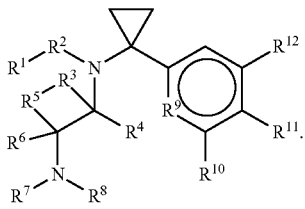

16. The compound according to any one of the preceding items, wherein the compound is of formula (V):

Formula (V)

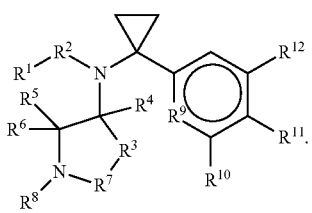

17. The compound according to any one of the preceding items, wherein the compound is of formula (II):

Formula (II)

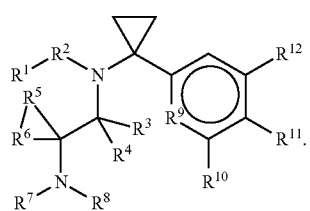

18. The compound according to any one of the preceding items, wherein the compound is of formula (XVIII):

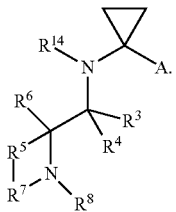

Formula (XVIII)

19. The compound according to any one of the preceding items, wherein the compound is of formula (XIX):

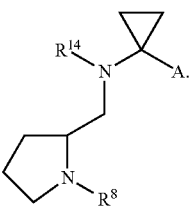

Formula (XIX)

20. The compound according to any one of the preceding items, wherein the compound is of formula (XX):

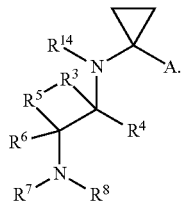

Formula (XX)

21. The compound according to any one of the preceding items, wherein the compound is of formula (XXI):

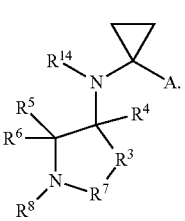

Formula (XXI)

22. The compound according to any one of the preceding items, wherein the compound is of formula (XXII):

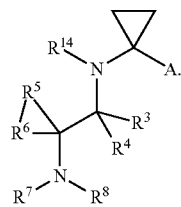

Formula (XXII)

23. The compound according to any one of the preceding items, wherein A is a moiety of formula (IX):

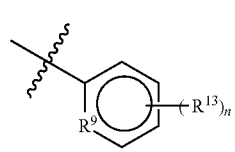

Formula (IX)

wherein
$R^9$ is —C(H)—, —N—, or —C($R^{13}$)—;
$R^{13}$ is individually selected from the group consisting of halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$;
n is an integer of 0 to 4; and
X is halogen.

24. The compound according to any one of the preceding items, wherein A is a moiety of formula (X):

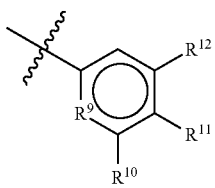

Formula (X)

wherein
$R^9$ is —C(H)—, —N—, or —C($R^{13}$)—;
$R^{10}$, R, $R^{12}$, and $R^{13}$ are individually selected from the group consisting of H, halogen, —$CX_3$, —$OCX_3$, —$CHX_2$, —$OCHX_2$, —$CH_2X$, —$OCH_2X$, —$CH_2CX_3$, $OCH_2CX_3$, —$C_{1-8}$ alkyl, —$OC_{1-8}$ alkyl, —$C_{3-7}$ cycloalkyl, —$OC_{3-7}$ cycloalkyl, —CN, $NO_2$, —$SO_2CH_3$, and —$SF_5$; and
X is halogen.

25. The compound according to any one of the preceding items, wherein
$R^9$ is —C(H)— or —N—;
$R^{10}$ is H or halogen;
$R^{11}$ is H or halogen;
$R^{12}$ is —$CX_3$, —$OCX_3$, H or halogen; and
X is halogen.

26. The compound according to any one of the preceding items, wherein —$R^2$—$R^1$ is —$R^{14}$, and $R^{14}$ is selected from the group consisting of —C(O)—$C_{1-8}$ alkyl; —C(O)—O—$C_{1-8}$ alkyl; —$C_{2-8}$ alkyl; —H and —S(O)$_2$—$C_{1-8}$ alkyl.

27. The compound according to any one of the preceding items, wherein the compound is the (S)-enantiomer.

28. The compound according to any one of the preceding items, wherein $R^1$ is —$OC_{1-8}$ alkyl, such as —$OC_{1-7}$ alkyl, such as —$OC_{1-6}$ alkyl, such as —$OC_{1-5}$ alkyl, such as —$OC_{14}$ alkyl, such as —$OC_{1-3}$ alkyl, such as —$OC_{1-2}$ alkyl, such as —$OC_1$ alkyl.

29. The compound according to any one of the preceding items, wherein $R^1$ is —$C_{1-8}$ alkyl, such as —$C_{1-7}$ alkyl, such as —$C_{1-6}$ alkyl, such as —$C_{1-5}$ alkyl, such as —$C_{1-4}$ alkyl, such as —$C_{1-3}$ alkyl, such as —$C_{1-2}$ alkyl, such as —$C_1$ alkyl.

30. The compound according to any one of the preceding items, wherein $R^1$ is —$C_{1-8}$ alkyl substituted with —OH.

31. The compound according to any one of the preceding items, wherein $R^1$ is —H.

32. The compound according to any one of the preceding items, wherein $R^2$ is a bond.

33. The compound according to any one of the preceding items, wherein $R^2$ is —C(O)—.

34. The compound according to any one of the preceding items, wherein $R^2$ is —C(H)$_2$—.

35. The compound according to any one of the preceding items, wherein $R^2$ is —S(O)$_2$—.

36. The compound according to any one of the preceding items, wherein $R^2$ is —C(O)— and $R^1$ is —$OC_{1-4}$ alkyl.

37. The compound according to any one of the preceding items, wherein $R^2$ is —C(O)— and $R^1$ is —$OC_{1-3}$ alkyl.

38. The compound according to any one of the preceding items, wherein $R^2$ is a bond and $R^1$ is $C_{3-4}$ alkyl.

39. The compound according to any one of the preceding items, wherein $R^{14}$ is —C(O)—$C_{1-8}$ alkyl, such as $R^{14}$ is —C(O)—$C_{1-3}$ alkyl, such as $R^{14}$ is —C(O)—$C_3$ alkyl, such as —C(O)-cyclopropyl.

40. The compound according to any one of the preceding items, wherein $R^{14}$ is —C(O)—O—$C_{1-8}$ alkyl, such as, $R^{14}$ is —C(O)—$OC_{1-3}$ alkyl, such as $R^{14}$ is selected from the group consisting of —C(O)—$OCH_3$, —C(O)—$OCH_2CH_3$, —$OCH_2(CH_3)_2$ and —O— cyclopropyl.

41. The compound according to any one of the preceding items, wherein $R^{14}$ is —$C_{2-8}$ alkyl, such as $C_{3-4}$ alkyl.

42. The compound according to any one of the preceding items, wherein $R^{14}$ is —C(H)$_2$—$C_{3-7}$ cycloalkyl, such as —C(H)$_2$-cyclopropyl or —C(H)$_2$-cyclobutyl. In one 43. The compound according to any one of the preceding items, wherein $R^{14}$ is —$C_{3-7}$ cycloalkyl, such as -cyclopropyl or -cyclobutyl.

44. The compound according to any one of the preceding items, wherein $R^{14}$ is —$C_{2-8}$ alkyl, such as $C_{3-4}$ alkyl, substituted with one or more —OH, such as $R^{14}$ is isopropyl substituted with —OH.

45. The compound according to any one of the preceding items, wherein $R^{14}$ is —H.

46. The compound according to any one of the preceding items, wherein $R^{14}$ is —S(O)$_2$—$C_{1-8}$ alkyl, such as $R^{14}$ is —S(O)$_2$—$CH_3$.

47. The compound according to any one of the preceding items, wherein $R^{14}$ is not —$CH_3$.

48. The compound according to any one of the preceding items, wherein $R^3$ is $C_{1-5}$ alkyl, such as $C_{1-4}$ alkyl, such as $C_{1-3}$ alkyl, such as $C_{1-2}$ alkyl, such as $C_1$ alkyl.

49. The compound according to any one of the preceding items, wherein $R^4$ is $C_{1-5}$ alkyl, such as $C_{1-4}$ alkyl, such as $C_{1-3}$ alkyl, such as $C_{1-2}$ alkyl, such as $C_1$ alkyl.

50. The compound according to any one of the preceding items, wherein $R^3$ and $R^4$ are H.

51. The compound according to any one of the preceding items, wherein $R^5$ is $C_{1-8}$ alkyl, such as $C_{1-7}$ alkyl, such as $C_{1-6}$ alkyl, such as $C_{1-5}$ alkyl, such as $C_{1-4}$ alkyl, such as $C_{1-3}$ alkyl, such as $C_{1-2}$ alkyl, such as $C_1$ alkyl.

52. The compound according to any one of the preceding items, wherein $R^6$ is $C_{1-8}$ alkyl, such as $C_{1-7}$ alkyl, such as $C_{1-6}$ alkyl, such as $C_{1-5}$ alkyl, such as $C_{1-4}$ alkyl, such as $C_{1-3}$ alkyl, such as $C_{1-2}$ alkyl, such as $C_1$ alkyl.

53. The compound according to any one of the preceding items, wherein $R^5$ and $R^6$ are H.

54. The compound according to any one of the preceding items, wherein $R^5$ and $R^6$ are —$CH_3$.

55. The compound according to any one of the preceding items, wherein $R^5$ and $R^6$ are linked together to form a ring.

56. The compound according to any one of the preceding items, wherein $R^7$ is $C_{1-8}$ alkyl, such as $C_{1-7}$ alkyl, such as $C_{1-6}$ alkyl, such as $C_{1-5}$ alkyl, such as $C_{1-4}$ alkyl, such as $C_{1-3}$ alkyl, such as $C_{1-2}$ alkyl, such as $C_1$ alkyl.

57. The compound according to any one of the preceding items, wherein $R^7$ is H.

58. The compound according to any one of the preceding items, wherein R is —C(O)—O—$CH_3$ or —C(O)—$CH_3$.

59. The compound according to any one of the preceding items, wherein $R^8$ is $C_{1-8}$ alkyl, such as $C_{1-7}$ alkyl, such as $C_{1-6}$ alkyl, such as $C_{1-5}$ alkyl, such as $C_{1-4}$ alkyl, such as $C_{1-3}$ alkyl, such as $C_{1-2}$ alkyl, such as $C_1$ alkyl.

60. The compound according to any one of the preceding items, wherein $R^8$ is H.

61. The compound according to any one of the preceding items, wherein $R^5$ or $R^6$ is linked to $R^7$ or $R^8$ to form a ring, such as $R^5$ is linked to $R^7$.

62. The compound according to any one of the preceding items, wherein $R^5$ is linked to $R^7$ to form a four-, five- or six membered ring.

63. The compound according to any one of the preceding items, wherein $R^3$ or $R^4$ is linked to $R^5$ or $R^6$ to form a ring, such as $R^3$ is linked to $R^5$.

64. The compound for use according to any one of the preceding items, wherein $R^3$ is linked to $R^5$ to form a four or five membered ring.

65. The compound according to any one of the preceding items, wherein $R^3$ or $R^4$ is linked together to $R^7$ or $R^8$ to form a ring, such as $R^3$ is linked to $R^7$.

66. The compound for use according to any one of the preceding items, wherein $R^3$ is linked to $R^7$ to form a four membered ring.

67. The compound according to any one of the preceding items, wherein $R^9$ is —C(H)—.

68. The compound according to any one of the preceding items, wherein $R^{10}$ is H.

69. The compound according to any one of the preceding items, wherein $R^{10}$ is Cl.

70. The compound according to any one of the preceding items, wherein $R^{11}$ is F.

71. The compound according to any one of the preceding items, wherein $R^{12}$ is —$CF_3$.

72. The compound according to any one of the preceding items, wherein $R^{12}$ is —$OCF_3$.

73. The compound according to any one of the preceding items, wherein $R^{12}$ is Cl or Br.

74. The compound according to any one of the preceding items, wherein $R^{11}$ is F and $R^{12}$ is —$CF_3$.

75. The compound according to any one of the preceding items, wherein $R^9$ is —C(H)—, $R^{10}$ is H, $R^{11}$ is F and $R^{12}$ is —$CF_3$ or —$OCF_3$.

76. The compound according to any one of the preceding items, wherein $R^9$ is —C(H)—, $R^{10}$ is H, $R^{11}$ is F and $R^{12}$ is —CF$_3$.

77. The compound according to any one of the preceding items, wherein $R^9$ is —C(H)—, $R^{10}$ is H, $R^{11}$ is F and $R^{12}$ is —OCF$_3$.

78. The compound according to any one of the preceding items, wherein —$R^1$-$R^2$ is not —CH$_3$.

79. The compound according to any one of the preceding items, wherein no more than two of $R^{10}$, $R^{11}$ and $R^{12}$ are H.

80. The compound according to any one of the preceding items, wherein no more than one of $R^{10}$, $R^{11}$ and $R^{12}$ are H.

81. The compound according to any one of the preceding items, wherein when $R^{11}$ and $R^2$ are H, then $R^{10}$ is halogen.

82. The compound according to any one of the preceding items, wherein no more than five of $R^3$, $R^4$, $R^5$, $R^6$, $R^7$ and $R^8$ are H.

83. The compound according to any one of the preceding items, wherein when $R^3$, $R^4$, $R^5$, $R^6$, $R^7$ and $R^8$ are H, then no more than two of $R^{10}$, $R^{11}$ and $R^{12}$ are H.

84. The compound according to any one of the preceding items, wherein the compound is not selected from the group consisting of
N1-[1-(3-chlorophenyl)cyclopropyl]-N1-methyl-1,2-ethanediamine;
N1-[1-(3-fluorophenyl)cyclopropyl]-N1-methyl-1,2-ethanediamine;
N1-[1-(4-bromophenyl)cyclopropyl]-N1-methyl-1,2-ethanediamine;
N1-[1-(4-fluorophenyl)cyclopropyl]-N1-methyl-1,2-ethanediamine;
N1-methyl-N1-(i-phenylcyclopropyl)-1,2-ethanediamine;
N-[1-(4-fluorophenyl)cyclopropyl]-N-methyl-3-azetidinamine;
N-[1-(4-fluorophenyl)cyclopropyl]-N-methyl-3-pyrrolidinamine;
N-[1-(3-fluorophenyl)cyclopropyl]-N-methyl-3-pyrrolidinamine;
N-[1-(3-fluorophenyl)cyclopropyl]-N-methyl-3-azetidinamine;
N-methyl-N-(1-phenylcyclopropyl)-3-pyrrolidinamine;
N-methyl-N-(1-phenylcyclopropyl)-3-azetidinamine;
N-methyl-N-(1-phenylcyclopropyl)-3-piperidinamine;
N-[1-(4-chlorophenyl)cyclopropyl]-N-methyl-3-azetidinamine;
N-[1-(3-chlorophenyl)cyclopropyl]-N-methyl-3-azetidinamine; and
N1-[1-(3-bromophenyl)cyclopropyl]-N1-methyl-1,2-ethanediamine.

85. The compound according to any one of the preceding items, wherein the compound is selected from the group consisting of:
Methyl N-(2-(dimethylamino)ethyl)-N-(1-(4-fluoro-3-(trifluoromethyl)phenyl)cyclopropyl) carbamate;
Methyl (2-amino-2-methylpropyl)(1-(4-fluoro-3-(trifluoromethyl)phenyl)cyclopropyl)carbamate;
Methyl ((1-aminocyclopropyl)methyl)(1-(4-fluoro-3-(trifluoromethyl)phenyl)cyclopropyl) carbamate;
Methyl 3-((1-(4-fluoro-3-(trifluoromethyl) phenyl) cyclopropyl) (methoxycarbonyl)amino)azetidine-1-carboxylate;
Methyl azetidin-3-yl(1-(4-fluoro-3-(trifluoromethyl)phenyl) cyclopropyl)carbamate;
N-(cyclopropylmethyl)-N-(1-(4-fluoro-3-(trifluoromethyl) phenyl)cyclopropyl)azetidin-3-amine;
Methyl (2-aminoethyl)(1-(4-fluoro-3-(trifluoromethyl)phenyl)cyclopropyl)carbamate;
N1-(cyclopropyl methyl)-N1-(1-(4-fluoro-3-(trifluoromethyl)phenyl)cyclopropyl)-2-methyl propane-1,2-diamine;
N-(2-amino-2-methylpropyl)-N-(1-(4-fluoro-3-(trifluoromethyl)phenyl)cyclopropyl)cyclopropanecarboxamide;
N1-cyclopropyl-2-methyl-N1-(1-(3-(trifluoromethyl)phenyl)cyclopropyl)propane-1,2-diamine;
Methyl (2-amino-2-methylpropyl)(1-(3,5-dichlorophenyl) cyclopropyl)carbamate;
Methyl (2-amino-2-methylpropyl)(1-(3-bromophenyl)cyclopropyl)carbamate;
Methyl (2-amino-2-methylpropyl)(1-(3-chlorophenyl)cyclopropyl)carbamate;
1-((azetidin-2-ylmethyl)(1-(4-fluoro-3-(trifluoromethyl) phenyl)cyclopropyl)amino)-2-methyl propan-2-ol;
Methyl (2-amino-2-methylpropyl)(1-(3-(trifluoromethyl) phenyl)cyclopropyl)carbamate;
1-((1-(4-fluoro-3-(trifluoromethyl)phenyl)cyclopropyl)((1-methylazetidin-2-yl)methyl)amino)-2-methylpropan-2-ol;
Methyl (2-amino-2-methylpropyl)(1-(5-fluoro-4-(trifluoromethyl)pyridin-2-yl)cyclopropyl) carbamate;
N1-cyclobutyl-2-methyl-N1-(1-(3-(trifluoromethyl)phenyl) cyclopropyl)propane-1,2-diamine;
Ethyl (2-amino-2-methylpropyl)(1-(4-fluoro-3-(trifluoromethyl)phenyl)cyclopropyl)carbamate;
Methyl (2-amino-2-methylpropyl)(1-(4-fluoro-3-(trifluoromethoxy)phenyl)cyclopropyl)carbamate;
N-(2-amino-2-methylpropyl)-N-(1-(4-fluoro-3-(trifluoromethyl)phenyl)cyclopropyl)methanesulfonamide;
Methyl (R)-(1-(4-fluoro-3-(trifluoromethyl)phenyl)cyclopropyl)(pyrrolidin-2-ylmethyl)carbamate;
Methyl (S)-(1-(4-fluoro-3-(trifluoromethyl)phenyl)cyclopropyl)(pyrrolidin-2-ylmethyl)carbamate;
Methyl (2-acetamido-2-methylpropyl)(1-(4-fluoro-3-(trifluoromethyl)phenyl)cyclopropyl)carbamate;
N1-(1-(4-fluoro-3-(trifluoromethyl)phenyl) cyclopropyl)-2-methylpropane-1,2-diamine;
Methyl (azetidin-2-ylmethyl)(1-(4-fluoro-3-(trifluoromethyl)phenyl)cyclopropyl)carbamate;
Methyl (S)-(1-(4-fluoro-3-(trifluoro methyl) phenyl)cyclopropyl)((1-methylpyrrolidin-2-yl)methyl) carbamate;
Methyl (S)-(1-(4-fluoro-3-(trifluoromethoxy)phenyl)cyclopropyl)(pyrrolidin-2-ylmethyl)carbamate;
Methyl (R)-(1-(4-fluoro-3-(trifluoromethoxy)phenyl)cyclopropyl)(pyrrolidin-2-ylmethyl)carbamate;
Methyl (1-(4-fluoro-3-(trifluoromethyl)phenyl)cyclopropyl) ((1-methylazetidin-2-yl)methyl)carbamate;
Methyl (R)-(1-(4-fluoro-3-(trifluoromethyl)phenyl)cyclopropyl)((1-methylpyrrolidin-2-yl)methyl)carbamate;
Methyl (azetidin-2-ylmethyl)(1-(4-fluoro-3-(trifluoromethoxy)phenyl)cyclopropyl)carbamate;
Methyl (1-(4-fluoro-3-(trifluoromethyl)phenyl)cyclopropyl) (2-(hydroxyamino)-2-methylpropyl)carbamate;
Ethyl (S)-(1-(4-fluoro-3-(trifluoromethyl)phenyl)cyclopropyl)(pyrrolidin-2-ylmethyl)carbamate:
Ethyl (S)-(1-(4-fluoro-3-(trifluoromethyl)phenyl)cyclopropyl)((1-methylpyrrolidin-2-yl)methyl) carbamate;
(S)—N-(1-(4-fluoro-3-(trifluoromethyl)phenyl)cyclopropyl)-N-(pyrrolidin-2-ylmethyl) methanesulfonamide;
(S)—N-(1-(4-fluoro-3-(trifluoromethyl)phenyl)cyclopropyl)-N-((1-methylpyrrolidin-2-yl)methyl)methanesulfonamide;
Ethyl (R)-(1-(4-fluoro-3-(trifluoromethyl)phenyl)cyclopropyl)(pyrrolidin-2-ylmethyl)carbamate;
Methyl (R)-(1-(4-fluoro-3-(trifluoromethyl)phenyl)cyclopropyl)(morpholin-3-ylmethyl) carbamate;

Methyl (R)-(1-(4-fluoro-3-(trifluoromethyl)phenyl)cyclopropyl)((4-methylmorpholin-3-yl)methyl)carbamate;
(R)—N-(1-(4-fluoro-3-(trifluoromethyl)phenyl)cyclopropyl)-N-(pyrrolidin-2-ylmethyl) methane sulphonamide;
Methyl (S)-(1-(4-fluoro-3-(trifluoromethyl)phenyl)cyclopropyl)(morpholin-3-ylmethyl) carbamate;
Methyl (S)-(1-(4-fluoro-3-(trifluoromethyl)phenyl)cyclopropyl)((4-methylmorpholin-3-yl)methyl)carbamate;
Isopropyl (S)-(1-(4-fluoro-3-(trifluoromethyl)phenyl)cyclopropyl)(pyrrolidin-2-ylmethyl)carbamate;
Cyclopropyl (S)-(1-(4-fluoro-3-(trifluoromethyl)phenyl)cyclopropyl)(pyrrolidin-2-ylmethyl)carbamate;
Methyl (R)-(1-(4-fluoro-3-(trifluoromethyl)phenyl)cyclopropyl)((2-methyl pyrrolidin-2-yl)methyl)carbamate;
N-((1-amino cyclopropyl)methyl)-1-(4-fluoro-3-(trifluoromethyl)phenyl)cyclopropan-1-amine;
Cyclopropylmethyl (S)-(1-(4-fluoro-3-(trifluoromethyl)phenyl)cyclopropyl)(pyrrolidin-2-ylmethyl)carbamate;
N-((1-aminocyclopropyl)methyl)-N-(1-(4-fluoro-3-(trifluoromethyl)-phenyl)cyclopropyl)methanesulfonamide;
Methyl (S)-(1-(4-fluoro-3-(trifluoromethyl)phenyl)cyclopropyl)((2-methylpyrrolidin-2-yl)methyl)carbamate;
(1S, 2S)—N1-(1-(4-fluoro-3-(trifluoromethyl)phenyl)cyclopropyl)-cyclopentane-1,2-diamine;
(1R,2S)—N1-(1-(4-fluoro-3-(trifluoromethyl)phenyl)cyclopropyl)-cyclopentane-1,2-diamine; and
Methyl (S)-(azetidin-2-ylmethyl)(1-(4-fluoro-3-(trifluoromethyl)phenyl)-cyclopropyl)carbamate.

86. A pharmaceutical composition comprising the compound according to any one of the preceding items.

87. The compound or pharmaceutical composition according to any one of the preceding items for use in medicine.

88. The compound according to any one of items 1 to 50 or pharmaceutical composition according to item 51 for use in the treatment of inflammatory bowel disease (IBD).

89. The compound or pharmaceutical composition for use according to item 88, wherein the IBD is colitis.

90. The compound or pharmaceutical composition for use according to item 88, wherein the IBD is ulcerative colitis.

91. The compound or pharmaceutical composition for use according to item 88, wherein the IBD is Crohn's disease.

92. The compound according to any one of items 1 to 85 or pharmaceutical composition according to item 86 for use in the treatment of hereditary xerocytosis.

93. The compound according to any one of items 1 to 85 or pharmaceutical composition according to item 86 for use in the treatment of acute respiratory distress syndrome (ARDS).

94. A method for treatment of IBD, hereditary xerocytosis or ARDS comprising administration of the compound defined in any one of items 1 to 85 or a composition according to item 86 to a subject in need thereof.

95. Use of the compound defined in any one of items 1 to 85 or the composition according to item 86 in the manufacture of a medicament for treatment of IBD, hereditary xerocytosis or ARDS.

EXAMPLES

Example [1]—Methyl N-(2-(dimethylamino)ethyl)-N-(1-(4-fluoro-3-(trifluoromethyl)phenyl)cyclopropyl) carbamate Step 1
To a solution of the 4-fluoro-3-(trifluoromethyl)benzonitrile (105.75 mmol) and titanium(IV)isopropoxide (116.33 mmol) in dry diethyl ether was added ethylmagnesium bromide 3M solution in Ether (222.09 mmol) at −78° C. The resulting yellow solution was stirred for 10 minutes and slowly warmed to rt over 4 h. Then boron trifluoride diethyl etherate (211.51 mmol) was added and the reaction mixture was stirred for 24 h at rt. The reaction mixture was quenched with 1.5 N HCl solution and extracted with ethyl acetate. The aqueous phase was basified with 10% sodium hydroxide solution and extracted with ethyl acetate. The organic layer was washed with brine and dried over anhydrous sodium sulphate to obtain crude which was purified by flash chromatography using neutral silica gel in 10% TEA in ethyl acetate: Pet-ether as eluent to afford 1-(4-fluoro-3-(trifluoromethyl)phenyl)cyclopropane-1-amine [1.1] (LCMS: MH+: 220.1) as product.

Step 2
To a stirred solution of 1-(4-fluoro-3-(trifluoromethyl)phenyl)cyclopropan-1-amine [1.1] (0.2 g, 0.912 mmol) in dichloromethane (10 mL) was added N,N-diisopropylethylamine (0.35 mL, 2 mmol) followed by methyl chloroformate (0.122 g, 1.29 mmol) at 0° C. and the reaction mixture was stirred at rt for 2 h. The reaction mixture was quenched with water and extracted with ethyl acetate. The organic layer was washed with brine solution and dried over sodium sulphate, filtered and concentrated under reduced pressure to afford the crude product which was purified by flash chromatography using ethyl acetate in hexanes as eluent to afford methyl (1-(4-fluoro-3-(trifluoromethyl)phenyl)cyclopropyl) carbamate [1.2] as an off white solid (0.19 g, 75%).

Step 3
To a solution of methyl (1-(4-fluoro-3-(trifluoromethyl)phenyl)cyclopropyl)carbamate [1.2] (0.08 g, 0.29 mmol) in DMF (3 mL) was added sodium hydride (60%, 0.016 g, 0.32 mmol). The reaction was stirred at 0° C. for 10 minutes then, 2-chloro-N,N-dimethylethan-1-amine hydrochloride (0.037 g, 0.26 mmol) added and the reaction stirred at rt for 1 h. The reaction mixture was poured into ice and extracted with ethyl acetate. The organic layer was washed with brine solution, dried over sodium sulphate, filtered and concentrated under reduced pressure to afford the crude product, which was purified by column chromatography using ethyl acetate in hexane to afford methyl (2-(dimethylamino)ethyl) (1-(4-fluoro-3-(trifluoromethyl)phenyl)cyclopropyl) carbamate [1] as yellow gum (0.012 g, 15%). $^1$H-NMR (400 MHz, DMSO-$d_6$): δ 7.55 (bs, 1H), 7.45-7.35 (m, 2H), 3.55 (bs, 3H), 3.40-3.30 (m, 2H), 1.70 (bs, 2H), 2.05 (s, 6H), 1.48-1.18 (m, 4H). HRMS calculated for: $[C_{16}H_{20}F_4N_2O_2+H]+$349.1534; found: 349.1526 (deviation 2.3).

Example [2]—Methyl (2-amino-2-methylpropyl)(1-(4-fluoro-3-(trifluoromethyl)phenyl)cyclopropyl) carbamate Step 1
To a solution of tert-butyl (1-hydroxy-2-methylpropan-2-yl)carbamate (20 g, 105.7 mmol) in dichloromethane (100 mL) was added Dess-Martin periodinane (55.4 g, 126.8 mmol) at 0° C. and stirred at room temperature for 16 h. The reaction mixture was filtered and the filtrate was extracted with dichloromethane, washed with saturated sodium thiosulphate solution and 10% sodium bicarbonate solution. The organic layer was dried over sodium sulphate, filtered and dried under vacuum to afford crude product, which was purified by flash chromatography using ethyl acetate in pet-ether as solvent to afford tert-butyl (2-methyl-1-oxopropan-2-yl)carbamate [2.1] as a white solid (19.5 g, 99%).

Step 2

To a stirred solution of 1-(4-fluoro-3-(trifluoromethyl) phenyl)cyclopropan-1-amine [1.1] (0.05 g, 0.22 mmol) in IPA (5 mL) at 0° C. was added tert-butyl (2-methyl-1-oxopropan-2-yl)carbamate [2.1] (0.029 g, 0.16 mmol) and acetic acid (0.05 mL). The reaction was stirred for 1 h at room temperature, then sodium cyanoborohydride (0.016 g, 0.26 mmol) was added at 0° C., then the reaction stirred at room temperature for 2 h. Saturated aq. sodium bicarbonate solution was added and the reaction extracted with DCM. The combined organic layers were washed with brine solution, dried over sodium sulfate, filtered and concentrated in vacuo to afford the crude product which was purified by column chromatography using EtOAc in hexane as eluent to afford tert-butyl (1-(((1-(4-fluoro-3-(trifluoromethyl)phenyl) cyclopropyl)amino)-2-methylpropan-2-yl)carbamate [2.2] as a colourless liquid (0.03 g, 34%, LCMS MH$^+$=391.1).

Step 3

The procedure used in Example [1], Step 2 was adapted such that 16 g of tert-butyl (1-(((1-(4-fluoro-3-(trifluoromethyl)phenyl)cyclopropyl)amino)-2-methylpropan-2-yl)carbamate [2.2] was reacted to afford methyl (2-((tert-butoxycarbonyl)amino)-2-methylpropyl)(1-(4-fluoro-3-(trifluoromethyl)phenyl)cyclopropyl)carbamate [2.3] (14 g, 76%, LCMS MH$^+$=449.2).

Step 4

To a stirred solution of methyl (2-((tert-butoxycarbonyl)amino)-2-methylpropyl)(1-(4-fluoro-3-(trifluoromethyl)phenyl)cyclopropyl)carbamate [2.3] (7.8 g, 17.4 mmol) in dioxane (10 mL) was added dioxane. HCl (20 mL) at 0° C. and the reaction stirred at room temperature for 12 h. The reaction was concentrated under reduced pressure and the residue triturated in pentane to afford methyl (2-amino-2-methylpropyl)(1-(4-fluoro-3-(trifluoromethyl)phenyl)cyclopropyl)carbamate [2]hydrochloride salt as an off-white solid (6.5 g, 97%). $^1$H-NMR (400 MHz, DMSO-d$_6$): δ 7.53 (s, 2H), 7.42 (t, J=10.40 Hz, 1H), 3.57 (s, 3H), 3.32 (d, J=16.80 Hz, 2H), 1.65 (bs, 4H), 1.31 (s, 2H), 0.93 (s, 6H). HRMS calculated for: [C$_{16}$H$_{20}$F$_4$N2O2+H]+349.1534; found: 349.1521 (deviation 3.7 ppm).

Example [3]—Methyl ((1-aminocyclopropyl) methyl)(1-(4-fluoro-3-(trifluoromethyl)phenyl)cyclopropyl) carbamate Step 1

To a solution of 1-(4-fluoro-3-(trifluoromethyl)phenyl) cyclopropan-1-amine [1.1] (0.2 g, 0.91 mmol) and 0.16 g of tert-butyl N-(1-formylcyclopropyl)carbamate (0.16 g, 0.91 mmol) in dichloromethane/isopropyl alcohol (3:2, 10 mL) was added sodium triacetoxy borohydride (0.38 g, 1.82 mmol) at room temperature and the reaction stirred for 2 h. The reaction mixture was diluted with water and extracted with DCM. The organic layer was washed with brine solution and dried over sodium sulphate, filtered and concentrated under reduced pressure to afford crude product, which was purified by flash chromatography using ethyl acetate in pet-ether as solvent system to afford tert-butyl (1-(((1-(4-fluoro-3-(trifluoromethyl)phenyl)cyclopropyl)amino) methyl)cyclopropyl)carbamate [3.1] as an off white solid (0.11 g, 31%, LCMS MH$^+$=389.2).

Step 2

The procedure used in Example [1], Step 2 was adapted such that 0.11 g of tert-butyl (1-(((1-(4-fluoro-3-(trifluoromethyl)phenyl)cyclopropyl)amino)methyl)cyclopropyl)carbamate [3.1] and 0.073 g of methyl chloroformate was reacted to afford the product methyl ((1-(((tert-butoxycarbonyl)amino)cyclopropyl)methyl)(1-(4-fluoro-3-(trifluoromethyl)phenyl)cyclopropyl)carbamate [3.2] as an off white solid (0.1 g, 80%, LCMS MH$^+$=447.2).

Step 3

The procedure used in Example [2], Step 4 was adapted such that 0.1 g of methyl ((1-((tert-butoxycarbonyl)amino) cyclopropyl)methyl)(1-(4-fluoro-3-(trifluoromethyl)phenyl) cyclopropyl)carbamate [3.2] was reacted to afford methyl ((1-aminocyclopropyl)methyl)(1-(4-fluoro-3-(trifluoromethyl)phenyl)cyclopropyl) carbamate [3] as a a brown solid (0.055 g, 55%). $^1$H-NMR (400 MHz, DMSO-d$_6$): δ 7.60-7.32 (m, 4H), 3.65 (s, 3H), 1.60-1.42 (m, 2H), 1.36-1.28 (m, 2H), 1.30-1.21 (m, 2H), 0.95-0.70 (m, 5H). HRMS calculated for: [C$_{16}$H$_{18}$F$_4$N2O2+H]$^+$347.1377; found: 347.1369 (deviation 2.5 ppm).

Example [4]—Methyl 3-((1-(4-fluoro-3-(trifluoromethyl) phenyl) cyclopropyl)(methoxycarbonyl) amino)azetidine-1-carboxylate Step 1

The procedure used in Example [3], Step 1 was adapted such that 0.5 g of 1-(4-fluoro-3-(trifluoromethyl)phenyl) cyclopropan-1-amine and 0.117 g of tert-butyl 3-oxoazetidine-1-carboxylate were reacted to afford the product tert-butyl 3-((1-(4-fluoro-3-(trifluoromethyl)phenyl) cyclopropyl)amino)azetidine-1-carboxylate [4.1] (0.39 g, crude, LCMS MH$^+$=375.1).

Step 2

The procedure used in Example [2], Step 4 was adapted such that 0.3 g of tert-butyl 3-((1-(4-fluoro-3-(trifluoromethyl)phenyl)cyclopropyl)amino)azetidine-1-carboxylate [4.1] was reacted to afford the product N-(1-(4-fluoro-3-(trifluoromethyl)phenyl)cyclopropyl) azetidin-3-amine [4.2] (0.2 g, crude, LCMS MH$^+$=275.1).

Step 3

The procedure used in Example [1], Step 2 was adapted such that 0.2 g of N-(1-(4-fluoro-3-(trifluoromethyl)phenyl) cyclopropyl)azetidin-3-amine and 0.2 mL of methyl carbonochloridate were reacted to afford methyl 3-((1-(4-fluoro-3-(trifluoromethyl)phenyl) cyclopropyl) (methoxycarbonyl)amino)azetidine-1-carboxylate [4] (0.045 g, 30%). MS (M+1)$^+$=391.1. $^1$H-NMR (400 MHz, DMSO-d$_6$): δ 7.45 (t, J=8.80 Hz, 2H), 7.30 (d, J=5.20 Hz, 1H), 4.40 (q, J=6.80 Hz, 1H), 4.20-3.98 (m, 4H), 3.61 (s, 3H), 3.52 (s, 3H), 1.40 (s, 4H). HRMS calculated for: [C$_{17}$H$_{18}$F$_4$N2O4+H]+391.1275; found: 391.1264 (deviation 2.8 ppm).

Example [5]—Methyl azetidin-3-yl(1-(4-fluoro-3-(trifluoromethyl)phenyl)cyclopropyl)carbamate Step 1

The procedure used in Example [1], Step 2 was adapted such that 0.3 g of tert-butyl 3-((1-(4-fluoro-3-(trifluoromethyl)phenyl)cyclopropyl)amino)azetidine-1-carboxylate [4.1] and 0.226 g of methyl carbonochloridate were reacted to afford the product tert-butyl 3-((1-(4-fluoro-3-(trifluoromethyl)phenyl)cyclopropyl)(methoxycarbonyl)amino) azetidine-1-carboxylate [5.1] (0.3 g, crude, LCMS MH$^+$=433.1).

Step 2

The procedure used in Example [2], Step 4 was adapted such that 0.25 g of tert-butyl 3-((1-(4-fluoro-3-(trifluoromethyl)phenyl)cyclopropyl)(methoxy carbonyl)amino)azetidine-1-carboxylate [5.1] was reacted to afford methyl azetidin-3-yl(1-(4-fluoro-3-(trifluoromethyl)phenyl)

cyclopropyl)carbamate [5] (0.04 g, 40%). MS (M+1)+= 333.1. $^1$H-NMR (400 MHz, CDCl$_3$): δ 7.32-7.27 (m, 2H), 7.15 (t, J=8.80 Hz, 1H), 4.60-4.50 (m, 1H), 4.50-4.20 (m, 4H), 3.82 (s, 3H), 1.32-1.25 (m, 4H). HRMS calculated for: [C$_{15}$H$_{16}$F$_4$N2O2+H]+333.1221; found: 333.1215 (deviation 1.6 ppm).

Example [6]—N-(cyclopropylmethyl)-N-(1-(4-fluoro-3-(trifluoromethyl)phenyl)cyclopropyl)azetidin-3-amine Step 1

The procedure used in Example [3], Step 1 was adapted such that 0.25 g of tert-butyl 3-((1-(4-fluoro-3-(trifluoromethyl)phenyl)cyclopropyl)amino)azetidine-1-carboxylate [4.1] and 0.274 g of cyclopropanecarbaldehyde was reacted to afford the product tert-butyl 3-((cyclopropylmethyl)(1-(4-fluoro-3-(trifluoromethyl)phenyl) cyclopropyl) amino)azetidine-1-carboxylate as colourless gum (0.15 g, crude, LCMS MH*=429.1).

Step 2

The procedure used in Example [2], Step 4 was adapted such that 0.15 g of tert-butyl 3-((cyclopropylmethyl)(1-(4-fluoro-3-(trifluoromethyl)phenyl)cyclopropyl)amino)azetidine-1-carboxylate [6.1] was reacted to afford N-(cyclopropylmethyl)-N-(1-(4-fluoro-3-(trifluoromethyl)phenyl) cyclopropyl)azetidin-3-amine [6] as colourless gum (0.1 g, 87%). MS (M+1)+=329.1. $^1$H-NMR (400 MHz, DMSO-d$_6$): δ 8.53 (s, 1H), 8.38 (s, 1H), 7.67-7.62 (m, 2H), 7.47 (t, J=8.80 Hz, 1H), 3.95-3.82 (m, 3H), 3.79 (t, J=8.00 Hz, 1H), 2.38-2.32 (m, 2H), 1.17 (q, J=42.00 Hz, 2H), 0.96 (q, J=11.60 Hz, 2H), 1.40-1.30 (m, 1H), 0.47-0.42 (m, 2H), 0.13 (q, J=3.20 Hz, 2H). HRMS calculated for: [C$_{17}$H$_{20}$F$_4$N$_2$+H]$^+$329.1635; found: 329.1624 (deviation 3.3 ppm).

Example [7]—Methyl (2-aminoethyl)(1-(4-fluoro-3-(trifluoromethyl)phenyl)cyclopropyl)carbamate Step 1

The procedure used in Example [3], Step 1 was adapted such that 0.4 g of 1-(4-fluoro-3-(trifluoromethyl)phenyl)cyclopropan-1-amine [1.1] and 0.29 g of tert-butyl (2-oxoethyl)carbamate was reacted to afford the product tert-butyl (2-((1-(4-fluoro-3-(trifluoromethyl)phenyl)cyclopropyl)amino)ethyl)carbamate [7.1] as an off white solid (0.4 g, 60%, LCMS MH$^+$=363.2).

Step 2

The procedure used in Example [1], Step 2 was adapted such that 0.4 g of tert-butyl (2-((1-(4-fluoro-3-(trifluoromethyl)phenyl)cyclopropyl)amino)ethyl)carbamate [7.1] and 0.32 g of methyl chloroformate was reacted to afford the product methyl (2-(((tert-butoxycarbonyl)amino)ethyl)(1-(4-fluoro-3-(trifluoromethyl)phenyl)cyclopropyl)carbamate [7.2] as an off white solid (0.4 g, crude, LCMS MH$^+$=421.2).

Step 3

The procedure used in Example [2], Step 4 was adapted such that 0.4 g methyl (2-(((tert-butoxycarbonyl)amino)ethyl)(1-(4-fluoro-3-(trifluoromethyl)phenyl)cyclopropyl) carbamate [7.2] was reacted to afford methyl (2-aminoethyl)(1-(4-fluoro-3-(trifluoromethyl)phenyl)cyclopropyl) carbamate [7] as a yellow oil (0.011 g, 04%). $^1$H-NMR (400 MHz, CDCl$_3$): δ 7.4 (bs, 3H), 3.72 (s, 3H), 3.40 (s, 2H), 2.82 (s, 2H), 1.45 (s, 2H), 1.25 (s, 4H). HRMS calculated for: [C$_{14}$H$_{16}$F$_4$N2O2+H]+321.1221; found: 321.1217 (deviation 1.1 ppm).

Example [8]—N1-(cyclopropyl methyl)-N1-(1-(4-fluoro-3-(trifluoromethyl)phenyl)cyclopropyl)-2-methyl propane-1,2-diamine Step 1

The procedure used in Example [3], Step 1 was adapted such that 0.22 g of tert-butyl (1-((1-(4-fluoro-3-(trifluoromethyl)phenyl)cyclopropyl)amino)-2-methyl propan-2-yl) carbamate and 0.047 g of cyclopropanecarbaldehyde was reacted to afford the product tert-butyl (1-((cyclopropylmethyl)(1-(4-fluoro-3-(trifluoromethyl)phenyl)cyclopropyl)amino)-2-methylpropan-2-yl)carbamate [8.1] as a colourless gum (0.2 g, 80%, LCMS MH$^+$=459.2).

Step 2

The procedure used in Example [2], Step 4 was adapted such that 0.2 g of tert-butyl (1-((cyclopropylmethyl)(1-(4-fluoro-3-(trifluoromethyl)phenyl)cyclopropyl)amino)-2-methylpropan-2-yl)carbamate [8.1] was reacted to afford N1-(cyclopropyl methyl)-N1-(1-(4-fluoro-3-(trifluoromethyl)phenyl)cyclopropyl)-2-methyl propane-1,2-diamine [8] as a yellow oil (0.1 g, 66%). $^1$H-NMR (400 MHz, DMSO-d$_6$): δ 7.70-7.60 (m, 2H), 7.45 (t, J=40.00 Hz, 1H), 2.52-2.40 (m, 2H), 2.37 (d, J=6.80 Hz, 2H), 1.40-1.20 (m, 4H), 1.10-1.00 (m, 2H), 1.00-0.88 (m, 7H), 0.45 (q, J=1.20 Hz, 2H), 0.07 (t, J=3.60 Hz, 2H). HRMS calculated for: [C$_{18}$H$_{24}$F$_4$N2+H]+345.1948; found: 345.1937 (deviation 3.3 ppm).

Example [9]—N-(2-amino-2-methylpropyl)-N-(1-(4-fluoro-3-(trifluoromethyl)phenyl)cyclopropyl) cyclopropanecarboxamide Step 1

To a stirred solution of tert-butyl (1-((1-(4-fluoro-3-(trifluoromethyl)phenyl)cyclopropyl)amino)-2-methyl propan-2-yl)carbamate [2.2] (0.1 g, 0.256 mmol) and DIPEA (0.09 mL, 0.512 mmol) in DCM (5 mL) was added cyclopropanecarbonyl chloride (0.054 g, 0.512 mmol) and the reaction stirred at room temperature for 18 h. The reaction was diluted with water and extracted with DCM. The combined organic layers were washed with brine solution, dried over sodium sulfate, filtered and concentrated under reduced pressure to afford tert-butyl (1-(N-(1-(4-fluoro-3-(trifluoromethyl)phenyl)cyclopropyl)cyclopropanecarboxamido)-2-methylpropan-2-yl)carbamate [9.1] as a colourless liquid (0.1 g, 80%, LCMS MH*=445.2).

Step 2

The procedure used in Example [2], Step 4 was adapted such that 0.1 g of tert-butyl (1-(N-(1-(4-fluoro-3-(trifluoromethyl)phenyl)cyclopropyl)cyclopropanecarboxamido)-2-methylpropan-2-yl)carbamate [9.1] was reacted to afford the crude product, which was purified by Prep HPLC using 0.2% TFA in acetonitrile to afford N-(2-amino-2-methylpropyl)-N-(1-(4-fluoro-3-(trifluoromethyl)phenyl)cyclopropyl) cyclopropanecarboxamide [9] as TFA salt as a pale brown solid (0.08 g, 80%). $^1$H-NMR (400 MHz, DMSO-d$_6$): δ 7.76 (s, 3H), 7.52 (t, J=11.60 Hz, 1H), 7.44-7.39 (m, 1H), 7.27 (dd, J=3.20, 8.40 Hz, 1H), 3.88 (d, J=60.00 Hz, 1H), 3.30 (s, 1H), 2.15-1.95 (m, 1H), 1.95-1.80 (m, 1H), 1.80-1.65 (m, 1H), 1.65-1.50 (m, 1H), 1.50-1.35 (m, 1H), 1.22 (s, 4H), (s, 3H), 0.90-0.80 (m, 2H), 0.80-0.65 (m, 1H), 0.65-0.55 (m, 1H). HRMS calculated for: [C$_{18}$H$_{22}$F$_4$N2O+H]+359.1741; found: 359.1733 (deviation 2.2 ppm).

Example [10]—N1-cyclopropyl-2-methyl-N1-(1-(3-(trifluoromethyl)phenyl)cyclopropyl)propane-1,2-diamine Step 1

The procedure used in Example [1], Step 1 was adapted such that 1.5 g of 3-(trifluoromethyl)benzonitrile was reacted to afford 1-(3-(trifluoromethyl)phenyl)cyclopropan-1-amine [10.1] (0.5 g, 30%, LCMS MH$^+$=202.1).

Step 2

The procedure used in Example [3], Step 1 was adapted such that 0.275 g of 1-(3-(trifluoromethyl)phenyl)cyclopropan-1-amine [10.1] was reacted to afford tert-butyl (2-methyl-1-((1-(3-(trifluoromethyl)phenyl)cyclopropyl)amino)propan-2-yl)carbamate [10.2] as an off-white solid (0.37 g, 73%, LCMS MH*=373.2).

Step 3

The procedure used in Example [2], Step 2 was adapted such that 0.270 g of tert-butyl (2-methyl-1-((1-(3-(trifluoromethyl)phenyl)cyclopropyl)amino)propan-2-yl)carbamate [2.2] was reacted with [(1-ethoxycyclopropyl)oxy]trimethylsilane to afford tert-butyl (1-(cyclopropyl(1-(3-(trifluoromethyl)phenyl)cyclopropyl)amino)-2-methylpropan-2-yl)carbamate [10.3] as an off-white gum (0.1 g, 36%, LCMS MH*=413.4).

Step 4

The procedure used in Example [2], Step 4 was adapted such that 0.06 g tert-butyl(1-(cyclopropyl(1-(3-(trifluoromethyl)phenyl)cyclopropyl)amino)-2-methylpropan-2-yl)carbamate [10.3] was reacted to afford N1-cyclopropyl-2-methyl-N1-(1-(3-(trifluoromethyl)phenyl)cyclopropyl)propane-1,2-diamine [10] as an off-white solid (0.025 g, 50%, LCMS MH$^+$=313.2). $^1$H-NMR (400 MHz, DMSO-d$_6$): δ 7.88 (s, 2H), 7.71-7.59 (m, 4H), 2.91 (s, 2H), 1.57 (m, 1H), 1.25 (d, J=5.68 Hz, 6H), 1.20-1.00 (m, 2H), 1.00-0.85 (m, 2H), 0.85-0.70 (m, 2H), 0.60-0.40 (m, 2H). HRMS calculated for: $[C_{17}H_{23}F_3N_2+H]$+313.1886; found: 313.1880 (deviation 2.1 ppm).

Example [11]—Methyl (2-amino-2-methylpropyl)(1-(3,5-dichlorophenyl)cyclopropyl)carbamate Step 1

The procedure used in Example [1], Step 1 was adapted such that 0.5 g of 3,5-dichlorobenzonitrile was reacted to afford 1-(3,5-dichlorophenyl)cyclopropan-1-amine [11.1] (0.2 g, 34%, LCMS MH$^+$=203.1).

Step 2

The procedure used in Example [3], Step 1 was adapted such that 0.2 g of 1-(3,5-dichlorophenyl)cyclopropan-1-amine [11.1] and 0.18 g of tert-butyl (2-methyl-1-oxopropan-2-yl)carbamate [2.1] was reacted to afford the product tert-butyl (1-((1-(3,5-dichlorophenyl)cyclopropyl)amino)-2-methylpropan-2-yl)carbamate [11.2] as a brown liquid (0.2 g, 54%, LCMS MH$^+$=374.1).

Step 3

The procedure used in Example [1], Step 2 was adapted such that 0.2 g of tert-butyl (1-((1-(3,5-dichlorophenyl)cyclopropyl)amino)-2-methylpropan-2-yl)carbamate [11.2] was reacted to afford the product methyl (2-((tert-butoxycarbonyl)amino)-2-methylpropyl)(1-(3,5-dichlorophenyl)cyclopropyl)carbamate [11.3] as colourless liquid (0.14 g, 60%, LCMS MH$^+$=432.2).

Step 4

The procedure used in Example [2], Step 4 was adapted such that 0.14 g of methyl (2-((tert-butoxycarbonyl)amino)-2-methylpropyl)(1-(3,5-dichlorophenyl)cyclopropyl)carbamate [11.3] was reacted to afford methyl (2-amino-2-methylpropyl)(1-(3,5-dichlorophenyl)cyclopropyl)carbamate [11] as an off-white solid (0.037 g, 31%). $^1$H-NMR (400 MHz, DMSO-d$_6$): δ 7.80 (bs, 3H), 7.48 (d, J=1.20 Hz, 1H), 7.14 (bs, 1H), 3.65 (s, 3H), 3.56 (d, J=2.40 Hz, 1H), 3.50 (s, 1H), 1.45 (s, 2H), 1.35 (s, 1H), 1.30-1.22 (m, 1H), 1.17 (bs, 6H). HRMS calculated for: $[C_{15}H_{20}C_{12}N_2O_2+H]$+331.0975; found: 331.0966 (deviation 2.7 ppm).

Example [12]—Methyl (2-amino-2-methylpropyl)(1-(3-bromophenyl)cyclopropyl)carbamate Step 1

The procedure used in Example [1], Step 1 was adapted such that 3 g of 3-bromobenzonitrile was reacted to afford 1-(3-bromophenyl)cyclopropan-1-amine [12.1](1.3 g, 56%, LCMS MH$^+$=213.0).

Step 2

The procedure used in Example [3], Step 1 was adapted such that 1 g of 1-(3-bromophenyl)cyclopropan-1-amine [12.1] and 0.97 g of tert-butyl (2-methyl-1-oxopropan-2-yl)carbamate [2.1] were reacted to afford the product tert-butyl (1-((1-(3-bromophenyl)cyclopropyl)amino)-2-methylpropan-2-yl)carbamate [2.2] as a yellow solid (0.9 g, 67%, LCMS MH$^+$=384.2).

Step 3

The procedure used in Example [1], Step 2 was adapted such that 0.5 g of tert-butyl (1-((1-(3-bromophenyl)cyclopropyl)amino)-2-methylpropan-2-yl)carbamate [2.2] was reacted to afford the product methyl (1-(3-bromophenyl)cyclopropyl)(2-((tert-butoxycarbonyl)amino)-2-methylpropyl)carbamate as a colourless liquid (0.4 g, 69%, LCMS MH$^+$=442.1).

Step 4

The procedure used in Example [2], Step 4 was adapted such that 0.1 g of methyl (1-(3-bromophenyl)cyclopropyl)(2-((tert-butoxycarbonyl)amino)-2-methylpropyl)carbamate [12.3] was reacted to afford methyl (2-amino-2-methylpropyl)(1-(3-bromophenyl)cyclopropyl)carbamate [12] as TFA salt (compound was purified by prep HPLC using 0.1% TFA in ACN) as a white solid (0.02 g, 26%). $^1$H-NMR (400 MHz, DMSO-d$_6$): δ 7.67 (bs, 2H), 7.42-7.38 (m, 1H), 7.27 (t, J=10.40 Hz, 2H), 7.10 (bs, 1H), 3.62 (s, 3H), 3.52-3.37 (m, 2H), 1.50-1.20 (m, 4H), 1.15 (s, 6H). HRMS calculated for: $[C_{15}H_{21}BrN_2O_2+H]$+341.0859; 343.0839; found: 341.0847; 343.0828 (deviation 3.5; 3.3 ppm).

Example [13]—Methyl (2-amino-2-methylpropyl)(1-(3-chlorophenyl)cyclopropyl)carbamate Step 1

The procedure used in Example [1], Step 1 was adapted such that 1 g of 3-bromobenzonitrile was reacted to afford 1-(3-chlorophenyl)cyclopropan-1-amine [13.1](0.4 g, 32%, LCMS MH$^+$=168.5).

Step 2

The procedure used in Example [3], Step 1 was adapted such that 0.4 g of 1-(3-chlorophenyl)cyclopropan-1-amine [13.1] and 0.49 g of tert-butyl (2-methyl-1-oxopropan-2-yl)carbamate [2.1] were reacted to afford the product tert-butyl (1-((1-(3-chlorophenyl)cyclopropyl)amino)-2-methylpropan-2-yl)carbamate [13.2] as a brown liquid (0.25 g, 31%, LCMS MH$^+$=339.2).

Step 3

The procedure used in Example [1], Step 2 was adapted such that 0.2 g of tert-butyl (1-((1-(3-chlorophenyl)cyclopropyl)amino)-2-methylpropan-2-yl)carbamate [13.2] was reacted to afford methyl (2-((tert-butoxycarbonyl)amino)-2-methylpropyl)(1-(3-chlorophenyl)cyclopropyl)carbamate [13.3] as a colourless liquid (0.17 g, 72%, LCMS MH+=397.1).

Step 4

The procedure used in Example [2], Step 4 was adapted such that 0.17 g of methyl (2-((tert-butoxycarbonyl)amino)-2-methylpropyl)(1-(3-chlorophenyl)cyclopropyl)carbamate [13.3] was reacted to afford methyl (2-amino-2-methylpropyl)(1-(3-chlorophenyl)cyclopropyl)carbamate [13] as TFA salt (compound was purified by Prep HPLC using 0.1% TFA in ACN) as a colourless gum (0.1 g, 78%). $^1$H-NMR (400 MHz, DMSO-d$_6$): δ 7.59 (s, 2H), 7.36-7.24 (m, 2H), 7.33 (bs, 2H), 3.62 (s, 3H), 3.50 (bs, 2H), 1.35 (s, 4H), 1.15 (s, 6H). HRMS calculated for: $[C_{15}H_{21}C_1N_2O_2+H]$+297.1364; found: 297.1257 (deviation 2.5 ppm).

Example [14]—1-((azetidin-2-ylmethyl)(1-(4-fluoro-3-(trifluoromethyl)phenyl)cyclopropyl) amino)-2-methyl propan-2-ol Step 1

To a stirred solution of 1-(4-fluoro-3-(trifluoromethyl)phenyl)cyclopropan-1-amine [1.1] (1.5 g, 6.84 mmol) and 1-(tert-butoxycarbonyl)azetidine-2-carboxylic acid (1.23 g, 6.15 mmol) in DMF was added Hatu (3.12 g, 8.21 mmol), followed by DIPEA (2.2 g, 17.10 mmol) at 0° C. and the reaction mixture was stirred at room temperature for 12 h. The reaction mixture was diluted with ethyl acetate, washed with water and brine solution. The organic layer was dried over sodium sulphate, filtered and concentrated under reduced pressure to afford a crude product, which was purified by flash chromatography using ethyl acetate in pet-ether as eluent to afford tert-butyl 2-((1-(4-fluoro-3-(trifluoromethyl)phenyl)cyclopropyl) carbamoyl) azetidine-1-carboxylate [14.1] as a colourless gum (2.3 g, 85%, LCMS MH+=403.3).

Step 2

To a solution of tert-butyl 2-((1-(4-fluoro-3-(trifluoromethyl)phenyl)cyclopropyl)carbamoyl)azetidine-1-carboxylate [14.1] (2.3 g, 5.72 mmol) in tetrahydrofuran was added borane dimethyl sulphide complex (1.8 g, 22.86 mmol) at 0° C. and the reaction refluxed at 70° C. for 2 h. The reaction mixture was quenched with methanol at 0° C. until the effervescence stopped. The reaction mixture was concentrated under reduced pressure and the residue was diluted with ethyl acetate washed with water and brine solution. The organic layer was dried over sodium sulphate, filtered and concentrated under reduced pressure to afford crude product, which was purified by flash chromatography using ethyl acetate in pet-ether as solvent to afford tert-butyl 2-(((1-(4-fluoro-3-(trifluoromethyl)phenyl)cyclopropyl)amino) methyl)azetidine-1-carboxylate [14.2] as colourless liquid (1.45 g, 55%, LCMS M+=389.4).

Step 3

To a solution of tert-butyl 2-(((1-(4-fluoro-3-(trifluoromethyl)phenyl)cyclopropyl)amino)methyl)azetidine-1-carboxylate [14.2] (0.3 g, 0.77 mmol) and potassium carbonate (0.32 g, 2.31 mmol) in acetonitrile was added methyl bromoacetate (0.35 g, 2.31 mmol) and the reaction mixture was heated at 80° C. for 12 h. The reaction mixture was concentrated under reduced pressure and the residue was diluted with ethyl acetate, washed with water and brine solution. The organic layer was dried over sodium sulphate, filtered and concentrated under reduced pressure to afford crude product, which was purified by flash chromatography using ethyl acetate in pet-ether as solvent to afford tert-butyl 2-(((1-(4-fluoro-3-(trifluoromethyl)phenyl)cyclopropyl)(2-methoxy-2-oxoethyl) amino)methyl)azetidine-1-carboxylate [14.3] as a colourless liquid. (0.25 g, 70%, LCMS MH+=461.2).

Step 4

To a stirred solution of tert-butyl 2-(((1-(4-fluoro-3-(trifluoromethyl)phenyl)cyclopropyl)(2-methoxy-2-oxoethyl) amino)methyl) azetidine-1-carboxylate [14.3](0.2 g, 0.43 mmol) in tetrahydrofuran (5 mL) at 0° C. was added methylmagnesium bromide (0.21 g, 1.74 mmol) at 0° C. and the reaction mixture was stirred at same temperature for 2 h, then stirred at rt for 1 h. The reaction mixture was quenched with aqueous ammonium chloride solution and extracted with ethyl acetate, washed with water and brine solution. The organic layer was dried over sodium sulphate, filtered and concentrated under reduced pressure to afford the crude product which was purified by column chromatography using ethyl acetate/hexane as eluent to afford tert-butyl 2-(((1-(4-fluoro-3-(trifluoromethyl)phenyl)cyclopropyl)(2-hydroxy-2-methylpropyl)amino) methyl)azetidine-1-carboxylate [14.4] as colourless gum (0.15 g, 75%, LCMS MH+=461.2).

Step 5

The procedure used in Example [1], Step 2 was adapted such that 0.12 g of tert-butyl 2-(((1-(4-fluoro-3-(trifluoromethyl)phenyl)cyclopropyl)(2-hydroxy-2-methylpropyl) amino)methyl)azetidine-1-carboxylate [14.4] was reacted to afford 1-((azetidin-2-ylmethyl)(1-(4-fluoro-3-(trifluoromethyl)phenyl)cyclopropyl)amino)-2-methyl propan-2-ol [14] as an off-white solid (0.06 g, 66%, LCMS MH+=361.2). $^1$H-NMR (400 MHz, CDCl$_3$): δ 7.52-7.45 (m, 2H), 7.07 (q, J=62.80 Hz, 1H), 3.45 (q, J=32.80 Hz, 1H), 3.01 (s, 1H), 2.60 (s, 2H), 2.58-1.87 (m, 4H), 1.60-1.40 (m, 2H), 1.30-1.22 (m, 2H), 1.20 (s, 6H), 0.95-0.90 (m, 2H). HRMS calculated for: $[C_{18}H_{24}F_4N_2O+H]$+361.1898; found: 361.1889 (deviation 2.4 ppm).

Example [15]—Methyl (2-amino-2-methylpropyl)(1-(3-(trifluoromethyl)phenyl)cyclopropyl)carbamate Step 1

The procedure used in Example [3], Step 1 was adapted such that 0.4 g of 1-(3-(trifluoromethyl)phenyl)cyclopropan-1-amine [10.1] and 0.52 g of tert-butyl (2-methyl-1-oxopropan-2-yl)carbamate were reacted to afford the product tert-butyl (2-methyl-1-((1-(3-(trifluoromethyl)phenyl)cyclopropyl)amino)propan-2-yl)carbamate [15.1](0.35 g, 69%, LCMS MH+=373.3).

Step 2

The procedure used in Example [1], Step 2 was adapted such that 0.3 g of tert-butyl (2-methyl-1-((1-(3-(trifluoromethyl)phenyl)cyclopropyl)amino)propan-2-yl)carbamate [15.1] was reacted to afford the product methyl (2-((tert-butoxycarbonyl)amino)-2-methylpropyl)(1-(3-(trifluoromethyl)phenyl)cyclopropyl)carbamate [15.2] as colourless liquid (0.2 g, 57%, LCMS MH+=431.4).

Step 3

The procedure used in Example [2], Step 4 was adapted such that 0.2 g of methyl (2-((tert-butoxycarbonyl)amino)-2-methylpropyl)(1-(3-(trifluoromethyl)phenyl)cyclopropyl) carbamate [15.2] was reacted to afford methyl (2-amino-2-methylpropyl)(1-(3-(trifluoromethyl)phenyl)cyclopropyl) carbamate [15] as an off-white solid (0.03 g, 20%). $^1$H-NMR (400 MHz, DMSO-d$_6$): δ 7.85 (bs, 2H), 7.57 (t, J=5.20 Hz, 2H), 7.40 (bs, 2H), 3.63 (s, 3H), 3.53 (s, 1H), 1.50 (bs, 2H), 1.37 (bs, 2H), 1.23 (bs, 1H), 1.18 (s, 6H). HRMS calculated for: [$C_{16}H_{21}F_3N_2O_2$+H]+331.1628; found: 331.1620 (deviation 2.5 ppm).

Example [16]—1-((1-(4-fluoro-3-(trifluoromethyl)phenyl)cyclopropyl)((1-methylazetidin-2-yl)methyl)amino)-2-methylpropan-2-ol The procedure used in Example [2], Step 2 was adapted such that 0.09 g of 1-((azetidin-2-ylmethyl)(1-(4-fluoro-3-(trifluoromethyl)phenyl)cyclopropyl) amino)-2-methylpropan-2-ol [14] was reacted to afford 1-((1-(4-fluoro-3-(trifluoromethyl)phenyl)cyclopropyl)((1-methylazetidin-2-yl)methyl)amino)-2-methylpropan-2-ol [16] as colourless gum (0.02 g, 21%, LCMS MH+=375.2). $^1$H-NMR (400 MHz, CDCl$_3$): δ 7.46-7.43 (m, 2H), 7.14 (t, J=9.20 Hz, 1H), 3.52-3.48 (m, 1H), 3.42-3.33 (m, 1H), 3.01-2.96 (m, 1H), 2.80-2.70 (m, 3H), 2.65 (d, J=13.20 Hz, 1H), 2.41 (s, 3H), 2.15-2.12 (m, 1H), 1.80-1.70 (m, 2H), 1.30-1.23 (m, 2H), 1.21-1.19 (m, 3H), 1.90-1.30 (m, 3H), 1.08-0.80 (m, 1H), 0.30-0.20 (m, 1H). HRMS calculated for: [$C_{19}H_{26}F_4N_2O$+H]+375.2054; found: 375.2044 (deviation 2.6 ppm).

Example [17]—Methyl (2-amino-2-methylpropyl)(1-(5-fluoro-4-(trifluoromethyl)pyridin-2-yl)cyclopropyl) carbamate Step 1

The procedure used in Example [3], Step 1 was adapted such that 0.054 g of 1-(5-fluoro-4-(trifluoromethyl)pyridin-2-yl)cyclopropan-1-amine [36.6] was reacted to afford tert-butyl (1-((1-(5-fluoro-4-(trifluoromethyl)pyridin-2-yl)cyclopropyl)amino)-2-methyl propan-2-yl)carbamate [17.1] as an off-white solid (0.052 g, 54%, LCMS MH+=392.2).

Step 2

The procedure used in Example [1], Step 2 was adapted such that 0.05 g of tert-butyl (1-((1-(5-fluoro-4-(trifluoromethyl)pyridin-2-yl)cyclopropyl)amino)-2-methylpropan-2-yl)carbamate [17.1] was reacted to afford methyl (2-((tert-butoxycarbonyl)amino)-2-methylpropyl)(1-(5-fluoro-4-(trifluoromethyl)pyridin-2-yl)cyclopropyl) carbamate [17.2] as an off-white solid (0.042 g, 73%, LCMS MH+=450.2).

Step 3

The procedure used in Example [2], Step 4 was adapted such that 0.04 g of methyl (2-((tert-butoxycarbonyl)amino)-2-methylpropyl)(1-(5-fluoro-4-(trifluoromethyl)pyridin-2-yl)cyclopropyl)carbamate was reacted to afford methyl (2-amino-2-methylpropyl)(1-(5-fluoro-4-(trifluoromethyl)pyridin-2-yl)cyclopropyl) carbamate [17] as an off-white solid (0.021 g, 61%, LCMS MH+=350.2). $^1$H-NMR (400 MHz, DMSO-d$_6$): δ 8.81 (s, 1H), 7.80 (s, 2H), 7.33 (s, 1H), 3.58 (s, 3H), 3.26-3.25 (m, 2H), 1.58-1.54 (m, 4H), 1.24-1.21 (m, 6H). HRMS calculated for: [$C_{15}H_{19}F_4N_3O_2$+H]+ 350.1486; found: 350.1483 (deviation 0.9 ppm).

Example [18]—N1-cyclobutyl-2-methyl-N1-(1-(3-(trifluoromethyl)phenyl)cyclopropyl)propane-1,2-diamine To a stirred solution of 2-(cyclobutyl(1-(3-(trifluoromethyl)phenyl)cyclopropyl)amino)acetonitrile [82] (0.25 g, 0.85 mmol) in toluene (3 mL) was added titanium(IV) isopropoxide (0.26 mL, 0.85 mmol) at −40° C. and the reaction stirred for 15 minutes. Methylmagnesium bromide solution (7.2 mmol) was added dropwise over a period of 10 minutes and the reaction subsequently stirred at room temperature for 18 h. The reaction was quenched with ammonium chloride solution and extracted with DCM (3×50 mL). The combined organics were concentrated in vacuo and purified by flash column chromatography using 15% EtOAc/pet ether as eluent to afford N1-cyclobutyl-2-methyl-N1-(1-(3-(trifluoromethyl)phenyl)cyclopropyl)propane-1,2-diamine [18] as a brownish gum (0.05 g, 18%, LCMS MH+=327.1) $^1$H-NMR (400 MHz, DMSO-d$_6$): δ 7.60-7.54 (m, 5H), 3.45-3.43 (m, 1H), 2.76 (s, 2H), 1.99-1.93 (m, 4H), 1.56-1.45 (m, 2H), 1.37-1.34 (m, 2H), 1.24-1.22 (m, 5H), 1.10-1.07 (m, 2H). HRMS calculated for: [$C_{18}H_{25}F_3N_2$+H]+327.2042; found: 327.2036 (deviation 2.2 ppm).

Example [19]—Ethyl (2-amino-2-methylpropyl)(1-(4-fluoro-3-(trifluoromethyl)phenyl)cyclopropyl) carbamate Step 1

The procedure used in Example [1], Step 2 was adapted such that 0.15 g of tert-butyl (1-((1-(4-fluoro-3-(trifluoromethyl)phenyl)cyclopropyl)amino)-2-methylpropan-2-yl)carbamate [2.2] was reacted with ethyl chloroformate to afford ethyl (2-((tert-butoxycarbonyl)amino)-2-methylpropyl) (1-(4-fluoro-3-(trifluoromethyl)phenyl)cyclopropyl)carbamate [19.1] as a colourless liquid (0.14 g, 79% LCMS MH+=463.2).

Step 2

The procedure used in Example [2], Step 4 was adapted such that 0.1 g of ethyl (2-((tert-butoxycarbonyl)amino)-2-methylpropyl)(1-(4-fluoro-3-(trifluoromethyl)phenyl)cyclopropyl)carbamate [19.1] was reacted to afford ethyl (2-amino-2-methylpropyl)(1-(4-fluoro-3-(trifluoromethyl)phenyl)cyclopropyl)carbamate [19] as an off-white solid (0.062 g, 72%, LCMS MH+=363.2). $^1$H-NMR (400 MHz, DMSO-d$_6$): δ 7.77 (bs, 3H), 7.63-7.58 (m, 1H), 7.54-7.45 (m, 2H), 4.13-4.08 (m, 2H), 3.55 (bs, 2H), 1.44 (s, 2H), 1.35 (bs, 2H), 2.00-1.50 (m, 6H), 1.50-1.10 (m, 3H). HRMS calculated for: [$C_{17}H_{22}F_4N_2O_2$+H]+ 363.1690; found: 363.1686 (deviation 1.1 ppm).

Example [20]—Methyl (2-amino-2-methylpropyl)(1-(4-fluoro-3-(trifluoromethoxy)phenyl)cyclopropyl)carbamate Step 1

The procedure used in Example [3], Step 1 was adapted such that 0.25 g of 1-(4-fluoro-3-(trifluoromethoxy)phenyl)cyclopropan-1-amine [9.1] and 0.19 g of tert-butyl (2-methyl-1-oxopropan-2-yl)carbamate [2.1] were reacted to afford the product tert-butyl (1-((1-(4-fluoro-3-(trifluoromethoxy)phenyl)cyclopropyl)amino)-2-methylpropan-2-yl)carbamate [20.1] as brown gum (0.26 g, 60%, LCMS MH+=407.2).

Step 2

The procedure used in Example [1], Step 2 was adapted such that 0.26 g of tert-butyl (1-((1-(4-fluoro-3-(trifluoromethoxy)phenyl)cyclopropyl)amino)-2-methylpropan-2-yl)carbamate [20.1] was reacted to afford the product methyl (2-((tert-butoxycarbonyl)amino)-2-methylpropyl)(1-(4-fluoro-3-(trifluoromethoxy)phenyl)cyclopropyl)carbamate [20.2] as colourless liquid (0.18 g, 60%, LCMS MH+=465.2).

Step 3

The procedure used in Example [2], Step 4 was adapted such that 0.18 g of methyl (2-((tert-butoxycarbonyl)amino)-2-methylpropyl)(1-(4-fluoro-3-(trifluoromethoxy)phenyl)cyclopropyl)carbamate [20.2] was reacted to afford methyl (2-amino-2-methylpropyl)(1-(4-fluoro-3-(trifluoromethoxy)

phenyl)cyclopropyl)carbamate [20] as an off-white solid (0.1 g, 71%). $^1$H-NMR (400 MHz, DMSO-d$_6$): δ 7.68 (bs, 2H), 7.46-7.42 (m, 1H), 7.28 (bs, 2H), 3.62 (s, 3H), 3.50 (bs, 2H), 1.41 (bs, 2H), 1.25 (bs, 2H), 1.12 (s, 6H). HRMS calculated for: [C$_{16}$H$_{20}$F$_4$N2O3+H]+365.1483; found: 365.1473 (deviation 2.6 ppm).

Example [21]—N-(2-amino-2-methylpropyl)-N-(1-(4-fluoro-3-(trifluoromethyl)phenyl)cyclopropyl)methanesulfonamide Step 1

The procedure used in Example [2], Step 4 was adapted such that 0.3 g of tert-butyl (1-((1-(4-fluoro-3-(trifluoromethyl)phenyl)cyclopropyl)amino)-2-methyl propan-2-yl)carbamate [2.2] was reacted with 0.26 g of sulfuryl dichloride to afford tert-butyl (1-(N-(1-(4-fluoro-3-(trifluoromethyl)phenyl)cyclopropyl)methylsulfonamido)-2-methylpropan-2-yl)carbamate [21.1] (0.12 g, 33%, LCMS MH$^+$=469.2).

Step 2

The procedure used in Example [2], Step 4 was adapted such that 0.12 g of tert-butyl (1-(N-(1-(4-fluoro-3-(trifluoromethyl)phenyl)cyclopropyl)methyl sulfonamido)-2-methylpropan-2-yl)carbamate [21.1] was reacted to afford N-(2-amino-2-methylpropyl)-N-(1-(4-fluoro-3-(trifluoromethyl)phenyl)cyclopropyl)methanesulfonamide [21] as an off-white solid (0.048 g, 50%). $^1$H-NMR (400 MHz, DMSO-d$_6$): δ 7.77 (dd, J=2.40, 6.40 Hz, 1H), 7.63-7.57 (m, 1H), 7.48-7.40 (m, 1H), 3.16 (s, 2H), 3.11 (s, 3H), 1.75-1.68 (m, 2H), 1.55 (s, 2H), 1.36 (d, J=1.20 Hz, 2H), 0.98 (s, 6H). HRMS calculated for: [C$_{15}$H$_{20}$F$_4$N$_2$O$_2$S+H]$^+$369.1254; found: 369.1242 (deviation 3.2 ppm).

Example [22]—Methyl (R)-(1-(4-fluoro-3-(trifluoromethyl)phenyl)cyclopropyl)(pyrrolidin-2-ylmethyl)carbamate Step 1

The procedure used in Example [2], Step 1 was adapted such that 2 g of tert-butyl (2R)-2-(hydroxymethyl)pyrrolidine-1-carboxylate was reacted to afford tert-butyl (2R)-2-formylpyrrolidine-1-carboxylate [22.1] as a pale yellow liquid (1.5 g (crude), 79%).

Step 2

The procedure used in Example [2], Step 2 was adapted such that 1.5 g of 1-(4-fluoro-3-(trifluoromethyl)phenyl)cyclopropan-1-amine [1.1] was reacted with tert-butyl (2R)-2-formylpyrrolidine-1-carboxylate [22.1] to afford tert-butyl (R)-2-(((1-(4-fluoro-3-(trifluoromethyl)phenyl)cyclopropyl)amino)methyl)pyrrolidine-1-carboxylate as colourless liquid (1.3 g, 48%, LCMS MH$^+$=403.2).

Step 3

The procedure used in Example [1], Step 2 was adapted such that 0.25 g of tert-butyl (R)-2-(((1-(4-fluoro-3-(trifluoromethyl)phenyl)cyclopropyl)amino)methyl)pyrrolidine-1-carboxylate [22.2] and 0.09 g of methyl chloroformate were reacted to afford tert-butyl (R)-2-(((1-(4-fluoro-3-(trifluoromethyl)phenyl)cyclopropyl)(methoxycarbonyl) amino)methyl)pyrrolidine-1-carboxylate [22.3] as a colourless gum (0.13 g, 52%, LCMS MH$^+$=361.4 (Boc-cleaved mass)).

Step 4

To a stirred solution of tert-butyl (R)-2-(((1-(4-fluoro-3-(trifluoromethyl)phenyl)cyclopropyl)(methoxycarbonyl)amino)methyl)pyrrolidine-1-carboxylate [22.3] (0.12 g, 0.26 mmol) in DCM was added HCl gas in diethyl ether at 0° C. and the reaction stirred at room temperature for 16 h. The reaction mixture was concentrated under reduced pressure to afford crude product which was purified by trituration in diethyl ether to afford methyl (R)-(1-(4-fluoro-3-(trifluoromethyl)phenyl)cyclopropyl)(pyrrolidin-2-ylmethyl)carbamate [22] (HCl salt) as a white solid (0.1 g, 97%, LCMS MH$^+$=361.2). $^1$H-NMR (400 MHz, DMSO-d$_6$): δ 9.30-9.00 (bs, 1H), 8.60-8.20 (bs, 1H), 7.54-7.38 (m, 3H), 3.76-0.75 (m, 1H), 3.62-3.50 (m, 4H), 3.30-3.18 (m, 1H), 3.12-3.00 (m, 1H), 2.04-1.94 (m, 1H), 1.90-1.82 (m, 2H), 1.57-1.50 (m, 2H), 1.40-1.30 (m, 2H). HRMS calculated for: [C$_{17}$H$_{20}$F$_4$N2O2+H]+361.1534; found: 361.1521 (deviation 3.6 ppm).

Example [23]—Methyl (S)-(1-(4-fluoro-3-(trifluoromethyl)phenyl)cyclopropyl)(pyrrolidin-2-ylmethyl)carbamate Step 1

The procedure used in Example [2], Step 1 was adapted such that 3 g of tert-butyl (2S)-2-(hydroxymethyl)pyrrolidine-1-carboxylate was reacted to afford tert-butyl (2S)-2-formylpyrrolidine-1-carboxylate [23.1] as a pale yellow liquid (2 g (crude), 62%).

Step 2

The procedure used in Example [2], Step 2 was adapted such that 1 g of 1-[4-fluoro-3-(trifluoromethyl)phenyl]cyclopropan-1-amine [1.1] was reacted with tert-butyl (2S)-2-formylpyrrolidine-1-carboxylate [23.1] to afford tert-butyl (S)-2-(((1-(4-fluoro-3-(trifluoromethyl)phenyl)cyclopropyl)amino)methyl)pyrrolidine-1-carboxylate [23.2] (1.2 g, 66%, LCMS MH$^+$=403.2).

Step 3

The procedure used in Example [1], Step 2 was adapted such that 1 g of tert-butyl (S)-2-(((1-(4-fluoro-3-(trifluoromethyl)phenyl)cyclopropyl)amino)methyl)pyrrolidine-1-carboxylate [23.2] and 0.21 g of methyl chloroformate were reacted to afford tert-butyl (S)-2-(((1-(4-fluoro-3-(trifluoromethyl)phenyl)cyclopropyl)(methoxycarbonyl) amino)methyl)pyrrolidine-1-carboxylate (0.25 g, 73%, LCMS MH$^+$=461.2).

Step 4

The procedure used in Example [22], Step 4 was adapted such that 0.12 g of tert-butyl (S)-2-(((1-(4-fluoro-3-(trifluoromethyl)phenyl)cyclopropyl)(methoxycarbonyl)amino)methyl)pyrrolidine-1-carboxylate [23.3] was reacted to afford methyl (S)-(1-(4-fluoro-3-(trifluoromethyl)phenyl)cyclopropyl)(pyrrolidin-2-ylmethyl)carbamate [23] (HCl salt) as an off-white solid (0.09 g, 90%, LCMS MH$^+$=361.2). $^1$H-NMR (400 MHz, DMSO-d$_6$): δ 9.60-9.40 (bs, 1H), 9.00-8.20 (bs, 1H), 7.49-7.38 (m, 3H), 3.73-3.60 (m, 6H), 3.23-3.07 (m, 2H), 1.98-1.85 (m, 3H), 1.70-1.40 (m, 3H), 1.36-1.29 (m, 2H). HRMS calculated for: [C$_{17}$H$_{20}$F$_4$N2O2+H]+361.1534; found: 361.1524 (deviation 2.6 ppm).

Example [24]—Methyl (2-acetamido-2-methylpropyl)(1-(4-fluoro-3-(trifluoromethyl)phenyl)cyclopropyl)carbamate The procedure used in Example [1], Step 2 was adapted such that 0.1 g of methyl (2-amino-2-methylpropyl)(1-(4-fluoro-3-(trifluoromethyl)phenyl)cyclopropyl)carbamate [2] and 0.022 g of acetyl chloride were reacted to afford methyl (2-acetamido-2-methylpropyl)(1-(4-fluoro-3-(trifluoromethyl)phenyl)cyclopropyl)carbamate [24] as a colourless gum (0.034 g, 30%). $^1$H-NMR (400 MHz, DMSO-d$_6$): δ 7.53-7.38 (m, 2H), 7.30 (bs, 3H), 3.73 (s, 2H), 3.61 (s, 3H), 1.52 (s, 3H), 1.43 (bs, 2H), 1.30 (bs, 2H), 1.14 (s, 6H).

HRMS calculated for: [C$_{18}$H$_{22}$F$_4$N2O3+H]+391.1639; found: 391.1637 (deviation 0.7 ppm).

Example [25]—N1-(1-(4-fluoro-3-(trifluoromethyl)phenyl)cyclopropyl)-2-methylpropane-1,2-diamine The procedure used in Example [2], Step 4 was adapted such that 0.1 g of tert-butyl (1-(((1-(4-fluoro-3-(trifluoromethyl)phenyl)cyclopropyl)amino)-2-methylpropan-2-yl)carbamate [2.2] was reacted to afford N1-(1-(4-fluoro-3-(trifluoromethyl)phenyl)cyclopropyl)-2-methylpropane-1,2-diamine [25] as a colourless gum (0.05 g, 67%). $^1$H-NMR (400 MHz, DMSO-d$_6$): δ 7.74 (dd, J=2.00, 7.00 Hz, 1H), 7.62-7.56 (m, 1H), 7.43-7.36 (m, 1H), 2.59 (bs, 1H), 2.20 (s, 2H), 1.40 (bs, 2H), 1.00-0.98 (m, 2H), 0.93 (s, 6H). HRMS calculated for: [C$_{14}$H$_{18}$F$_4$N2+H]+290.1479; found: 291.1467 (deviation 4.1 ppm).

Example [26]—Methyl (azetidin-2-ylmethyl)(1-(4-fluoro-3-(trifluoromethyl)phenyl)cyclopropyl)carbamate Step 1

The procedure used in Example [1], Step 2 was adapted such that 0.45 g of tert-butyl 2-(((1-(4-fluoro-3-(trifluoromethyl)phenyl)cyclopropyl)amino)methyl)azetidine-1-carboxylate [14.2] was reacted to afford tert-butyl 2-(((1-(4-fluoro-3-(trifluoromethyl)phenyl)cyclopropyl)(methoxycarbonyl)amino)methyl)azetidine-1-carboxylate [26.1] as a colourless gum (0.125 g, 25%, LCMS MH$^+$=447.1).

Step 2

To a stirred solution of tert-butyl 2-(((1-(4-fluoro-3-(trifluoromethyl)phenyl)cyclopropyl)(methoxycarbonyl)amino)methyl)azetidine-1-carboxylate [26.1] (0.25 g, 0.56 mmol) in dichloromethane (6 mL) at 0° C. was added trifluoroacetic acid (4 mL, 52 mmol) and the reaction stirred at rt for 12 h. The reaction was diluted with sat. aq. sodium bicarbonate solution and extracted with ethyl acetate. The combined organic layers were washed with brine solution and concentrated under reduced pressure to afford the crude product which was purified by Prep HPLC to afford methyl (azetidin-2-ylmethyl)(1-(4-fluoro-3-(trifluoromethyl)phenyl)cyclopropyl)carbamate [26]trifluoroacetate salt as a white solid, (0.035 g, 19%, LCMS MH$^+$=347.1). $^1$H-NMR (400 MHz, DMSO-d$_6$): δ 8.58 (bs, 1H), 7.60-7.45 (m, 2H), 7.38 (s, 1H), 4.43 (bs, 1H), 3.90 (bs, 1H), 3.85-3.75 (m, 2H), 3.66-3.63 (m, 3H), 3.63-3.60 (m, 1H), 2.35-2.10 (m, 2H), 1.50-1.25 (m, 4H). HRMS calculated for: [C$_{16}$H$_{18}$F$_4$N2O2+H]+347.1377; found: 347.1374 (deviation 0.9 ppm).

Example [27]—Methyl (S)-(1-(4-fluoro-3-(trifluoro methyl) phenyl)cyclopropyl) ((1-methylpyrrolidin-2-yl)methyl) carbamate The procedure used in Example [2], Step 2 was adapted such that 0.08 g of methyl (S)-(1-(4-fluoro-3-(trifluoromethyl)phenyl)cyclopropyl)(pyrrolidin-2-ylmethyl)carbamate [23] was reacted to afford methyl (S)-(1-(4-fluoro-3-(trifluoro methyl) phenyl)cyclopropyl) ((1-methylpyrrolidin-2-yl)methyl) carbamate [27] as a colourless gum (0.055 g, 73%). $^1$H-NMR (400 MHz, DMSO-d$_6$): δ 7.49-7.42 (m, 3H), 3.65-3.60 (m, 3H), 3.33-3.26 (m, 2H), 2.89-2.86 (m, 1H), 2.50-2.30 (m, 1H), 2.20 (s, 3H), 2.08-2.06 (m, 1H), 1.23-1.61 (m, 8H). HRMS calculated for: [C$_{18}$H$_{22}$F$_4$N2O2+H]+375.1690; found: 375.1683 (deviation 1.8 ppm).

Example [28]—Methyl (S)-(1-(4-fluoro-3-(trifluoromethoxy)phenyl)cyclopropyl)(pyrrolidin-2-ylmethyl)carbamate Step 1

The procedure used in Example [3], Step 1 was adapted such that 0.3 g of 1-(4-fluoro-3-(trifluoromethoxy)phenyl)cyclopropan-1-amine [9.1] was reacted to afford tert-butyl (S)-2-(((1-(4-fluoro-3-(trifluoromethoxy)phenyl)cyclopropyl)amino)methyl)pyrrolidine-1-carboxylate [28.1] as a pale brown gum (0.3 g, 54%, LCMS MH$^+$=419.2).

Step 2

The procedure used in Example [1], Step 2 was adapted such that 0.3 g of tert-butyl (S)-2-(((1-(4-fluoro-3-(trifluoromethoxy)phenyl)cyclopropyl)amino)methyl)pyrrolidine-1-carboxylate [28.1] was reacted to afford tert-butyl (S)-2-(((1-(4-fluoro-3-(trifluoromethoxy)phenyl)cyclopropyl)(methoxycarbonyl)amino)methyl)pyrrolidine-1-carboxylate [28.2] as colourless gum (0.3 g, 85%, LCMS MH=477.1).

Step 3

The procedure used in Example [2], Step 4 was adapted such that 0.15 g of tert-butyl (S)-2-(((1-(4-fluoro-3-(trifluoromethoxy)phenyl)cyclopropyl)(methoxycarbonyl)amino)methyl)pyrrolidine-1-carboxylate [28.2] was reacted to afford methyl (S)-(1-(4-fluoro-3-(trifluoromethoxy)phenyl)cyclopropyl)(pyrrolidin-2-ylmethyl)carbamate [28] as a white solid (0.65 g, 60%, LCMS MH$^+$=377.1). $^1$H-NMR (400 MHz, DMSO-d$_6$): δ 9.20 (bs, 1H), 8.45 (bs, 1H), 7.50-7.42 (m, 1H), 7.25 (bs, 2H), 3.69 (bs, 1H), 3.64 (s, 3H), 3.56 (s, 2H), 3.30-3.20 (m, 1H), 3.12-3.02 (m, 1H), 2.05-1.45 (m, 1H), 1.95-1.28 (m, 2H), 1.60-1.40 (m, 3H), 1.35 (bs, 1H), 1.25 (bs, 1H). HRMS calculated for: [C$_{17}$H$_{20}$F$_4$N2O3+H]$^+$377.1483; found: 377.1476 (deviation 1.8 ppm).

Example [29]—Methyl (R)-(1-(4-fluoro-3-(trifluoromethoxy)phenyl)cyclopropyl)(pyrrolidin-2-ylmethyl)carbamate Step 1

The procedure used in Example [3], Step 1 was adapted such that 0.4 g of 1-(4-fluoro-3-(trifluoromethoxy)phenyl)cyclopropan-1-amine [9.1] was reacted to afford tert-butyl (R)-2-(((1-(4-fluoro-3-(trifluoromethoxy)phenyl)cyclopropyl)amino)methyl)pyrrolidine-1-carboxylate [29.1] as a colourless liquid (0.35 g, 49%, LCMS MH$^+$=419.1).

Step 2

The procedure used in Example [1], Step 2 was adapted such that 0.35 g of tert-butyl (R)-2-(((1-(4-fluoro-3-(trifluoromethoxy)phenyl)cyclopropyl)amino)methyl)pyrrolidine-1-carboxylate [29.1] was reacted to afford tert-butyl (R)-2-(((1-(4-fluoro-3-(trifluoromethoxy)phenyl)cyclopropyl)(methoxycarbonyl)amino)methyl)pyrrolidine-1-carboxylate [29.2] as a pale brown gum (0.2 g, 50%, LCMS MH$^+$=477.2).

Step 3

The procedure used in Example [2], Step 4 was adapted such that 0.1 g of tert-butyl (R)-2-(((1-(4-fluoro-3-(trifluoromethoxy)phenyl)cyclopropyl)(methoxycarbonyl)amino)methyl)pyrrolidine-1-carboxylate [29.2] was reacted to afford methyl (R)-(1-(4-fluoro-3-(trifluoromethoxy)phenyl)cyclopropyl)(pyrrolidin-2-ylmethyl)carbamate [29] (HCl salt) as a white solid (0.05 g, 58%, LCMS MH$^+$=377.2). $^1$H-NMR (400 MHz, DMSO-d$_6$): δ 9.15 (bs, 1H), 8.25 (bs, 1H), 7.27-7.22 (m, 1H), 7.13 (bs, 2H), 3.80-3.68 (m, 1H), 3.64 (s, 3H), 3.62-3.50 (m, 2H), 3.30-3.20 (m, 1H), 3.12-3.02 (m, 1H), 2.05-1.78 (m, 3H), 1.60-1.40 (m, 2H), 1.40-

Example [30]—Methyl (1-(4-fluoro-3-(trifluoromethyl)phenyl)cyclopropyl)((1-methylazetidin-2-yl)methyl)carbamate The procedure used in Example [2], Step 2 was adapted such that 0.19 g of methyl (azetidin-2-ylmethyl)(1-(4-fluoro-3-(trifluoromethyl)phenyl)cyclopropyl)carbamate [26] was reacted to afford methyl (1-(4-fluoro-3-(trifluoromethyl)phenyl)cyclopropyl)((1-methylazetidin-2-yl)methyl)carbamate [30] as a colourless gum (0.02 g, 10%, LCMS MH$^+$=361.1). $^1$H-NMR (400 MHz, CDCl$_3$): δ 7.28-7.20 (m, 1H), 7.15-7.10 (m, 1H), 7.06-7.03 (m, 1H), 3.69 (s, 3H), 3.45-3.25 (m, 3H), 2.64 (bs, 1H), 2.20 (bs, 3H), 1.95-1.73 (m, 2H), 1.63 (bs, 2H), 1.44 (bs, 1H), 1.30-1.18 (m, 2H). HRMS calculated for: [C$_{17}$H$_{20}$F$_4$N2O2+H]+361.1534; found: 361.1528 (deviation 1.7 ppm).

Example [31]—Methyl (R)-(1-(4-fluoro-3-(trifluoromethyl)phenyl)cyclopropyl)((1-methylpyrrolidin-2-yl)methyl)carbamate The procedure used in Example [2], Step 2 was adapted such that 0.02 g of methyl (R)-(1-(4-fluoro-3-(trifluoromethyl)phenyl)cyclopropyl)(pyrrolidin-2-ylmethyl)carbamate [22] was reacted to afford methyl (R)-(1-(4-fluoro-3-(trifluoromethyl)phenyl)cyclopropyl)((1-methylpyrrolidin-2-yl)methyl)carbamate [31] as colourless gum (0.013 g, 62%). $^1$H-NMR (400 MHz, DMSO-d$_6$): δ 7.60-7.30 (m, 3H), 3.59 (s, 3H), 3.35-3.25 (m, 2H), 2.91-2.80 (m, 1H), 2.38 (s, 1H), 2.19 (s, 3H), 2.11-2.00 (m, 1H), 1.70-1.50 (m, 4H), 1.50-1.20 (m, 4H). HRMS calculated for: [C$_{18}$H$_{22}$F$_4$N2O3+H]+ 375.1690; found: 375.1679 (deviation 3.1 ppm).

Example [32]—Methyl (azetidin-2-ylmethyl)(1-(4-fluoro-3-(trifluoromethoxy)phenyl)cyclopropyl)carbamate Step 1
The procedure used in Example [14], Step 1 was adapted such that 0.6 g of 1-(4-fluoro-3-(trifluoromethoxy)phenyl)cyclopropan-1-amine [9.1] was reacted to afford tert-butyl 2-((1-(4-fluoro-3-(trifluoromethoxy)phenyl)cyclopropyl)carbamoyl)azetidine-1-carboxylate [32.1] as a colourless gum (0.6 g, 56%, LCMS MH$^+$=419.2).
Step 2
To a stirred solution of tert-butyl 2-((1-(4-fluoro-3-(trifluoromethoxy)phenyl)cyclopropyl)carbamoyl)azetidine-1-carboxylate [32.1] (0.6 g, 1.43 mmol) in dry THF (3 mL) was added borane dimethyl sulphide complex (0.46 g, 5.74 mmol) dropwise under N2 atm. The resultant reaction mixture was slowly warmed to rt, then heated to 60° C. for 2 h. The reaction mixture was quenched sat. aq. ammonium chloride solution and extracted with ethyl acetate (2×30 mL). The combined organic layer was washed with brine, dried over sodium sulphate, filtered and concentrated under reduced pressure to afford the crude product which was purified by flash column chromatography using ethyl acetate/hexane as eluent to afford tert-butyl 2-(((1-(4-fluoro-3-(trifluoromethoxy)phenyl)cyclopropyl)amino)methyl)azetidine-1-carboxylate [32.2] as a colourless gum (0.2 g, 34%, LCMS MH$^+$=405.1).
Step 3
The procedure used in Example [1], Step 2 was adapted such that 0.2 g of tert-butyl 2-(((1-(4-fluoro-3-(trifluoromethoxy)phenyl)cyclopropyl)amino)methyl)azetidine-1-carboxylate [32.2] was reacted to afford tert-butyl 2-(((1-(4-fluoro-3-(trifluoromethoxy)phenyl)cyclopropyl)(methoxycarbonyl)amino)methyl)azetidine-1-carboxylate [32.3] as a colourless gum (0.2 g, 87%, LCMS MH$^+$=463.2).
Step 4
The procedure used in Example [26], Step 2 was adapted such that 0.2 g of tert-butyl 2-(((1-(4-fluoro-3-(trifluoromethoxy)phenyl)cyclopropyl)(methoxycarbonyl)amino)methyl)azetidine-1-carboxylate [32.3] was reacted to afford methyl (azetidin-2-ylmethyl)(1-(4-fluoro-3-(trifluoromethoxy)phenyl)cyclopropyl)carbamate [32] as a colourless gum (0.055 g, 35%, LCMS MH$^+$=463.2). $^1$H-NMR (400 MHz, DMSO-d$_6$): δ 7.42 (t, J=10.40 Hz, 1H), 7.30-7.05 (m, 2H), 3.91 (s, 1H), 3.57 (s, 3H), 3.50-3.40 (m, 2H), 3.05 (s, 1H), 2.08-1.80 (m, 3H), 1.50-1.28 (m, 2H), 1.23 (s, 2H). HRMS calculated for: [C$_{16}$H$_{18}$F$_4$N2O3+H]+363.1326; found: 363.1321 (deviation 1.4 ppm).

Example [33]—Methyl (1-(4-fluoro-3-(trifluoromethyl)phenyl)cyclopropyl)(2-(hydroxyamino)-2-methylpropyl)carbamate Step 1
To a stirred solution of methyl (2-amino-2-methylpropyl)(1-(4-fluoro-3-(trifluoromethyl)phenyl)cyclopropyl)carbamate [2] (0.25 g, 0.717 mmol) in DMF (5 mL) was added benzoyl peroxide (0.26 g, 1.076 mmol) and potassium phosphate (0.146 g, 1.076 mmol) at 0° C. The resultant reaction mixture was slowly warmed to rt and stirred at rt for 12 h. The reaction mixture was quenched with water and extracted with ethyl acetate (2*25 mL), the combined organic layer was dried over sodium sulphate and concentrated to afford crude product which was purified by column chromatography using 15% ethyl acetate in hexane as eluent to afford methyl (2-((benzoyloxy)amino)-2-methylpropyl)(1-(4-fluoro-3-(trifluoromethyl)phenyl)cyclopropyl)carbamate [33.1] as an off white solid (0.18 g, 54%).
Step 2
To a stirred solution of methyl (2-((benzoyloxy)amino)-2-methylpropyl)(1-(4-fluoro-3-(trifluoromethyl)phenyl)cyclopropyl)carbamate [33.1] (0.16 g, 0.341 mmol) in methanol (5 mL) was added hydrazine monohydrate (3 mL g, 61.72 mmol) at 0° C. The resultant reaction mixture was slowly warmed to rt and stir at rt for 12 h. The reaction mixture was quenched with water and extracted with ethyl acetate (2*25 mL), the combined organic layer was dried over sodium sulphate and concentrated to afford crude product which was purified by Prep HPLC to afford methyl (1-(4-fluoro-3-(trifluoromethyl)phenyl)cyclopropyl)(2-(hydroxyamino)-2-methylpropyl)carbamate [33] as an off white solid (15.7 mg, 13%). $^1$H-NMR (400 MHz, DMSO-d$_6$): δ 7.50 (bs, 1H), 7.42 (t, J=8.80 Hz, 2H), 6.87 (s, 1H), 5.05 (bs, 1H), 3.56 (s, 3H), 3.40-3.35 (m, 2H), 1.28-1.26 (m, 2H), 1.22-1.24 (m, 2H), 0.85 (d, J=10.40 Hz, 6H). HRMS calculated for: [C$_{16}$H$_{20}$F$_4$N2O3+H]+365.1483; found: 365.1478 (deviation 1.3 ppm).

Example [34]—Ethyl (S)-(1-(4-fluoro-3-(trifluoromethyl)phenyl)cyclopropyl)(pyrrolidin-2-ylmethyl)carbamate Step 1
The procedure used in Example [1], Step 2 was adapted such that 0.25 g of tert-butyl (S)-2-(((1-(4-fluoro-3-(trifluoromethyl)phenyl)cyclopropyl)amino)methyl)pyrrolidine-1-carboxylate [23.2] was reacted to afford tert-butyl (S)-2-

(((ethoxycarbonyl)(1-(4-fluoro-3-(trifluoromethyl)phenyl)cyclopropyl)amino)methyl)pyrrolidine-1-carboxylate [34.1] as colourless gum (0.16 g, 55%, LCMS MH$^+$=375.2 (boc-cleaved mass)).

Step 2

The procedure used in Example [2], Step 4 was adapted such that 0.14 g of tert-butyl (S)-2-(((ethoxycarbonyl)(1-(4-fluoro-3-(trifluoromethyl)phenyl)cyclopropyl)amino)methyl)pyrrolidine-1-carboxylate was reacted to afford ethyl (S)-(1-(4-fluoro-3-(trifluoromethyl)phenyl)cyclopropyl)(pyrrolidin-2-ylmethyl)carbamate [34] as white solid (0.1 g, 83%). MS (M+1)+=375.2. $^1$H-NMR (400 MHz, DMSO-d$_6$): δ 9.40-9.05 (bs, 1H), 8.60-8.20 (bs, 1H), 7.65-7.52 (m, 1H), 7.49 (t, J=9.20 Hz, 2H), 4.11 (q, J=7.20 Hz, 2H), 3.70-3.65 (m, 1H), 3.65-3.52 (m, 2H), 3.30-3.18 (m, 1H), 3.15-3.00 (m, 1H), 2.05-1.60 (m, 3H), 1.65-1.40 (m, 3H), 1.40-1.10 (m, 5H). HRMS calculated for: [C$_{18}$H$_{22}$F$_4$N2O2+H]+ 375.1690; found: 375.1686 (deviation 1.2 ppm).

Example [35]—Ethyl (S)-(1-(4-fluoro-3-(trifluoromethyl)phenyl)cyclopropyl)((1-methylpyrrolidin-2-yl)methyl) carbamate The procedure used in Example [2], Step 2 was adapted such that 0.1 g of ethyl (S)-(1-(4-fluoro-3-(trifluoromethyl)phenyl)cyclopropyl)(pyrrolidin-2-ylmethyl)carbamate [34] was reacted to afford ethyl (S)-(1-(4-fluoro-3-(trifluoromethyl)phenyl)cyclopropyl)((1-methylpyrrolidin-2-yl)methyl) carbamate [35] as colourless gum (0.075 g, 80%, LCMS MH$^+$=389.1). $^1$H-NMR (400 MHz, DMSO-d$_6$): δ 7.52 (d, J=5.20 Hz, 2H), 7.38 (t, J=8.80 Hz, 1H), 4.08 (q, J=7.20 Hz, 2H), 3.30 (d, J=6.00 Hz, 2H), 2.90 (q, J=4.80 Hz, 1H), 2.22 (s, 3H), 2.12 (q, J=8.40 Hz, 2H), 1.70-1.50 (m, 4H), 1.50-1.20 (m, 4H), 1.16 (t, J=6.80 Hz, 3H). HRMS calculated for: [C$_{19}$H$_{24}$F$_4$N2O2+H]+389.1847; found: 389.1843 (deviation 1.0 ppm).

Example [36]—(S)—N-(1-(4-fluoro-3-(trifluoromethyl)phenyl)cyclopropyl)-N-(pyrrolidin-2-ylmethyl)methanesulfonamide Step 1

The procedure used in Example [1], Step 2 was adapted such that 0.8 g of tert-butyl (S)-2-(((1-(4-fluoro-3-(trifluoromethyl)phenyl)cyclopropyl)amino)methyl)pyrrolidine-1-carboxylate [23.2] and 0.69 g of methanesulphonyl chloride were reacted to afford the product tert-butyl (S)-2-((N-(1-(4-fluoro-3-(trifluoromethyl)phenyl)cyclopropyl)methylsulfonamido)methyl)pyrrolidine-1-carboxylate [36.1] as a colourless gum (0.4 g, 42%).

Step 2

The procedure used in Example [22], Step 4 was adapted such that 0.4 g of tert-butyl (S)-2-((N-(1-(4-fluoro-3-(trifluoromethyl)phenyl)cyclopropyl)methylsulfonamido)methyl)pyrrolidine-1-carboxylate [36.1] was reacted to afford (S)—N-(1-(4-fluoro-3-(trifluoromethyl)phenyl)cyclopropyl)-N-(pyrrolidin-2-ylmethyl) methanesulfonamide [36] as an off-white solid (0.28 g, 80%). 1H-NMR (400 MHz, DMSO-d$_6$): δ 9.50-9.25 (s, 1H), 8.95-8.65 (s, 1H), 7.84-7.78 (m, 2H), 7.46 (t, J=8.80 Hz, 1H), 3.80-3.55 (m, 3H), 3.35-3.00 (m, 2H), 2.92 (s, 3H), 2.10-1.65 (m, 3H), 1.65-1.50 (m, 3H), 1.35-1.26 (m, 2H). HRMS calculated for: [C$_{16}$H$_{20}$F$_4$N2O2+H]+381.1254; found: 381.1250 (deviation 1.3 ppm).

Example [37]—(S)—N-(1-(4-fluoro-3-(trifluoromethyl)phenyl)cyclopropyl)-N-((1-methylpyrrolidin-2-yl)methyl)methanesulfonamide The procedure used in Example [2], Step 2 was adapted such that 0.12 g of (S)—N-(1-(4-fluoro-3-(trifluoromethyl)phenyl)cyclopropyl)-N-(pyrrolidin-2-ylmethyl)methanesulfonamide [36] was reacted to afford (S)—N-(1-(4-fluoro-3-(trifluoromethyl)phenyl)cyclopropyl)-N-((1-methylpyrrolidin-2-yl)methyl)methanesulfonamide [37] as a colourless gum (0.08 g, 67%). $^1$H-NMR (400 MHz, DMSO-d$_6$): δ 7.69 (dd, J=2.12, 6.68 Hz, 1H), 7.61-7.60 (m, 1H), 7.47 (t, J=9.04 Hz, 1H), 3.25 (dd, J=40.00 Hz, 1H), 3.13-3.04 (m, 1H), 2.95-2.90 (m, 3H), 2.90-2.85 (m, 1H), 2.40-2.32 (m, 1H), 2.30-2.20 (m, 3H), 2.15-2.00 (m, 1H), 1.70-1.50 (m, 6H), 1.45-1.20 (m, 2H). HRMS calculated for: [C$_{17}$H$_{22}$F$_4$N2O2+H]+395.1411; found: 395.1406 (deviation 1.3 ppm).

Example [38]—Ethyl (R)-(1-(4-fluoro-3-(trifluoromethyl)phenyl)cyclopropyl)(pyrrolidin-2-ylmethyl)carbamate Step 1

The procedure used in Example [1], Step 2 was adapted such that 0.25 g of tert-butyl (R)-2-(((1-(4-fluoro-3-(trifluoromethyl)phenyl)cyclopropyl)amino)methyl) pyrrolidine-1-carboxylate [22.2] and 0.07 g of ethylchloroformate were reacted to afford tert-butyl (R)-2-(((ethoxycarbonyl)(1-(4-fluoro-3-(trifluoromethyl)phenyl)cyclopropyl)amino)methyl)pyrrolidine-1-carboxylate [38.1] as a colourless gum (0.14 g, 48%, LCMS MH$^+$=375.1 (Boc-cleaved mass)).

Step 2

The procedure used in Example [22], Step 4 was adapted such that 0.13 g of tert-butyl (R)-2-(((ethoxycarbonyl)(1-(4-fluoro-3-(trifluoromethyl)phenyl)cyclopropyl)amino)methyl)pyrrolidine-1-carboxylate was reacted to afford ethyl (R)-(1-(4-fluoro-3-(trifluoromethyl)phenyl)cyclopropyl)(pyrrolidin-2-ylmethyl)carbamate [38](HCl salt) as a white solid (0.115 g, 99%, LCMS MH$^+$=375.1). $^1$H-NMR (400 MHz, DMSO-d$_6$): δ 9.30-9.10 (bs, 1H), 8.60-8.20 (bs, 1H), 7.58-7.46 (m, 3H), 4.13-4.08 (m, 2H), 3.80-3.50 (m, 3H), 3.30-3.18 (m, 1H), 3.15-3.00 (m, 1H), 2.10-1.70 (m, 3H), 1.59-1.49 (m, 3H), 1.35-1.07 (m, 5H). HRMS calculated for: [C$_{18}$H$_{22}$F$_4$N2O2+H]+375.1690; found: 375.1688 (deviation 0.5 ppm).

Example [39]—Methyl (R)-(1-(4-fluoro-3-(trifluoromethyl)phenyl)cyclopropyl)(morpholin-3-ylmethyl) carbamate Step 1

To an ice cooled solution of (S)-4-(tert-butoxy carbonyl)-morpholine-3-carboxylic acid (0.37 g, 1.642 mmol) in dichloromethane (10 mL) was added triethylamine (0.76 mL, 5.474 mmol) and followed by propylphosphonic anhydride (2.61 g, 4.106 mmol) solution under N2 atm. The resultant reaction mixture was stirred at 0° C. for 20 min, then 1-(4-fluoro-3-(trifluoromethyl)phenyl)cyclopropan-1-amine [1.1] (0.3 g, 1.368 mmol) was added and the reaction stirred at rt for 5 h. The reaction mixture was quenched with water and extracted with ethyl acetate (2*80 mL). The combined organic layer was washed with 10% sodium bicarbonate solution, brine, dried over sodium sulphate, filtered and concentrated under reduced pressure to afford tert-butyl (S)-3-((1-(4-fluoro-3-(trifluoromethyl)phenyl)cyclopropyl)carbamoyl)morpholine-4-carboxylate [39.1] as a yellow liquid (0.55 g, 93%, LCMS MH=433.1).

Step 2

To a cooled solution of tert-butyl (S)-3-((1-(4-fluoro-3-(trifluoromethyl)phenyl)cyclopropyl)carbamoyl)morpholine-4-carboxylate [39.1] (0.55 g, 1.271 mmol) in dry THF (5 mL) was added borane dimethyl sulphide complex (9.6 mL, 2.543 mmol) dropwise under N2 atm. The resultant reaction mixture was slowly warmed to rt and stirred at rt for 16 h. The reaction mixture was quenched with methanol and the refluxed for 1 h and then concentrated under reduced pressure. The obtained residue was diluted with water and extracted with dichloromethane (2*100 mL), the combined organic layer was washed with brine, dried over sodium sulphate, filtered and concentrated under reduced pressure to afford tert-butyl (3R)-3-(((1-(4-fluoro-3-(trifluoromethyl)phenyl)cyclopropyl)amino)methyl)morpholine-4-carboxylate [39.2] as a colourless gum (0.28 g, 52%, LCMS MH$^+$=419.2).

Step 3

The procedure used in Example [1], Step 2 was adapted such that 0.25 g of tert-butyl (3R)-3-(((1-(4-fluoro-3-(trifluoromethyl)phenyl)cyclopropyl)amino)methyl)morpholine-4-carboxylate [39.2] was reacted to afford the product tert-butyl (R)-3-(((1-(4-fluoro-3-(trifluoro methyl)phenyl) cyclopropyl)(methoxycarbonyl)amino)methyl)morpholine-4-carboxylate as a Colourless gum (0.2 g, 71%, LCMS MH$^+$=477.2).

Step 4

The procedure used in Example [1], Step 2 was adapted such that 0.2 g of tert-butyl (R)-3-(((1-(4-fluoro-3-(trifluoromethyl)phenyl)cyclopropyl)(methoxycarbonyl)amino) methyl)morpholine-4-carboxylate [39.3] was reacted to afford methyl (R)-(1-(4-fluoro-3-(trifluoromethyl)phenyl) cyclopropyl)(morpholin-3-ylmethyl) carbamate [39] as a white solid (0.15 g, 88%, LCMS MH$^+$=377.2). $^1$H-NMR (400 MHz, DMSO-d$_6$): δ 9.11 (bs, 1H), 7.70-7.30 (m, 3H), 3.85 (d, J=11.20 Hz, 2H), 3.75-3.68 (m, 1H), 3.63 (bs, 3H), 3.60-3.40 (m, 4H), 3.24 (d, J=32.00 Hz, 1H), 3.10-3.00 (m, 1H), 1.53 (bs, 2H), 1.50-1.20 (m, 2H). HRMS calculated for: [C$_{17}$H$_{20}$F$_4$N203+H]+377.1483; found: 377.1475 (deviation 2.1 ppm).

Example [40]—Methyl (R)-(1-(4-fluoro-3-(trifluoromethyl)phenyl)cyclopropyl)((4-methylmorpholin-3-yl)methyl)carbamate The procedure used in Example [2], Step 2 was adapted such that 0.1 g of methyl (R)-(1-(4-fluoro-3-(trifluoromethyl)phenyl)cyclopropyl)(morpholin-3-ylmethyl)carbamate [39] was reacted to afford methyl (R)-(1-(4-fluoro-3-(trifluoromethyl)phenyl)cyclopropyl)((4-methylmorpholin-3-yl)methyl)carbamate [40] as a colourless gum (0.08 g, 85%, LCMS MH$^+$=391.2). $^1$H-NMR (400 MHz, DMSO-d$_6$): δ 7.54-7.44 (m, 3H), 3.61-3.58 (m, 3H), 3.47-3.39 (m, 2H), 3.34-3.33 (m, 2H), 3.30-3.26 (m, 1H), 3.20-3.10 (m, 1H), 2.67-2.61 (m, 1H), 2.27-2.07 (m, 5H), 1.46-1.25 (m, 4H). HRMS calculated for: [C$_{18}$H$_{22}$F$_4$N203+H]+391.1639; found: 391.1633 (deviation 1.7 ppm).

Example [41]—(R)—N-(1-(4-fluoro-3-(trifluoromethyl)phenyl)cyclopropyl)-N-(pyrrolidin-2-ylmethyl) methane sulfonamide Step 1

The procedure used in Example [1], Step 2 was adapted such that 0.25 g of tert-butyl (R)-2-(((1-(4-fluoro-3-(trifluoromethyl)phenyl)cyclopropyl)amino)methyl) pyrrolidine-1-carboxylate and 0.11 g of methanesulphonyl chloride were reacted to afford tert-butyl (R)-2-((N-(1-(4-fluoro-3-(trifluoromethyl)phenyl)cyclopropyl)methylsulfonamido)methyl) pyrrolidine-1-carboxylate [41.1] as a colourless gum (0.16 g, 34%, LCMS MH$^+$=381.1 (Boc-cleaved mass)).

Step 2

The procedure used in Example [22], Step 4 was adapted such that 0.15 g of tert-butyl (R)-2-((N-(1-(4-fluoro-3-(trifluoromethyl)phenyl)cyclopropyl)methylsulfonamido) methyl)pyrrolidine-1-carboxylate [41.1] was reacted to afford (R)—N-(1-(4-fluoro-3-(trifluoromethyl)phenyl)cyclopropyl)-N-(pyrrolidin-2-ylmethyl) methane sulfonamide [41] (HCl salt) as an off white solid (0.11 g, 84%, LCMS MH$^+$=381.1). $^1$H-NMR (400 MHz, DMSO-d$_6$): δ 9.27 (bs, 1H), 8.67 (bs, 1H), 7.80-7.75 (m, 2H), 7.52 (t, J=9.60 Hz, 2H), 3.65-3.56 (m, 3H), 3.22-3.12 (m, 2H), 2.90 (s, 3H), 2.00-1.75 (m, 3H), 1.70-1.50 (m, 3H), 1.30 (bs, 2H). HRMS calculated for: [C$_{16}$H$_{20}$F$_4$N$_2$O$_2$S+H]+381.1254; found: 381.1251 (deviation 0.7 ppm).

Example [42]—Methyl (S)-(1-(4-fluoro-3-(trifluoromethyl)phenyl)cyclopropyl)(morpholin-3-ylmethyl) carbamate Step 1

The procedure used in Example [2], Step 2 was adapted such that 0.8 g of 1-(4-fluoro-3-(trifluoromethyl)phenyl) cyclopropan-1-amine [1.1] was reacted with tert-butyl (3R)-3-formylmorpholine-4-carboxylate to afford tert-butyl (S)-3-(((1-(4-fluoro-3-(trifluoromethyl)phenyl)cyclopropyl) amino)methyl)morpholine-4-carboxylate [42.1] as a colourless gum (0.9 g, 59%, LCMS MH$^+$=419.2).

Step 2

The procedure used in Example [1], Step 2 was adapted such that 0.3 g of tert-butyl (S)-3-(((1-(4-fluoro-3-(trifluoromethyl)phenyl)cyclopropyl)amino)methyl)morpholine-4-carboxylate [42.1] was reacted to afford tert-butyl(S)-3-(((1-(4-fluoro-3-(trifluoromethyl)phenyl)cyclopropyl) (methoxycarbonyl)amino)methyl)morpholine-4-carboxylate [42.2] as a colourless gum (0.17 g, 50%, LCMS MH$^+$=377.2).

Step 3

The procedure used in Example [2], Step 4 was adapted such that 0.17 g of tert-butyl (S)-3-(((1-(4-fluoro-3-(trifluoromethyl)phenyl)cyclopropyl)(methoxycarbonyl)amino) methyl)morpholine-4-carboxylate [42.2] was reacted to afford methyl (S)-(1-(4-fluoro-3-(trifluoromethyl)phenyl) cyclopropyl)(morpholin-3-ylmethyl) carbamate [42] as a white solid (0.135 g, 92%; LCMS MH$^+$=377.2). $^1$H-NMR (400 MHz, DMSO-d$_6$): δ 9.15 (bs, 2H), 7.50-7.37 (m, 3H), 3.86 (d, J=11.60 Hz, 2H), 3.75-3.40 (m, 8H), 3.25 (d, J=40.00 Hz, 1H), 3.12-2.95 (m, 1H), 1.57 (bs, 2H), 1.31-1.23 (m, 2H). HRMS calculated for: [C$_{17}$H$_{20}$F$_4$N203+H]+ 377.1483; found: 377.1476 (deviation 1.9 ppm).

Example [43]—Methyl (S)-(1-(4-fluoro-3-(trifluoromethyl)phenyl)cyclopropyl)((4-methylmorpholin-3-yl)methyl)carbamate The procedure used in Example [2], Step 2 was adapted such that 0.1 g of methyl (S)-(1-(4-fluoro-3-(trifluoromethyl)phenyl)cyclopropyl)(morpholin-3-ylmethyl)carbamate [42] was reacted to afford methyl (S)-(1-(4-fluoro-3-(trifluoromethyl)phenyl)cyclopropyl)((4-methylmorpholin-3-yl)methyl)carbamate [43] as a white solid (0.075 g, 80%, LCMS MH$^+$=391.2). $^1$H-NMR (400 MHz, DMSO-d$_6$): δ

7.52-7.42 (m, 3H), 3.70-3.55 (m, 5H), 3.53-3.37 (m, 2H), 3.35-3.22 (m, 1H), 3.00-3.02 (m, 1H), 2.68-2.58 (m, 1H), 2.35-2.18 (m, 4H), 2.15-2.05 (m, 1H), 1.55-1.33 (m, 4H). HRMS calculated for: [$C_{18}H_{22}F_4N_2O_3$+H]+391.1639; found: 391.1633 (deviation 1.7 ppm).

Example [44]—Isopropyl (S)-(1-(4-fluoro-3-(trifluoromethyl)phenyl)cyclopropyl)(pyrrolidin-2-ylmethyl)carbamate Step 1

The procedure used in Example [45], Step 1 was adapted such that 0.1 g of tert-butyl (S)-2-(((1-(4-fluoro-3-(trifluoromethyl)phenyl)cyclopropyl)amino)methyl)pyrrolidine-1-carboxylate [23.2] and 0.67 g of isopropyl chloroformate were reacted to afford tert-butyl (S)-2-(((1-(4-fluoro-3-(trifluoromethyl)phenyl)cyclopropyl)(isopropoxycarbonyl)amino)methyl)pyrrolidine-1-carboxylate [44.1] as colourless liquid (0.1 g, 83%).

Step 2

The procedure used in Example [26], Step 2 was adapted such that 0.1 g of tert-butyl (S)-2-(((1-(4-fluoro-3-(trifluoromethyl)phenyl)cyclopropyl)(isopropoxy carbonyl)amino)methyl)pyrrolidine-1-carboxylate [44.1] was reacted to afford isopropyl (S)-(1-(4-fluoro-3-(trifluoromethyl)phenyl)cyclopropyl)(pyrrolidin-2-ylmethyl)carbamate [44] as a pale yellow liquid (0.07 g, 88%). $^1$H-NMR (400 MHz, DMSO-$d_6$): δ 8.45 (bs, 1H), 7.57 (d, J=2.64 Hz, 1H), 7.48 (t, J=8.24 Hz, 2H), 4.83 (t, J=6.24 Hz, 1H), 3.70-3.48 (m, 3H), 3.28-3.18 (m, 1H), 3.12-3.02 (m, 1H), 1.99 (bs, 1H), 1.92-1.74 (m, 2H), 1.60-1.38 (m, 3H), 1.38-1.24 (m, 2H), 1.22-1.05 (m, 6H). HRMS calculated for: [$C_{19}H_{24}F_4N_2O_2$+H]+389.1847; found: 389.1838 (deviation 2.3 ppm).

Example [45]—Cyclopropyl (S)-(1-(4-fluoro-3-(trifluoromethyl)phenyl)cyclopropyl)(pyrrolidin-2-ylmethyl)carbamate Step 1

To a stirred solution of tert-butyl (S)-2-(((1-(4-fluoro-3-(trifluoromethyl)phenyl)cyclopropyl)amino)methyl)pyrrolidine-1-carboxylate [23.2] (0.15 g, 0.37 mmol) in acetonitrile (4 mL) was added cesium carbonate (0.36 g, 1.12 mmol) and cyclopropane chloroformate (0.09 g, 0.75 mmol). The reaction was stirred at room temperature for 3 h, filtered and concentrated to afford the crude product, which was purified by flash column chromatography using ethyl acetate in pet ether as eluent to afford tert-butyl (S)-2-(((cyclopropoxycarbonyl)(1-(4-fluoro-3-(trifluoromethyl)phenyl)cyclopropyl)amino)methyl)pyrrolidine-1-carboxylate [45.1] as a colourless liquid (0.16 g, 89%, LCMS MH+=387.1 (boc cleaved mass)).

Step 2

The procedure used in Example [26], Step 2 was adapted such that 0.16 g of tert-butyl (S)-2-(((cyclopropoxycarbonyl)(1-(4-fluoro-3-(trifluoromethyl)phenyl)cyclopropyl)amino)methyl)pyrrolidine-1-carboxylate [45.1] was reacted to afford cyclopropyl (S)-(1-(4-fluoro-3-(trifluoromethyl)phenyl)cyclopropyl)(pyrrolidin-2-ylmethyl)carbamate [45] as a yellow liquid (0.1 g, 83%). $^1$H-NMR (400 MHz, DMSO-$d_6$): δ 7.43-7.41 (m, 3H), 3.50-3.00 (m, 3H), 2.90-2.70 (m, 1H), 1.80-1.50 (m, 4H), 1.40-1.10 (m, 5H), 0.80-0.30 (m, 4H). HRMS calculated for: [$C_{19}H_{22}F_4N_2O_2$+H]+387.1690; found: 387.1688 (deviation 0.5 ppm).

Example [46]—Methyl (R)-(1-(4-fluoro-3-(trifluoromethyl)phenyl)cyclopropyl)((2-methyl pyrrolidin-2-yl)methyl)carbamate Step 1

The procedure used in Example [2], Step 2 was adapted such that 0.7 g of 1-(4-fluoro-3-(trifluoromethyl)phenyl) cyclopropan-1-amine [1.1] and tert-butyl (2R)-2-formyl-2-methylpyrrolidine-1-carboxylate were reacted to afford tert-butyl (R)-2-(((1-(4-fluoro-3-(trifluoromethyl)phenyl)cyclopropyl)amino)methyl)-2-methyl pyrrolidine-1-carboxylate [46.1] as a colourless liquid (0.68 g, 51%, LCMS MH+=417.2).

Step 2

The procedure used in Example [1], Step 2 was adapted such that 0.5 g of tert-butyl (R)-2-(((1-(4-fluoro-3-(trifluoromethyl)phenyl)cyclopropyl)amino)methyl)-2-methylpyrrolidine-1-carboxylate [46.1] was reacted to afford tert-butyl (R)-2-(((1-(4-fluoro-3-(trifluoromethyl)phenyl)cyclopropyl)(methoxycarbonyl)amino)methyl)-2-methylpyrrolidine-1-carboxylate [46.2] as a brown liquid (0.13 g, 22%, LCMS MH+=375.1(boc-cleaved mass)).

Step 3

The procedure used in Example [22], Step 4 was adapted such that 0.15 g of tert-butyl (R)-2-(((1-(4-fluoro-3-(trifluoromethyl)phenyl)cyclopropyl)(methoxycarbonyl)amino)methyl)-2-methylpyrrolidine-1-carboxylate [46.2] was reacted to afford methyl (R)-(1-(4-fluoro-3-(trifluoromethyl)phenyl)cyclopropyl)((2-methyl pyrrolidin-2-yl)methyl)carbamate [46] as colourless gum (0.125 g, 96%, LCMS MH+=375.4). $^1$H-NMR (400 MHz, DMSO-$d_6$): δ 8.64 (bs, 1H), 8.40 (bs, 1H), 7.59-7.48 (m, 3H), 3.84 (bs, 1H), 3.68 (bs, 3H), 3.60 (bs, 1H), 3.24-3.22 (m, 3H), 2.00-1.85 (m, 2H), 1.77 (bs, 2H), 1.95 (bs, 3H), 1.32-1.20 (m, 1H), 1.10 (bs, 2H). HRMS calculated for: [$C_{18}H_{22}F_4N_2O_2$+H]+375.1690; found: 375.1684 (deviation 1.8 ppm).

Example [47]—N-((1-amino cyclopropyl)methyl)-1-(4-fluoro-3-(trifluoromethyl)phenyl)cyclopropan-1-amine The procedure used in Example [2], Step 4 was adapted such that 0.1 g of tert-butyl (1-(((1-(4-fluoromethyl)phenyl)cyclopropyl)amino)methyl)cyclopropyl)carbamate [3.1] was reacted to afford N-((1-amino cyclopropyl)methyl)-1-(4-fluoro-3-(trifluoromethyl)phenyl) cyclopropan-1-amine [47] as a white solid (0.08 g, 96%, LCMS MH+=288.1). $^1$H-NMR (400 MHz, DMSO-$d_6$): δ 10.60-10.20 (m, 2H), 8.90-8.65 (m, 2H), 8.20-7.90 (m, 2H), 7.65-7.55 (m, 1H), 3.30-3.10 (m, 2H), 1.75-1.55 (m, 2H), 1.35-1.15 (m, 2H), 1.14-0.80 (m, 4H). HRMS calculated for: [$C_{14}H_{16}F_4N_2$+H]+289.1322; found: 289.1310 (deviation 4.2 ppm).

Example [48]—Cyclopropylmethyl (S)-(1-(4-fluoro-3-(trifluoromethyl)phenyl)cyclopropyl)(pyrrolidin-2-ylmethyl)carbamate Step 1

The procedure used in Example [45], Step 1 was adapted such that 0.15 g of tert-butyl (S)-2-(((1-(4-fluoro-3-(trifluoromethyl)phenyl)cyclopropyl)amino)methyl)pyrrolidine-1-carboxylate [23.2] and 0.125 g of cyclopropylmethyl chloroformate were reacted to afford tert-butyl (S)-2-((((cyclopropylmethoxy)carbonyl) (1-(4-fluoro-3-(trifluoromethyl)phenyl)cyclopropyl)amino)methyl)pyrrolidine-1-carboxylate [48.1] (0.25 g, 80%).

Step 2

The procedure used in Example [26], Step 2 was adapted such that 0.12 g of tert-butyl (S)-2-((((cyclopropylmethoxy)carbonyl)(1-(4-fluoro-3-(trifluoromethyl)phenyl)cyclopropyl)amino)methyl)pyrrolidine-1-carboxylate [48.1] was reacted to afford cyclopropylmethyl (S)-(1-(4-fluoro-3-(trifluoromethyl)phenyl)cyclopropyl)(pyrrolidin-2-ylmethyl)carbamate [48] as a yellow liquid (0.085 g, 88%). $^1$H-NMR (400 MHz, DMSO-d$_6$): δ 7.52-7.43 (m, 3H), 3.87 (d, J=7.00 Hz, 2H), 3.55-3.45 (m, 3H), 3.00-2.53 (m, 2H), 4.80-1.55 (m, 4H), 1.45-1.20 (m, 4H), 1.00 (s, 1H), 0.45 (s, 2H), 0.20 (s, 2H). HRMS calculated for: [C$_{20}$H$_{24}$F$_4$N2O2+H]+ 401.1847; found: 401.1845 (deviation 0.3 ppm).

Example [49]—N-((1-aminocyclopropyl)methyl)-N-(1-(4-fluoro-3-(trifluoromethyl)-phenyl)cyclopropyl)methanesulfonamide Step 1

The procedure used in Example [1], Step 2 was adapted such that 0.3 g of tert-butyl (1-(((1-(4-fluoro-3-(trifluoromethyl)phenyl)cyclopropyl)amino)methyl)cyclopropyl)carbamate [3.1] and 0.13 g of methanesulfonyl chloride were reacted to afford tert-butyl (1-((N-(1-(4-fluoro-3-(trifluoromethyl)phenyl)cyclopropyl)methylsulfonamido)methyl)cyclopropyl)carbamate [49.1] as a white solid (0.3 g, 83%, LCMS MH+=367.2).

Step 2

The procedure used in Example [2], Step 4 was adapted such that 0.1 g of tert-butyl (1-((N-(1-(4-fluoro-3-(trifluoromethyl)phenyl)cyclopropyl)methylsulfonamido)methyl)cyclopropyl)carbamate [49.1] was reacted to afford N-((1-aminocyclopropyl)methyl)-N-(1-(4-fluoro-3-(trifluoromethyl)phenyl)cyclopropyl)methanesulfonamide [49] as a white solid (0.08 g, 93%, LCMS MH+=367.2). $^1$H-NMR (400 MHz, DMSO-d$_6$): δ 8.41 (bs, 3H), 7.76 (s, 1H), 7.66 (d, J=4.96 Hz, 1H), 7.49 (t, J=8.80 Hz, 1H), 3.53 (s, 2H), 3.01 (s, 3H), 1.67 (bs, 2H), 1.33 (s, 2H), 0.92 (d, J=44.32 Hz, 4H). HRMS calculated for: [C$_{15}$H$_{18}$F$_4$N2O2S+H]+367.1098; found: 367.1089 (deviation 2.5 ppm).

Example [50]—Methyl (S)-(1-(4-fluoro-3-(trifluoromethyl)phenyl)cyclopropyl)((2-methylpyrrolidin-2-yl)methyl)carbamate Step 1

The procedure used in Example [2], Step 2 was adapted such that 0.5 g of 1-(4-fluoro-3-(trifluoromethyl)phenyl)cyclopropan-1-amine [1.1] and tert-butyl (2S)-2-formyl-2-methylpyrrolidine-1-carboxylate were reacted to afford tert-butyl (S)-2-(((1-(4-fluoro-3-(trifluoromethyl)phenyl)cyclopropyl)amino)methyl)-2-methylpyrrolidine-1-carboxylate [50.1] as a colourless liquid (0.65 g, 68%, LCMS MH+=417.2).

Step 2

The procedure used in Example [1], Step 2 was adapted such that 0.4 g of tert-butyl (S)-2-(((1-(4-fluoro-3-(trifluoromethyl)phenyl)cyclopropyl)amino)methyl)-2-methylpyrrolidine-1-carboxylate [50.1] was reacted to afford tert-butyl (S)-2-(((1-(4-fluoro-3-(trifluoromethyl)phenyl)cyclopropyl)(methoxycarbonyl)amino)methyl)-2-methylpyrrolidine-1-carboxylate [50.2] as a brown liquid (0.32 g, 70%, LCMS MH+=375.1(boc-cleaved mass)).

Step 3

The procedure used in Example [22], Step 4 was adapted such that 0.3 g of tert-butyl (S)-2-(((1-(4-fluoro-3-(trifluoromethyl)phenyl)cyclopropyl)(methoxycarbonyl)amino)methyl)-2-methylpyrrolidine-1-carboxylate [50.2] was reacted to afford methyl (S)-(1-(4-fluoro-3-(trifluoromethyl)phenyl)cyclopropyl)((2-methylpyrrolidin-2-yl)methyl)carbamate [50] as a white solid (0.25 g, 96%, LCMS MH+=375.0). $^1$H-NMR (400 MHz, DMSO-d$_6$): δ 8.70 (bs, 1H), 8.46 (bs, 1H), 7.52 (q, J=9.68 Hz, 3H), 3.81 (t, J=45.48 Hz, 4H), 3.22 (d, J=6.84 Hz, 2H), 1.95 (d, J=8.36 Hz, 2H), 1.92 (d, J=5.52 Hz, 2H), 1.44 (s, 3H), 1.27 (bs, 2H), 1.10 (s, 3H). HRMS calculated for: [C$_{18}$H$_{20}$F$_4$N2O2+H]+375.1690; found: 375.1688 (deviation 0.6 ppm).

Example [51]—(1S, 2S)—N1-(1-(4-fluoro-3-(trifluoromethyl)phenyl)cyclopropyl)-cyclopentane-1,2-diamine Step 1

The procedure used in Example [2], Step 2 was adapted such that 0.8 g of 1-(4-fluoro-3-(trifluoromethyl)phenyl)cyclopropan-1-amine [1.1] and tert-butyl N-[(1S)-2-oxocyclopentyl]carbamate were reacted to afford the diastereomers tert-butyl ((1S,2S)-2-((1-(4-fluoro-3-(trifluoromethyl)phenyl)cyclopropyl)amino)cyclopentyl)carbamate [51.1] as yellow gum (0.43 g, 58%, LCMS MH*=403.2) and tert-butyl ((1S,2R)-2-((1-(4-fluoro-3-(trifluoromethyl)phenyl)cyclopropyl)amino)cyclopentyl)carbamate [51.2] as a white solid (0.31 g, 42%, LCMS MH+=403.2).

Step 2

The procedure used in Example [22], Step 4 was adapted such that 0.04 g of tert-butyl ((1S,2S)-2-((1-(4-fluoro-3-(trifluoromethyl)phenyl)cyclopropyl)amino)cyclopentyl)carbamate [51.1] was reacted to afford (1S, 2S)—N1-(1-(4-fluoro-3-(trifluoromethyl)phenyl)cyclopropyl)cyclopentane-1,2-diamine [51] as a brown gum (0.012 g, 35%, LCMS MH+=303.2). $^1$H-NMR (400 MHz, DMSO-d$_6$): δ 7.93 (t, J=22.80 Hz, 2H), 7.51 (t, J=9.20 Hz, 1H), 3.54 (d, J=1.60 Hz, 2H), 3.40 (d, J=6.80 Hz, 2H), 3.15 (t, J=1.20 Hz, 1H), 2.00-1.88 (m, 2H), 1.63-1.55 (m, 3H), 1.63-1.55 (m, 5H). HRMS calculated for: [C$_{15}$H$_{18}$F$_4$N2+H]+ 303.1479; found: 303.1472 (deviation 2.3 ppm).

Example [52]—(1R,2S)—N1-(1-(4-fluoro-3-(trifluoromethyl)phenyl)cyclopropyl)-cyclopentane-1,2-diamine Step 1

The procedure used in Example [22], Step 4 was adapted such that 0.15 g of tert-butyl ((1S,2R)-2-((1-(4-fluoro-3-(trifluoromethyl)phenyl)cyclopropyl)amino)cyclopentyl)carbamate [51.2] was reacted to afford (1R,2S)—N1-(1-(4-fluoro-3-(trifluoromethyl)phenyl)cyclopropyl)cyclopentane-1,2-diamine [52] as an off-white solid (0.112 g, 88%, LCMS MH+=303.2). $^1$H-NMR (400 MHz, DMSO-d$_6$): δ 10.66 (bs, 1H), 8.80-8.30 (m, 1H), 8.30-7.60 (m, 3H), 7.70-7.45 (m, 1H), 7.39-7.14 (m, 1H), 4.50-3.80 (m, 2H), 3.80-3.55 (m, 1H), 2.00-1.50 (m, 6H), 1.50-1.05 (m, 5H). HRMS calculated for: [C$_{15}$H$_{18}$F$_4$N2+H]+303.1479; found: 303.1474 (deviation 1.6 ppm).

Example [53]—Methyl (S)-(azetidin-2-ylmethyl)(1-(4-fluoro-3-(trifluoromethyl)phenyl)-cyclopropyl)carbamate Step 1

The procedure used in Example [39], Step 1 was adapted such that 1.3 g of 1-(4-fluoro-3-(trifluoromethyl)phenyl)cyclopropan-1-amine [1.1] was reacted to afford tert-butyl (S)-2-((1-(4-fluoro-3-(trifluoromethyl)phenyl)cyclopropyl)

carbamoyl)azetidine-1-carboxylate [53.1] as a brown liquid (2.2 g, 92%, LCMS MH+=303.1(boc-cleaved mass)).
Step 2
The procedure used in Example [32], Step 2 was adapted such that 2.2 g of tert-butyl (S)-2-((1-(4-fluoro-3-(trifluoromethyl)phenyl)cyclopropyl)carbamoyl)azetidine-1-carboxylate [53.1] was reacted to afford tert-butyl (S)-2-(((1-(4-fluoro-3-(trifluoromethyl)phenyl)cyclopropyl)amino)methyl)azetidine-1-carboxylate [53.2] as colourless liquid (1.2 g, 57%, LCMS MH+=389.2).
Step 3
The procedure used in Example [1], Step 2 was adapted such that 0.25 g of tert-butyl (S)-2-(((1-(4-fluoro-3-(trifluoromethyl)phenyl)cyclopropyl)amino)methyl)azetidine-1-carboxylate [53.2] was reacted to afford tert-butyl (S)-2-(((1-(4-fluoro-3-(trifluoromethyl)phenyl)cyclopropyl)(methoxycarbonyl)amino)methyl)azetidine-1-carboxylate [53.3] as a brown gum (0.26 g, 92%, LCMS MH+=447.2).
Step 4
The procedure used in Example [26], Step 2 was adapted such that 0.5 g of tert-butyl (S)-2-(((1-(4-fluoro-3-(trifluoromethyl)phenyl)cyclopropyl)(methoxycarbonyl)amino)methyl)azetidine [53.3] was reacted to afford methyl (S)-(azetidin-2-ylmethyl)(1-(4-fluoro-3-(trifluoromethyl)phenyl)cyclopropyl)carbamate [53] as a brown liquid (0.04 g, 11%, LCMS MH+=347.0). $^1$H-NMR (400 MHz, DMSO-$d_6$): δ 7.44-7.28 (m, 3H), 3.91 (s, 1H), 3.58-3.33 (m, 5H), 3.05 (s, 2H), 2.00 (t, J=43.60 Hz, 1H), 1.76 (s, 2H), 1.39 (s, 2H), 1.24 (s, 2H). HRMS calculated for: [$C_{16}H_{18}F_4N_2O2$+H]+347.1377; found: 347.1369 (deviation 2.4 ppm).

Example [54]—Solubility of Compounds

The aim of this experiment was to determine solubility of test compounds in 50 mM Phosphate buffer by using HPLC.

Method

| | |
|---|---|
| Incubation time | 16 hr at ~25° C. |
| Buffer pH | 50 mM potassium phosphate buffer, pH 7.40 |
| Test compound | 1600 μM |
| Incubation concentration | |
| Replicates | n = 2 |
| Analysis | HPLC |
| Standard compounds | Caffeine [Solubility (1400-1900 μM)], Diethylstilbestrol [Solubility (0 μM)] and Tamoxifen [Solubility (<20 μM)] |
| Deliverables | Solubility of test compound mg/mL |

Preparation of Phosphate Buffer (pH 7.4):
2.79 g of $K_2HPO_4$ and 0.54 g of $KH_2PO_4$ was dissolved in 390 mL of milliQ water. pH was adjusted to 7.4 using 1N HCl/1N NaOH and final volume was made up to 400 mL with milliQ water.
Preparation and Dilution of Test Compound:
80 mM master stock of test compounds was prepared in 100% DMSO. In case of compounds not soluble/less quantity submission, 40/20/10Mm stocks were prepared and used for experiment.
Assay Procedure:
  245 μL of 50 mM phosphate buffer then 5 μL each of test compound/standards (80 mM) in their respective positions was added to the 1.1 mL 96 well plate.
  DMSO Controls was prepared by taking 245 μL of 100% DMSO then 5 μL each of test compound in their respective positions and added to the 1.1 mL 96 well plate.
  Plate was incubated with mixing at 1600 RPM for 16 hours at room temperature (~23° C.).
After incubation, samples were filtered using Millipore plates.
Filtrates were analysed by HPLC-UV.
Solubility Calculation:
Solubility is calculated using the following formula:

$$\text{Solubility }(\mu M) = \frac{\text{(Sample area in Buffer)}}{\text{(Sample area in } DMSO)} \times 1600$$

Results

| | Measured Solubility in pH 7.4 phosphate buffer | |
|---|---|---|
| Compound | (mg/ml) | (μM) (rounded) |
| [1] | 0.5409 | 1600 |
| [2] | 0.5555 | 1600 |
| [3] | 0.5599 | 1600 |
| [4] | 0.0279 | 100 |
| [6] | 0.6792 | 1500 |
| [8] | 0.5109 | 1500 |
| [9] | 0.582 | 1200 |
| [10] | 0.4809 | 1400 |
| [11] | 0.5778 | 1600 |
| [12] | 0.3755 | 800 |
| [13] | 0.6337 | 1500 |
| [14] | 0.7554 | 1600 |
| [15] | 0.526 | 1400 |
| [16] | 0.5974 | 1600 |
| [17] | 0.5636 | 1500 |
| [19] | 0.607 | 1500 |
| [20] | 0.5836 | 1500 |
| [21] | 0.5646 | 1500 |
| [22] | 0.6666 | 1700 |
| [23] | 0.653 | 1600 |
| [24] | 0.5958 | 1500 |
| [25] | 0.4824 | 1700 |
| [26] | 0.6868 | 1500 |
| [27] | 0.5918 | 1600 |
| [28] | 0.6738 | 1600 |
| [29] | 0.6773 | 1600 |
| [30] | 0.5984 | 1700 |
| [31] | 0.5575 | 1500 |
| [32] | 0.5578 | 1500 |
| [33] | 0.1375 | 400 |
| [34] | 0.594 | 1400 |
| [35] | 0.5679 | 1500 |
| [36] | 0.3218 | 800 |
| [37] | 0.621 | 1600 |
| [38] | 0.6157 | 1500 |
| [42] | 0.6118 | 1500 |
| [43] | 0.5996 | 1500 |
| [44] | 0.6148 | 1600 |
| [45] | 0.6009 | 1600 |
| [46] | 0.585 | 1400 |
| [47] | 0.4635 | 1400 |
| [50] | 0.5747 | 1400 |
| [51] | 0.2392 | 700 |
| [52] | 0.4797 | 1400 |
| [53] | 0.5907 | 1700 |
| NS6180 | 0.0009 | 2.8 |

Conclusion

It is demonstrated that the tested compounds have solubility in pH 7.4 phosphate buffer of 400 to 1700 μM, whereas NS6180 has a solubility of 2.8 μM.

Example [55]—Inhibition of $K_{Ca}3.1$

Erythrocyte $K_{Ca}3.1$ Assay

Human blood was drawn from healthy human volunteers in a standard heparinized blood sampling vial (Vacutainer, Li/heparin, BD Bioscience, Plymouth, UK). The erythrocytes were packed by centrifugation, and the plasma and buffy coat were removed by aspiration. Erythrocytes were washed three times in the experimental salt solution and then stored at 0° C. until use. Blood samples from NMRI mice or from Wistar rats were treated similarly. The methodological principle is outlined in Macey et al. (1978) and further described in Strøbæk et al. (2013). Activation of the erythrocyte $K_{Ca}3.1$ channels were obtained by addition of the $Ca^{2+}$ ionophore A23187, which causes synchronized hyperpolarization, which is reported as a CCCP-mediated shift in the unbuffered extracellular pH of the erythrocyte suspension. Standard procedure: 3 mL unbuffered experimental salt solution (in mM: 2 KCl, 154 NaCl, 0.05 $CaCl_2$)) was heated to 37° C. with stirring. Packed erythrocytes were added (50 µL, final cytocrit 1.5%), and the extracellular pH ($pH_o$) followed with a glass/calomel (pHG200-8/REF200, Radiometer, Denmark) electrode pair. CCCP (3 µL, final concentration 20 µM) was added followed by varying concentrations of test compounds (DMSO concentration constant). After pH stabilization at ~7.2, A23187 (3 µL, final concentration 0.33 µM) was added to initiate the experiment. After the peak hyperpolarization was attained, the intracellular pH ($pH_i$ constant during the experiment) was found by haemolysing the erythrocytes via addition of 100 µL of Triton-X100.

The erythrocyte membrane potential, $V_m$, was calculated according to:

$$V_m = -61.5 \text{ mV} \times (pH_o - pH_i)$$

and the fractional remaining $Ca^{2+}$-activated $K^+$-conductance at the concentration C of blocker, $fG_K(C)$, was calculated from $$fG_K(C) = \frac{(V_m(0) - E_K) * (E_{Cl} - V_m(C))}{(E_{Cl} - V_m(0)) * (V_m(C) - E_K)}$$

where the $K^+$ equilibrium potential $E_K = -107$ mV, the $Cl^-$ equilibrium potential $E_{Cl} = -12$ mV and the $V_m(0)$ and $V_m(C)$ are the peak hyperpolarizations in the control and in the presence of a concentration of C of blocker respectively.

$IC_{50}$ values for compounds were calculated from a plot of $fG_K(C)$ versus C by a fit to the Hill equation, using a custom program written in the IGOR-Pro software (WaveMetrics, Lake Oswego, OR, USA). All $IC_{50}$-values are reported in µM.

Results

| Compound | RBC K (in vitro) Human $IC_{50}$ (µM) |
|---|---|
| [1] | 0.33 |
| [2] | 0.086 |
| [3] | 0.16 |
| [4] | 0.071 |
| [5] | 0.31 |
| [6] | 0.19 |
| [7] | 0.48 |
| [8] | 0.014 |
| [9] | 0.35 |
| [10] | 0.024 |
| [11] | 0.3 |
| [12] | 0.4 |
| [13] | 0.44 |
| [14] | 0.25 |
| [15] | 0.14 |
| [16] | 0.4 |
| [17] | 0.4 |
| [18] | 0.018 |
| [19] | 0.047 |
| [20] | 0.092 |
| [21] | 0.075 |
| [22] | 0.21 |
| [23] | 0.12 |
| [24] | 0.31 |
| [25] | 0.18 |
| [26] | 0.21 |
| [27] | 0.3 |
| [28] | 0.087 |
| [29] | 0.33 |
| [30] | 0.17 |
| [31] | 0.081 |
| [32] | 0.27 |
| [33] | 0.12 |
| [34] | 0.052 |
| [35] | 0.11 |
| [36] | 0.32 |
| [37] | 0.14 |
| [38] | 0.12 |
| [39] | 0.42 |
| [40] | 0.27 |
| [41] | 0.38 |
| [42] | 0.34 |
| [43] | 0.29 |
| [44] | 0.2 |
| [45] | 0.18 |
| [46] | 0.1 |
| [47] | 0.22 |
| [48] | 0.23 |
| [49] | 0.39 |
| [50] | 0.15 |
| [51] | 0.41 |
| [52] | 0.093 |
| [53] | 0.36 |

Conclusion

It is demonstrated that all the compounds inhibit $K_{Ca}3.1$.

REFERENCES

Macey et al., Biochim. Biophys. Acta 1978, 22, 512(2), 284-95

Strøbæk et al., Br. J. Pharmacol. 2013, 168(2), 432-444

WO 2014/001363 [Clevexel Pharma; Aniona ApS; Saniona ApS]

WO 2013/191984 [Boehringer Ingelheim]

WO 2014/067861 [Hoffmann La Roche]

The invention claimed is:

1. A method for treating inflammatory bowel disease (IBD), hereditary xerocytosis, acute respiratory distress syndrome (ARDS), or a combination thereof, in a subject in need thereof, comprising administering to the subject a compound of any of the following formulae:

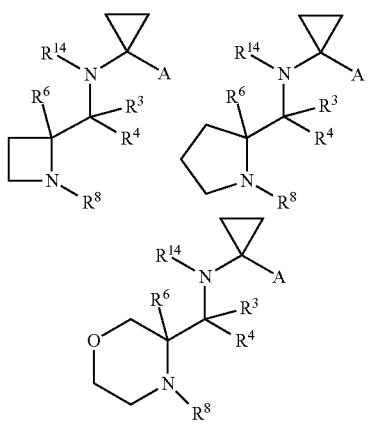

wherein:
- R$^{14}$ is selected from the group consisting of —C(O)—C$_{1-8}$ linear or branched alkyl optionally substituted with cyclopropyl; —C(O)—O—C$_{1-8}$ linear or branched alkyl optionally substituted with cyclopropyl; —C$_{2-8}$ linear or branched alkyl optionally substituted with —OH; —H and —S(O)$_2$—C$_{1-8}$ linear or branched alkyl;
- R$^3$ is H or C$_{1-5}$ linear or branched alkyl;
- R$^4$ is H, C$_{1-5}$ linear or branched alkyl;
- R$^6$ is H or C$_{1-5}$ linear or branched alkyl;
- R$^8$ is selected from the group consisting of H, C$_{1-5}$ linear or branched alkyl, and —C(O)—O—C$_{1-8}$ linear or branched alkyl;
- A is a phenyl or a pyridinyl, wherein the phenyl or pyridinyl is optionally substituted with one or more substituents R$^{13}$ individually selected from the group consisting of halogen, —CX$_3$, —OCX$_3$, —CHX$_2$, —OCHX$_2$, —CH$_2$CX$_3$, and OCH$_2$CX$_3$; and
- X is halogen;

or a pharmaceutically acceptable salt thereof.

2. The method according to claim 1, wherein A is a moiety of formula (IX):

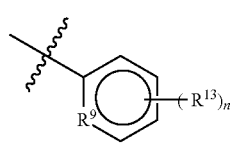

Formula (IX)

wherein:
- R$^9$ is —C(H)—, —N—, or —C(R$^{13}$)—;
- R$^{13}$ is, individually, selected from the group consisting of halogen, —CX$_3$, —OCX$_3$, —CHX$_2$, —OCHX$_2$, —CH$_2$CX$_3$, and OCH$_2$CX$_3$;
- n is an integer of 0 to 4; and
- X is halogen.

3. The method according to claim 1, wherein A is a moiety of formula (X):

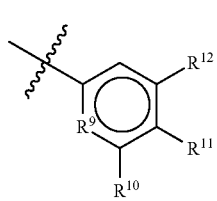

Formula (X)

wherein:
- R$^9$ is —C(H)—, —N—, or —C(R$^{13}$)—;
- R$^{10}$, R$^{11}$, R$^{12}$, and R$^{13}$ are, individually, selected from the group consisting of H, halogen, —CX$_3$, —OCX$_3$, —CHX$_2$, —OCHX$_2$, —CH$_2$CX$_3$, and OCH$_2$CX$_3$; and
- X is halogen.

4. The method according to claim 3, wherein R$^9$ is —C(H)— or —N—;
R$^{10}$ is H or halogen;
R$^{11}$ is H or halogen; R$^{12}$ is —CX$_3$, —OCX$_3$, H, or halogen; and X is halogen.

5. The method according to claim 1, wherein R$^6$ is H.

6. The method according to claim 1, wherein the compound is of the following formula:

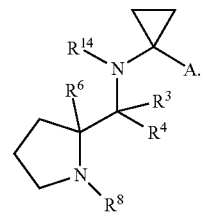

7. The method according to claim 1, wherein the compound is of formula (XIX):

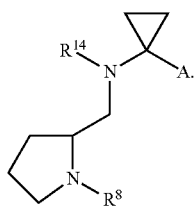

Formula (XIX)

8. The method according to claim 1, wherein the compound is of the following formula:

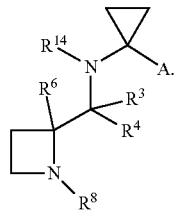

9. The method according to claim 1, wherein the compound is of the following formula:

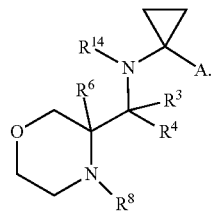

10. The method according to claim 1, wherein $R^8$ is H or $CH_3$.

11. The method according to claim 1, wherein $R^{14}$ is —C(O)—$OC_{1-4}$ alkyl.

12. The method according to claim 1, wherein $R^{14}$ is $C_{3-4}$ alkyl.

13. The method according to claim 3, wherein $R^{12}$ is —$CF_3$, —$OCF_3$, or a halogen.

14. The method according to claim 3, wherein $R^9$ is —C(H)—, $R^{10}$ is H, $R^{11}$ is F and $R^{12}$ is —$CF_3$.

15. The method according to claim 1, wherein the compound is selected from the group consisting of:

1-((azetidin-2-ylmethyl)(1-(4-fluoro-3-(trifluoromethyl)phenyl)cyclopropyl)amino)-2-methyl propan-2-ol;
1-((1-(4-fluoro-3-(trifluoromethyl)phenyl)cyclopropyl)((1-methylazetidin-2-yl)methyl)amino)-2-methylpropan-2-ol;
Methyl (R)-(1-(4-fluoro-3-(trifluoromethyl)phenyl)cyclopropyl)(pyrrolidin-2-ylmethyl) carbamate;
Methyl(S)-(1-(4-fluoro-3-(trifluoromethyl)phenyl)cyclopropyl)(pyrrolidin-2-ylmethyl) carbamate;
Methyl (azetidin-2-ylmethyl)(1-(4-fluoro-3-(trifluoromethyl)phenyl)cyclopropyl) carbamate;
Methyl(S)-(1-(4-fluoro-3-(trifluoro methyl)phenyl)cyclopropyl)((1-methylpyrrolidin-2-yl)methyl)carbamate;
Methyl(S)-(1-(4-fluoro-3-(trifluoromethoxy)phenyl)cyclopropyl)(pyrrolidin-2-ylmethyl)carbamate;
Methyl (R)-(1-(4-fluoro-3-(trifluoromethoxy)phenyl)cyclopropyl)(pyrrolidin-2-ylmethyl)carbamate;
Methyl (1-(4-fluoro-3-(trifluoromethyl)phenyl)cyclopropyl)((1-methylazetidin-2-yl)methyl)carbamate;
Methyl (R)-(1-(4-fluoro-3-(trifluoromethyl)phenyl)cyclopropyl)((1-methylpyrrolidin-2-yl)methyl)carbamate;
Methyl (azetidin-2-ylmethyl)(1-(4-fluoro-3-(trifluoromethoxy)phenyl)cyclopropyl)carbamate;
Ethyl(S)-(1-(4-fluoro-3-(trifluoromethyl)phenyl)cyclopropyl)(pyrrolidin-2-ylmethyl)carbamate;
Ethyl(S)-(1-(4-fluoro-3-(trifluoromethyl)phenyl)cyclopropyl)((1-methylpyrrolidin-2-yl)methyl)carbamate;
(S)—N-(1-(4-fluoro-3-(trifluoromethyl)phenyl)cyclopropyl)-N-(pyrrolidin-2-ylmethyl) methanesulfonamide;
(S)—N-(1-(4-fluoro-3-(trifluoromethyl)phenyl)cyclopropyl)-N-((1-methylpyrrolidin-2-yl)methyl) methanesulfonamide;
Ethyl (R)-(1-(4-fluoro-3-(trifluoromethyl)phenyl)cyclopropyl)(pyrrolidin-2-ylmethyl)carbamate;
Methyl (R)-(1-(4-fluoro-3-(trifluoromethyl)phenyl)cyclopropyl)(morpholin-3-ylmethyl) carbamate;
Methyl (R)-(1-(4-fluoro-3-(trifluoromethyl)phenyl)cyclopropyl)((4-methylmorpholin-3-yl)methyl)carbamate;
(R)—N-(1-(4-fluoro-3-(trifluoromethyl)phenyl)cyclopropyl)-N-(pyrrolidin-2-ylmethyl) methane sulphonamide;
Methyl(S)-(1-(4-fluoro-3-(trifluoromethyl)phenyl)cyclopropyl)(morpholin-3-ylmethyl) carbamate;
Methyl(S)-(1-(4-fluoro-3-(trifluoromethyl)phenyl)cyclopropyl)((4-methylmorpholin-3-yl)methyl)carbamate;
Isopropyl(S)-(1-(4-fluoro-3-(trifluoromethyl)phenyl)cyclopropyl)(pyrrolidin-2-ylmethyl)carbamate;
Methyl (R)-(1-(4-fluoro-3-(trifluoromethyl)phenyl)cyclopropyl)((2-methyl pyrrolidin-2-yl)methyl)carbamate;
Cyclopropylmethyl(S)-(1-(4-fluoro-3-(trifluoromethyl)phenyl)cyclopropyl)(pyrrolidin-2-ylmethyl)carbamate;
Methyl(S)-(1-(4-fluoro-3-(trifluoromethyl)phenyl)cyclopropyl)((2-methylpyrrolidin-2-yl)methyl)carbamate; and
Methyl(S)-(azetidin-2-ylmethyl)(1-(4-fluoromethyl)phenyl)-cyclopropyl) carbamate,
or a pharmaceutically acceptable salt thereof.

16. The method according to claim 1, wherein the subject is in need of treatment of inflammatory bowel disease (IBD).

17. The method according to claim 16, wherein the inflammatory bowel disease (IBD) is ulcerative colitis or Crohn's disease.

18. The method according to claim 1, wherein the subject is in need of treatment of hereditary xerocytosis.

19. The method according to claim 1, wherein the subject is in need of treatment of acute respiratory distress syndrome (ARDS).

* * * * *